United States Patent
Alihodzic et al.

(10) Patent No.: US 7,202,221 B2
(45) Date of Patent: Apr. 10, 2007

(54) MACROLIDES

(75) Inventors: Suleman Alihodzic, Zagreb (HR); Daniele Andreotti, Verona (IT); Andrea Berdik, Zagreb (HR); Ilaria Bientinesi, Verona (IT); Stefano Biondi, Verona (IT); Manuela Ciraco, Verona (IT); Federica Damiani, Verona (IT); Marko Djerek, Zagreb (HR); Miljenko Dumic, Zagreb (HR); Vesna Erakovic, Zagreb (HR); Antun Hutinec, Zagreb (HR); Gorjana Lazarevski, Zagreb (HR); Sergio Lociuro, Verona (IT); Natasa Marsic, Zagreb (HR); Zorica Marusic-Istuk, Zagreb (HR); Stjepan Mutak, Zagreb (HR); Alfredo Paio, Verona (IT); Drazen Pavlovic, Zagreb (HR); Anna Quaglia, Verona (IT); Wolfgang Schoenfeld, Zagreb (HR); Vlado Stimac, Zagreb (HR); Jessica Tibasco, Verona (IT)

(73) Assignees: Glaxo Group Limited, Greenford, Middlesex (GB); Pliva D.D., Zagreb (HR)

( * ) Notice: Subject to any disclaimer, the term of this patent is extended or adjusted under 35 U.S.C. 154(b) by 205 days.

(21) Appl. No.: 10/495,413

(22) PCT Filed: Nov. 13, 2002

(86) PCT No.: PCT/GB02/05101

§ 371 (c)(1),
(2), (4) Date: Sep. 20, 2004

(87) PCT Pub. No.: WO03/042228

PCT Pub. Date: May 22, 2003

(65) Prior Publication Data

US 2005/0080025 A1    Apr. 14, 2005

(30) Foreign Application Priority Data

Nov. 14, 2001    (GB) .................................. 0127349.9

(51) Int. Cl.
*A61K 31/70* (2006.01)
*C07H 17/08* (2006.01)
(52) U.S. Cl. ..................... 514/29; 536/7.2; 536/7.4
(58) Field of Classification Search ................ 536/7.2, 536/7.4; 514/29
See application file for complete search history.

(56) References Cited

U.S. PATENT DOCUMENTS 5,288,709 A    2/1994    Freiberg et al. ............... 514/29

6,262,030 B1    7/2001    Wu et al. ....................... 514/29
2002/0019355 A1    2/2002    Ma et al. ....................... 514/29

FOREIGN PATENT DOCUMENTS

| EP | 0 126 344 | 11/1984 |
|---|---|---|
| EP | 0 248 279 A | 12/1987 |
| EP | 0 508 699 A | 10/1992 |
| EP | 0 895 999 A | 2/1999 |
| WO | WO 90/11288 | 10/1990 |
| WO | WO 97/42206 | 11/1997 |
| WO | WO 00/71557 | 11/2000 |
| WO | WO 01/14397 | 3/2001 |
| WO | WO 01/63539 | 8/2001 |
| WO | WO 02/026753 | 4/2002 |
| WO | WO 02/32917 | 4/2002 |

OTHER PUBLICATIONS

Vlase et al., "Beta-Lactamase Inhibitors from Sulbactam Class III. Determination of "In Vitro" Biological Activity of New Derivatives of Sulbactam in Association with Beta-Lactam Antibiotics", (1998), Roum. Biotechnol. Lett., 3(2), pp. 137-145.

Baker et al., "Modification of Macrolide Antibiotics. Synthesis of 11-Deoxy-11-(carboxyamino-6-*O*-methylerythromycin a 11,12-(Cyclic esters) via an Intramolecular Michael Reaction of *O*-Carbamates With An α, β-Unsaturated Ketone", (1988), Journal of Organic Chemistry, 53(10), pp. 2340-2345.

*Primary Examiner*—Elli Peselev
(74) *Attorney, Agent, or Firm*—Laura K. Madden; Loretta J. Sauermelch; Mary E. McCarthy

(57) ABSTRACT

The present invention relates to 14 or 15 membered macrolides substituted at the 4' position of formula (I) and pharmaceutically acceptable salts and solvates thereof, to processes for their preparation and their use in therapy or prophylaxis of systemic or topical bacterial infections in a human or animal body

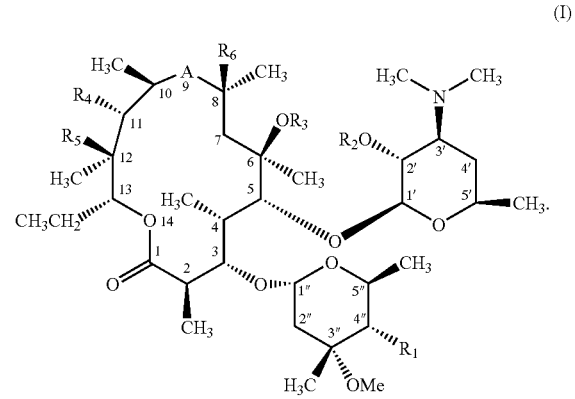

9 Claims, No Drawings

MACROLIDES

CROSS REFERENCES TO RELATED APPLICATIONS

This application is a National Stage Application filed under 35 U.S.C. § 371 of PCT/GB02/05101, filed on Nov. 13, 2002.

The present invention relates to novel semi synthetic macrolides having antibacterial activity. More particularly this invention relates to 14 or 15 membered macrolides substituted at the 4" position, to processes for their preparation, to compositions containing them and to their use in medicine.

Thus, the present invention provides compounds of general formula (I)

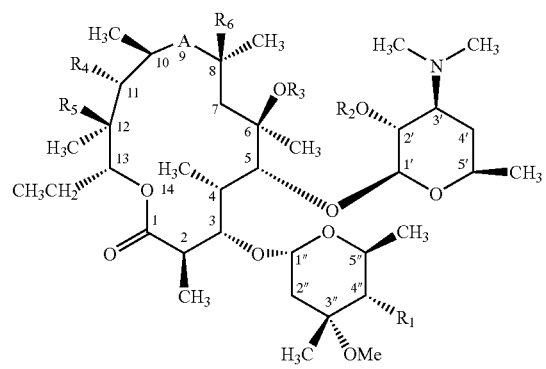

wherein

A is a bivalent radical selected from:
—C(O)—, —C(O)NH—, —NHC(O)—, —N(CH$_3$)—CH$_2$—, —CH$_2$—N(CH$_3$) or
—C(NOCH$_2$OCH$_2$CH$_2$OCH$_3$)—;

$R_1$ is OC(O)(CH$_2$)$_n$XR$_7$;

$R_2$ is hydrogen or a hydroxyl protecting group;

$R_3$ is hydrogen, C$_{1-4}$alkyl or C$_{3-6}$alkenyl optionally substituted by 9 to 10 membered fused bicyclic heteroaryl;

$R^4$ is hydroxy or C$_{3-6}$alkenyloxy optionally substituted by 9 to 10 membered fused bicyclic heteroaryl;

$R_5$ is hydroxy or $R_4$ and $R_5$ taken together with the intervening atoms form a cyclic group having the following structure:

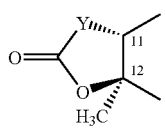

wherein Y is a bivalent radical selected from:
—CH$_2$—, —CH(CN)—, —O—, —N(R$_8$)— and —CH(SR$_8$)—;

$R_6$ is hydrogen or fluorine;

$R_7$ is a heterocyclic group having the following structures:

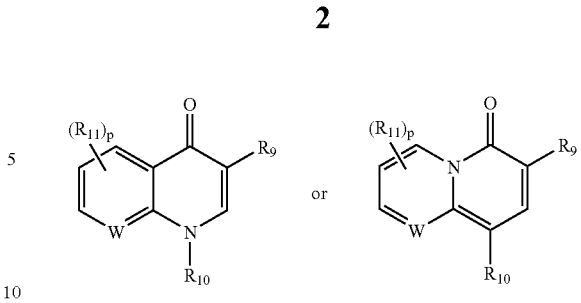

$R_8$ is hydrogen or C$_{1-4}$alkyl substituted by a group selected from:
optionally substituted phenyl,
optionally substituted 5 or 6 membered heteroaryl,
optionally substituted 9 to 10 membered fused bicyclic heteroaryl;

$R_9$ is hydrogen, C(O)OR$_{12}$, C(O)NHR$_{12}$ or C(O)CH$_2$NO$_2$;

$R_{10}$ is hydrogen, C$_{1-4}$alkyl, C$_{3-7}$cycloalkyl, optionally substituted phenyl or benzyl;

$R_{11}$ is halogen, C$_{1-4}$alkyl, C$_{1-4}$thioalkyl, C$_{1-4}$alkoxy, NH$_2$, NH(C$_{1-4}$alkyl) or N(C$_{1-4}$alkyl)$_2$;

$R_{12}$ is hydrogen or C$_{1-4}$alkyl;

$R_{13}$ is hydrogen, C$_{1-4}$alkyl, C$_{3-7}$cycloalkyl, optionally substituted phenyl or benzyl, acetyl or benzoyl;

X is —U(CH$_2$)$_m$Z- or X is a group selected from:

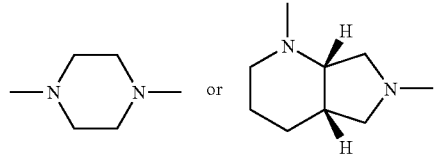

U and Z independently are a divalent radical selected from:
—N(R$_{13}$)—, —O—, —S(O)$_q$—, —N(R$_{13}$)C(O)—, —C(O)N(R$_{13}$)—, —N[C(O)R$_{13}$]—, W is a carbon or a nitrogen atom;

n is 0 or an integer from 1 to 5;

m is an integer from 2 to 8;

p is 0, 1 or 2;

q is 0, 1 or 2;

and pharmaceutically acceptable salts and solvates thereof.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, fumarates and maleates.

The solvates may, for example, be hydrates.

References hereinafter to a compound according to the invention include both compounds of formula (I) and their pharmaceutically acceptable acid addition salts together with pharmaceutically acceptable solvates.

The compound of formula (I) and salts thereof may form solvates (e.g. hydrates) and the invention includes all such solvates.

In the general formula (I) as drawn the solid wedge shaped bond indicates that the bond is above the plane of the paper. The broken bond indicates that the bond is below the plane of the paper.

Compounds wherein R$_2$ represents a hydroxyl protecting group are in general intermediates for the preparation of other compounds of formula (I).

When the group $OR_2$ is a protected hydroxyl group this is conveniently an ether or an acyloxy group. Examples of particularly suitable ether groups include those in which $R_2$ is a trialkylsilyl (i.e. trimethylsilyl). When the group $OR_2$ represents an acyloxy group, then examples of suitable groups $R_2$ include acetyl or benzoyl.

When $R_7$ is a heterocyclic group having the following structure:

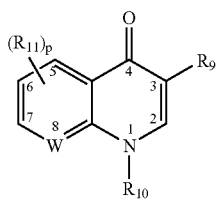

wherein W is carbon or nitrogen, said heterocyclic is linked in the 7 or 6 position to the Z group as above defined or to one of the nitrogen atoms contained in the following structures:

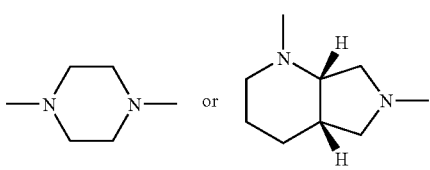

When $R_7$ is a heterocyclic group having the following structure:

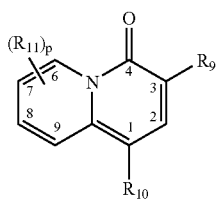

said heterocyclic is linked in the 8 or 7 position to the Z group as above defined or to one of the nitrogen atoms contained in the following structures:

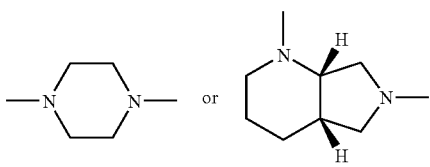

When $R_7$ is a heterocyclic group having the following structure:

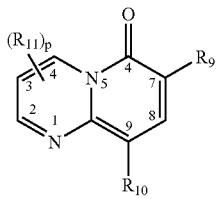

said heterocyclic is linked in the 2 or 3 position to the Z group as above defined or to one of the nitrogen atoms contained in the following structures:

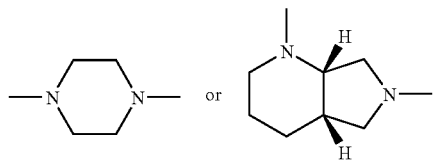

The term $C_{1-4}$alkyl as used herein as a group or a part of the group refers to a straight or branched alkyl group containing from 1 to 4 carbon atoms; examples of such groups include methyl, ethyl, propyl, isopropyl, n-butyl, isobutyl, tert-butyl.

The term $C_{2-6}$alkenyl group as used herein as a group or a part of the group refers to a straight or branched alkenyl group containing from 2 to 6 carbon atoms; examples of such groups include 2-propenyl, 1-propenyl, isopropenyl, 2-butenyl, 2-pentenyl, 2-hexenyl and the like. It will be appreciated that in groups of the form —O—$C_{2-6}$alkenyl, the double bond is preferably not adjacent to the oxygen.

The term $C_{3-7}$cycloalkyl group means a non-aromatic monocyclic hydrocarbon ring of 3 to 7 carbon atoms such as, for example, cyclopropyl, cyclobutyl, cyclopentyl, cyclohexyl or cycloheptyl.

The term 5 or 6 membered heteroaryl as used herein as a group or a part of the group refers to furanyl, thiophenyl, imidazolyl, oxazolyl, thiazolyl, pyrazolyl, pyridyl, pyridinium, pyridazinyl or pyrimidinyl.

The term halogen refers to a fluorine, chlorine, bromine or iodine atom.

The term $C_{1-4}$alkoxy group may be a straight chain or a branched chain alkoxy group, for example methoxy, ethoxy, propoxy, prop-2-oxy, butoxy, but-2-oxy or methylprop-2-oxy.

The term 9 to 10 membered fused bicyclic heteroaryl as used herein as a group or a part of the group refers to quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl or benzothiophenyl.

The terms optionally substituted phenyl, optionally substituted 5 or 6 membered heteroaryl or optionally substituted 9 to 10 membered fused bicyclic heteroaryl refer to a group which is substituted by 1 to 3 groups selected from: halogen, $C_{1-4}$alkyl, $C_{1-4}$alkoxy, hydroxy, nitro, cyano, amino, $C_{1-4}$alkylamino or di$C_{1-4}$ alkylamino, phenyl or 5 or 6 membered heteroaryl.

Preferred compounds of formula (I) are those wherein $R_2$ is hydrogen.

In one embodiment, $R_3$ is hydrogen or $C_{1-4}$alkyl, for example methyl, ethyl or propyl.

When A is —C(O)—, $R_6$ is preferably hydrogen and $R_3$ is preferably $C_{1-4}$alkyl (i.e. methyl) or $R_6$ is preferably fluorine and $R_3$ is preferably hydrogen.

When A is —C(O)—, $R_4$ and $R_5$ are preferably hydroxy or $R_4$ and $R_5$ taken together with the intervening atoms form a cyclic group having the following structure:

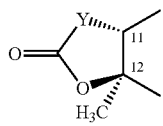

wherein Y is preferably —N($R_8$)— and $R_8$ is hydrogen or $C_{1-4}$alkyl such as methyl or ethyl.

When A is —NHC(O)—, —C(O)NH—, —N(CH$_3$)CH$_2$— —CH$_2$—N(CH$_3$)— or —C(NOCH$_2$OCH$_2$CH$_2$OCH$_3$) and $R_4$ or $R_5$ is hydroxy or $R_4$ and $R_5$ taken together with the intervening atoms form a cyclic group having the following structure:

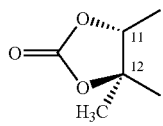

$R_6$ is preferably hydrogen and $R_3$ is preferably hydrogen, $C_{1-4}$alkyl (i.e. methyl) or 2-propenyl.

When A is —NHC(O)—, —C(O)NH—, —N(CH$_3$)CH$_2$—, —CH$_2$—N(CH$_3$) or —C(NOCH$_2$OCH$_2$CH$_2$OCH$_3$) and $R_4$ and $R_5$ taken together with the intervening atoms form a cyclic group having the following structure:

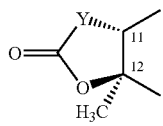

wherein Y is a bivalent radical selected from —CH$_2$—, —CH(CN)—, —N($R_8$)—, $R_6$ is preferably hydrogen and $R_3$ is preferably $C_{1-4}$alkyl (i.e. methyl) or 2-propenyl.

When n is 0, U is preferably selected from —N($R_{13}$)—, —O— and —S—.

In the compounds of formula (I) n is preferably 1 or 2. Within this class, compounds wherein n is 2 are particularly preferred.

Preferred class of compounds of formula (I) are those wherein X is NH(CH$_2$)$_{2-5}$NH or

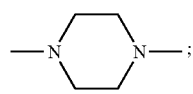

within this class, compounds in which X is NH(CH$_2$)$_{2-3}$NH are particularly preferred.

Another preferred class of compounds of formula (I) are those wherein X is N($R_{13}$)(CH$_2$)$_{2-3}$NH and $R_{13}$ is $C_{1-4}$alkyl such as methyl, or acetyl.

A further preferred class of compounds of formula (I) is that wherein $R_7$ is a heterocyclic of the following formula:

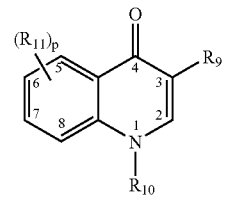

Within this class of compounds, those compounds wherein p is 0 or 1, $R_{11}$ is halogen (i.e. chloro or fluoro) at position 6 or 7, $R_9$ is carboxy and $R_{10}$ is methyl, ethyl or cyclopropyl are particularly preferred.

A particular preferred class of compounds according to the invention are those wherein $R_2$ is hydrogen, X is NH(CH$_2$)$_{2-3}$NH, $R_7$ is a heterocyclic group of the following formula:

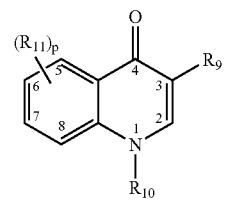

wherein p is 0 or 1, $R_{11}$ is halogen (i.e. chloro or fluoro) at position 6 or 7, $R_9$ is carboxy and $R_{10}$ is ethyl or cyclopropyl.

Another preferred class of compounds are those wherein $R_9$ is C(O)O$R_{12}$ and $R_{12}$ is $C_{1-4}$alkyl, in particular methyl.

A further preferred class of compounds are those wherein $R_{11}$ is $C_{1-4}$alkoxy, for example methoxy at position 8.

When $R_3$ is $C_{3-6}$alkenyl substituted by 9 to 10 membered fused bicyclic heteroaryl, 9 to 10 membered fused bicyclic heteroaryl is preferably 2-quinolyl or 3-quinolyl, $R_4$ and $R_5$ are preferably hydroxy and $R_6$ is hydrogen. Within this class of compounds, the compounds in which $R_2$ is hydrogen, X is NH(CH$_2$)$_{2-3}$NH, $R_7$ is a heterocyclic of the following formula:

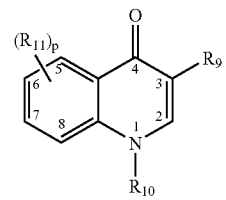

wherein p is 1, $R_{11}$ is halogen (i.e. chloro or fluoro) at position 6 or 7, $R_9$ is carboxy and $R_{10}$ is ethyl or cyclopropyl are particularly preferred.

In one embodiment, Y is a bivalent radical selected from —CH$_2$—, —CH(CN)—, —O— and —N($R_8$)—.

Particularly preferred compounds of the invention are:

4"-O-[3-[[2-[(3-carboxy-7-chloro-1-cyclopropyl-1,4-dihydro-4-oxo-6-quinolinyl)amino]ethyl]amino]propionyl]-8a-aza-8a-homoerythromycin A;

4"-O-[3-[[2-[(3-carboxy-1-cyclopropyl-1,4-dihydro-6-fluoro-4-oxo-7-quinolinyl)amino]ethyl]amino]propionyl]-8a-aza-8a-homoerythromycin A;

4"-O-[3-[[2-[(3-arboxy-7-chloro-1-cyclopropyl-1,4-dihydro-4-oxo-6-quinolinyl)amino]ethyl]amino]propionyl]-6-O-methyl-8a-aza-8a-homoerythromycin A;

4"-O-[3-[[2-[(3-carboxy-1-cyclopropyl-1,4-dihydro-6-fluoro-4-oxo-7-quinolinyl)amino]ethyl]amino]propionyl]-6-O-methyl-8a-aza-8a-homoerythromycin A;

4"-O-[3-[[2-[(7-chloro-1-cyclopropyl-1,4-dihydro-3-methoxycarbonyl-4-oxo-6-quinolinyl)amino]ethylamino]propionyl]-6-O-methyl-8a-aza-8a-homoerythromycin A;

4"-O-[3-[[2-[(3-carboxy-1,4-dihydro-1-ethyl-4-oxo-7-quinolinyl)amino]ethyl]amino]propionyl]-6-O-methyl-8a-aza-8a-homoerythromycin A;

4"-O-[3-[(2-[(3-carboxy-1-cyclopropyl-1,4-dihydro-4-oxo-7-quinolinyl)amino]ethyl]amino]propionyl]-6-O-methyl-8a-aza-8a-homoerythromycin A;

4"-O-[3-[[2-[(3-carboxy-7-chloro-1-cyclopropyl-1,4-dihydro-4-oxo-6-quinolinyl)amino]ethyl]amino]propionyl]-6-O-ethyl-8a-aza-8a-homoerythromycin A;

4"-O-[3-[[2-[(3-carboxy-7-chloro-1-cyclopropyl-1,4-dihydro-4-oxo-6-quinolinyl)amino]ethyl]amino]propionyl]-propyl-8a-aza-8a-homoerythromycin A;

4"-O-[3-([2-[(3-carboxy-7-chloro-1-cyclopropyl-1,4-dihydro-4-oxo-6-quinolinyl)amino]ethyl]amino]propionyl]-6-O-methyl-9a-aza-9a-homoerythromycin A;

4"-O-[3-[[2-[(3-carboxy-7-chloro-1-cyclopropyl-1,4-dihydro-4-oxo-6-quinolinyl)amino]ethyl]amino]propionyl]-11,12-dideoxy-6-O-methyl-11,12-(methylaminocarbonyloxy)-erythromycin A;

11,12-(aminocarbonyloxy)-4"-O-[3-[[2-[(3-carboxy-7-chloro-1-cyclopropyl-4-oxo-1,4-dihydro-6-quinolinyl)amino]ethyl]amino]propiony]-11,12-dideoxy-6-O-methyl-erythromycin A;

11,12-(aminocarbonyloxy)-4"-O-[3-[[2-[(3-carboxy-1-cyclopropyl-1,4-dihydro-6-fluoro-4-oxo-7-quinolinyl)amino]ethyl]amino]propiony]-11,12-dideoxy-6-O-methyl-erythromycin A;

4"-O-[3-[[2-[(3-carboxy-7-chloro-1-cyclopropyl-1,4-dihydro-4-oxo-6-quinolinyl)amino]ethyl]amino]propionyl]-6-O-methyl-erythromycin A;

4"-O-[3-[[2-[(3-carboxy-1-cyclopropyl-6-fluoro-1,4-dihydro-4-oxo-7-quinolinyl)-amino]ethyl]amino]propionyl]-O-methyl-erythromycin A;

4"-O-[3-[[2-[(3-carboxy-1-cyclopropyl-4-oxo-1,4-dihydro-6-quinolinyl)amino]ethyl]amino]propionyl]-6-O-methyl-erythromycin A;

4"-O-[3-[[2-[(3-carboxy-7-chloro1,4-dihydro-1-ethyl-4-oxo-6-quinolinyl)amino]ethyl]amino]propiony]-6-O-methyl-erythromycin A and 4"-[3-[[2-[(3-carboxy-1,4-dihydro-1-ethyl-6-fluoro-4-oxo-7-quinolinyl)amino]ethyl]amino]propiony]-6-O-methyl-erythromycin A;

4"-O-[3-[[2-[(3-carboxy-1-cyclopropyl-1,4-dihydro-4-oxo-7-quinolinyl)amino]ethyl]amino]propionyl]-6-O-methyl-erythromycin A;

(11S,11aR)-11-carboxycyanomethyl)-4"-O-[3-[[2-[(3carboxy- 1,4-dihydro-1-ethyl-4-oxo-7-quinolinyl)amino]ethyl]amino]propionyl]-11-deoxy-6-O-methyl-erythromycin A;

(11S,11aR)-11-(carboxycyanomethyl)-4"-O-[3-[[2-[(3-carboxy-1-cyclopropyl-1,4-dihydro-4-oxo-7-quinolinyl)amino]ethyl]amino]propionyl]-11-deoxy-6-O-methyl-erythromycin A;

(11S,11aR)-4"-O-[3-[[2-[(3-carboxy-7-chloro-1-cyclopropyl-1,4-dihydro-4-oxo-6-quinolinyl)amino]ethyl]amino]propionyl]-11-(carboxycyanomethyl)-11-deoxy-6-O-methyl-erythromycin A;

4"-O-[3-[4-(3-carboxy-7-chloro-1-cyclopropyl-1,4-dihydro-4-oxo-6-quinolinyl)amino]ethyl]amino]propionyl]-roxithromycin;

4"-O-[3-[4-(3-carboxy-1-cyclopropyl-1,4-dihydro-6-fluoro-4-oxo-7-quinolinyl)amino]ethyl]amino]propionyl]-roxithromycin;

4"-O-[3-[[2-[(3-carboxy-7-chloro-1-cyclopropyl-1,4-dihydro-4-oxo-3-quinolinyl)amino]ethyl]amino]propionyl]-azithromycin;

11,12-carbonate-4"-O-[3-[[2-[(3-carboxy-1-cyclopropyl-1,4-dihydro-6-fluoro-4-oxo-7-quinolinyl)amino]ethyl]amino]propiony]-11,12-dideoxy azithromycin;

4"-O-[3-[[2-[(3-carboxy-7-chloro-1-cyclopropyl-1,4-dihydro-4-oxo-3-quinolinyl)amino]ethyl]amino]propiony]-6-O-methyl-azithromycin;

11,12-carbonate-4"-O-[3-[[2-[(3-carboxy-7-chloro-1-cyclopropyl-1,4-dihydro-4-oxo-6-quinolinyl)amino]ethyl]amino]propionyl]-11,12-dideoxy-azithromycin;

11,12carbonate-4"-O-[3-[[2-[(3-carboxy-1-cyclopropyl-1,4-dihydro-6-fluoro-4-oxo-7-quinolinyl)amino]ethyl]amino]propiony]-11,12-dideoxy azithromycin.

Further preferred compounds of the invention are:

4"-O-[3-[[2-[(3-carboxy-7-chloro-1-cyclopropyl-1,4-dihydro-4-oxo-6-quinolinyl)amino]ethyl]amino]propionyl-6-O-methyl-8a-aza-8a-homoerythromycin A;

11,12-carbonate-4"-O-[3-[[2-[(3-carboxy-7-chloro-1-cyclopropyl-1,4-dihydro-4-oxo-6-quinolinyl)amino]ethyl]amino]propionyl]-11,12-dideoxy-azithromycin;

11,12-carbonate-4"-O-[3-[[2-[(3-carboxy-1-cyclopropyl-1,4-dihydro-6-fluoro-4-oxo-7-quinolinyl)amino]ethyl]amino]propiony]-11,12-dideoxy azithromycin;

11,12-carbonate-4"-O-[3-[[2-[(3-carboxy-1-cyclopropyl-1,4-dihydro-4-oxo-7-quinolinyl)amino]ethyl]-amino]propiony]-11,12-dideoxy-azithromycin;

4"-O-[3-[[2-[(3-carboxy-7-chloro-1-cyclopropyl-1,4-dihydro-4-oxo-6-quinolinyl)amino]ethyl]amino]propiony]-azithromycin;

4"-O-[3-[[2-[(3-carboxy-7-chloro-1-cyclopropyl-1,4-dihydro-4-oxo-6-quinolinyl)amino]ethyl]amino]propionyl]-11,12-dideoxy-11,12-(ethylaminocarbonyloxy)-6-O-methyl-erythromycin A;

4"-O-[3-[[2-[(3-carboxy-7-chloro-1-cyclopropyl-1,4-dihydro-4-oxo-4-quinolinyl)amino]ethyl]amino]propionyl]-6-O-methyl-erythromycin A;

4"-O-[3-[[2-[(3-carboxy-1,4-dihydro-1-ethyl-4-oxo-7-quinolinyl)amino]ethyl]amino)propionyl]-6-O-methyl-erythromycin A;

4"-O-[3-[[2-[(3-carboxy-1-cyclopropyl-1,4-dihydro-4-oxo-7-quinolinyl)amino]ethyl]amino]propionyl]-6-O-methyl-erythromycin A;

4"-O-[3-[[2-[(3-carboxy-1-cyclopropyl-1,4-oxo-1,4-dihydro-6-quinolinyl)amino]ethyl]amino]propionyl]-6-O-methyl-erythromycin A;

(11S,11aR)-4"-O-[3-[[2-[(3carboxy-7-chloro-1-cyclopropyl-1,4-dihydro-4-oxo-6-quinolinyl)amino]ethyl]amino]propionyl]-11-carboxycyanomethyl)-11-deoxy-6-O-methyl-erythromycin A;

(11S,11aR)-11-(carboxycyanomethyl)-4"-O-[3-[[2-[(3-carboxy-1-cyclopropyl-1,4-dihydro-4-oxo-7-quinolinyl)amino]ethyl]amino]propionyl]-11-deoxy-6-O-methyl-erythromycin A;

4"-O-[3-[4-(3-carboxy-7-chloro-1-cyclopropyl-1,4-dihydro-4-oxo-6-quinolinyl)amino]ethyl]amino]propionyl]-roxithromycin;

4"-O-(3-(2-(3-carboxy-7-chloro-1-cyclopropyl-1,4-oxo-1,4-dihydro-6-quinolinyl)amino)ethyl)-methyl-amino)propionyl)-11,12-dideoxy-11,12-(ethylaminocarbonyloxy)-6-O-methylerythromycin A;

4"-O-{3-[(2-[(3-carboxymethyl-7-chloro-1-cyclopropyl-4-oxo-1,4-dihydro-6-quinolin yl)amino]ethyl)amino]propiony}-6-O-methyl-erythromycin A;

11,12-(aminocarbonyloxy)-4"-O-{3-[(2-[(3-carboxy-1-cyclopropyl-4-oxo-1,4-dihydro-6-quinolinyl)amino]ethyl)amino]propionyl}-11,12-dideoxy-6-O-methyl-erythromycin A;

4"-O-[3-[[2-[(3-carboxy-7-chloro-1-cyclopropyl-1,4-dihydro-4-oxo-6-quinolinyl)amino]ethyl]-methyl-amino]propionyl]-azithromycin;

11,12-carbonate-4"-O-[3-[([2-[(3-carboxy-1-cyclopropyl-1,4-dihydro-4-oxo-6-quinolinyl)amino]ethyl]methylamino]propionyl]-11,12-dideoxy-azithromycin;

4"-O-3-{[2-(7-chloro-1-cyclopropyl-3-methoxycarbonyl-4-oxo-1,4-dihydro-quinolin-6-ylamino)ethyl]-amino}-propionyl)-azithromycin;

4"-O-(3-{[2-(7-chloro-1-cyclopropyl-3-methoxycarbonyl-4-oxo-1,4-dihydro-quinolin-6-ylamino)-ethyl]-methyl-amino}-propionyl)-azithromycin;

4"-O-{3-[(2-[(3-carboxy-1-cyclopropyl-1,4-dihydro-4-oxo-7-quinolinyl)amino]ethyl)methylamino]propionyl}-azithromycin; and 4"-O-[3-[[2-[(3-carboxy-1-ethyl-1,4-dihydro-4-oxo-6-quinolinyl)amino]ethyl]amino]propionyl]-6-O-methyl-erythromycin A.

Compounds according to the invention also exhibit a broad spectrum of antibacterial activity against a wide range of clinical pathogenic microorganisms. For example, using a standard microtiter broth serial dilution test, compounds of the invention have been found to exhibit useful levels of activity against a wide range of pathogenic microorganisims including strains of *Staphylococcus aureus, Streptopococcus pneumoniae, Moraxella catarrhalis, Streptococcus pyogenes, Haemophilus influenzae, Chlamydia pneumoniae, Mycoplasma pneumoniae* and *Legionella pneumophila*. The compounds of the invention may therefore be used for treating a variety of diseases caused by pathogenic bacteria in human beings and animals. The compounds of the invention may also be active against resistant strains, for example erythromycin resistant strains. In particular, the compounds of the invention may be active against erythromycin resistant strains of *Streptococcus pneumoniae* and *Streptococcus pyogenes.*

Thus, according to another aspect of the present invention, we provide a compound of formula (I) or a physiologically acceptable salt thereof for use in the therapy or prophylaxis of systemic or topical bacterial infections in a human or animal subject.

According to a further aspect of the invention we provide the use of a compound of formula (I) or a physiologically acceptable salt thereof for the manufacture of a therapeutic agent for the treatment or prophylaxis of systemic or topical bacterial infections in a human or animal body.

According to a yet further aspect of the invention we provide a method of treatment of the human or non-human animal body to combat bacterial infections which method comprises administering to the body an effective amount of a compound of formula (I) or a physiologically acceptable salt thereof.

While it is possible that, for use in therapy, a compound of the invention may be administered as the raw chemical it is preferable to present the active ingredient as a pharmaceutical formulation.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, eg dichlorodifluoromethane, trichlorofluoromethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01–99% of the active material. For topical administration, for example, the composition will generally contain from 0.01–10%, more preferably 0.01–1% of the active material.

For systemic administration the daily dose as employed for adult human treatment it will range from 2–100 mg/kg body weight, preferably 5–60 mg/kg body weight, which may be administered in 1 to 4 daily doses, for example, depending on the route of administration and the condition of the patient. When the composition comprises dosage units, each unit will preferably contain 200 mg to 1 g of active ingredient. The duration of treatment will be dictated by the rate of response rather than by arbitrary numbers of days.

Compounds of general formula (I) and salts thereof may be prepared by the general method outlined hereinafter. In the following description, the groups $R_1$, $R_2$, $R_3$, $R_4$, $R_5$, $R_6$, $R_7$, $R_8$, $R_9$, $R_{10}$, $R_{11}$, $R_{12}$, $R_{13}$, A, X, Y, U, Z, W, n, m, p, and q have the meaning defined for the compounds of formula (I) unless otherwise stated. The groups $XR_7$ and $ZR_7$ are $XR_7$ and $ZR_7$ as defined for formula (I) or groups convertible to $XR_7$ and $ZR_7$ respectively. Conversion of a group to a $XR_7$ or $ZR_7$ group typically arises if a protecting group is needed during the reactions described below. A comprehensive discussion of the ways in which such groups may be protected and methods for cleaving the resulting protected derivatives is given in for example T. W. Greene and P. G. M Wuts in Protective Groups in Organic Synthesis $2^{nd}$ ed., John Wiley & Son, Inc 1991.

Compounds of formula (I) wherein n is an integer 1 to 5, may be prepared by reaction of 4" hydroxy of formula (II) with a suitable activated derivative of the carboxylic acid (III), followed where necessary by subsequent removal of the hydroxyl protecting group $R_2$.

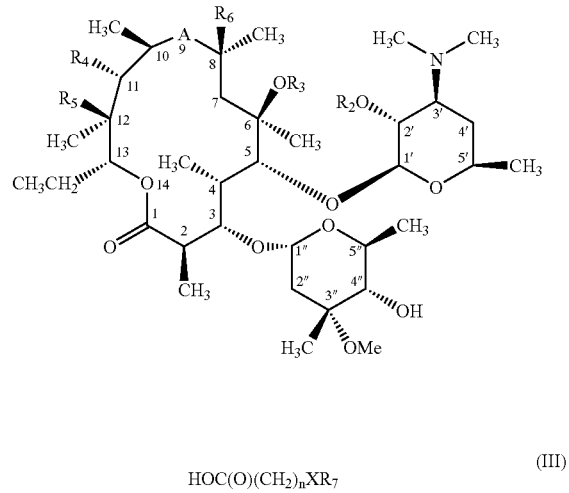

(II)

HOC(O)(CH₂)ₙXR₇ (III)

Suitable activated derivatives of the carboxyl group include the corresponding acyl halide, mixed anhydride or activated ester such as a thioester. The reaction is preferably carried out in a suitable aprotic solvent such as a halohydrocarbon (e.g. dichloromethane) or N,N-dimethylformamide optionally in the presence of a tertiary organic base such as dimethylaminopyridine or triethylamine or in the presence of inorganic base (i.e sodium hydride) and at a temperature within the range of 0° to 120° C.

Compounds of formula (I) wherein n is 0, U is a group selected from:

—N($R_{13}$)—, —O— and —S(O)$_q$— wherein q is 0, may be prepared by reaction of compounds of formula (II), in which the 4" hydroxy is suitable activated, with a compound of formula $XR_7$ (IV), followed where necessary by subsequent removal of the hydroxyl protecting group $R_2$. Suitable activated derivatives of the 4" hydroxy group include for example carbonyl imidazole. The reaction is preferably carried out in a suitable aprotic solvent such as a halohydrocarbon (e.g. dichloromethane) or N,N-dimethylformamide optionally in the presence of a tertiary base such as dimethylaminopyridine or triethylamine and at a temperature within the range of 0° to 120° C.

Compounds of formula (I) wherein n is 0 and U is —N($R_{13}$)C(O)—, may be prepared by reaction of compounds of formnula (V),

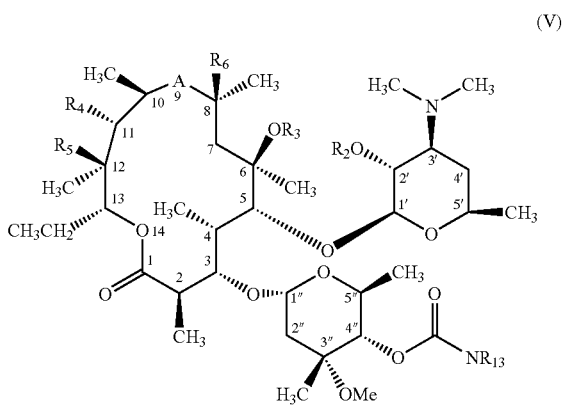

(V)

with a compound of formula HOC(O)C(O)(CH₂)ₘZR₇(VI), followed where necessary by subsequent removal of the hydroxyl protecting group $R_2$. The reaction is preferably carried out in a suitable aprotic solvent such as a halohydrocarbon (e.g. dichloromethane) or N,N-dimethylformamide optionally in the presence of a tertiary base such as dimethylaminopyridine or triethylamine and at a temperature within the range of 0° to 120° C.

Compounds of formnula (V) may be prepared by treatment of compounds of formula (II), in which the 4" hydroxy is suitable activated, with amine $NR_{13}$(VIIa). Suitable activated derivatives of the 4" hydroxy group include for example carbonyl imidazole.

Compounds of formula (I) wherein n is 0 and U is —C(O)N($R_{13}$)— may be prepared by reaction of 4" hydroxy of formula (II) with a suitable activated derivative of the carboxylic acid HOC(O)N($R_{13}$)(CH₂)ₘZR₇(VIIb) followed where necessary by subsequent removal of the hydroxyl protecting group $R_2$.

In a preferred embodiment of the invention compounds of formula (I) wherein n is 1 to 5 and U is a group selected from —N(R$_{13}$)—, —O—, —S—, may be prepared by reaction of compounds of formula (VII),

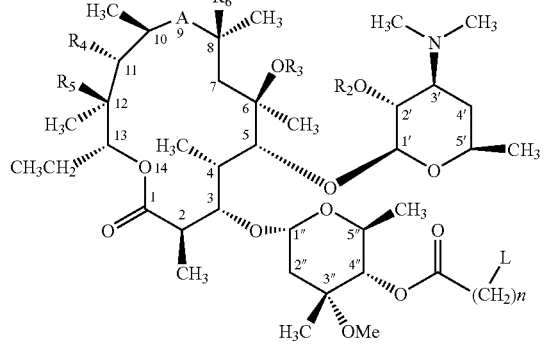

(VII)

wherein n is an integer from 1 to 5 and L is a suitable leaving group, with XR$_7$ (IV) in which U is a group selected from —N(R$_{13}$)—, —O—, —S—. The reaction is preferably carried out in a solvent such as a halohydrocarbon (e.g. dichloromethane), an ether (e.g. tetrahydrofuran, dimethoxyethane), acetonitrile or ethyl acetate and the like), dimethylsulphoxide, N,N-dimethylformamide, 1-methyl-pyrrolidone and in the presence of a base, followed, if desired, by removal of the hydroxyl protecting group R$_2$. Examples of the bases which may be used include organic base such as diisopropylethylamine, triethylamine, 1,8-diazabicyclo[5.4.0]undec-7-ene, or inorganic base such as potassium hydroxide, cesium hydroxide, tetraalkylammonium hydroxyde, sodium hydride, potassium hydride and the like. Suitable leaving groups for this reaction include halogen (e.g. chlorine, bromine or iodine) or a sulfonyloxy group (e.g. tosyloxy or methanesulfonyloxy).

Compounds of formula (VII) may be prepared by reaction of a compound of formula (II), wherein R$_2$ is a hydroxyl protecting group; with a suitable activated derivative of the carboxylic acid HOC(O)(CH$_2$)$_n$L(VIII), wherein L is a suitable leaving group as above defined. Suitable activated derivatives of the carboxyl group are those defined above for carboxylic acid (III). The reaction is carried out using the condition described above for the reaction of a compound of formula (II) with carboxylic acid (III).

In a further embodiment of the invention compounds of formula (I) of wherein n is 2, U is a group selected from:

—N(R$_{13}$)—, —O— and —S—, may be prepared by Michael reaction of a compound of formula (IX), wherein R$_2$ is a hydroxyl protecting group

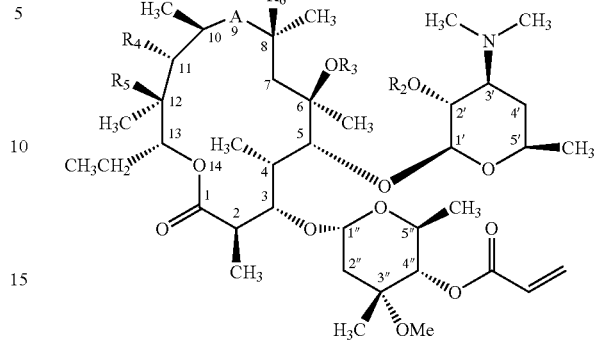

(IX)

with a compound of formula XR$_7$(IV). The reaction is suitably carried out in a solvent such as dimethylsulphoxide, N,N-dimethylformamide, 1-methyl-pyrrolidone, a halohydrocarbon (e.g. dichloromethane), an ether (e.g. tetrahydrofuran, dimethoxyethane), acetonitrile or ethyl acetate or alchool(e.g methanol, isopropanol) and the like and in the presence of a base, followed, if desired, by removal of hydroxyl protecting group R$_2$.

Compounds of formula (I) may be converted into other compounds of formula (I). Thus compounds of formula (I) wherein U is —S(O)$_q$ and q is 1 or 2 may be prepared by oxidation of the corresponding compound of formula (I) wherein q is 0. The oxidation is preferably carried out using a peracid, e.g. peroxybenzoic acid, followed by treatment with a phosphine, such as triphenylphosphine. The reaction is suitably carried out in an organic solvent such as methylene chloride.

Compounds of formula (II) wherein A is —C(O)NH— or —NHC(O)—, R$_4$ or R$_5$ are hydroxy, R$_3$ is hydrogen and R$_6$ is hydrogen are known compounds or they may be prepared by analogous methods to those known in the art. Thus they can be prepared according to the procedures described in EP 507595 and EP 503932.

Compounds of formula (II), wherein A is —C(O)NH— or —NHC(O)—, R$_4$ or R$_5$ are hydroxy and R$_3$ is C$_{1-4}$alkyl or C$_{3-6}$alkenyl optionally substituted by 9 to 10 membered fused bicyclic heteroaryl and R$_6$ is hydrogen are known compounds or they may be prepared by analogous methods to those known in the art. Thus they can be prepared according to the procedures described in WO 9951616 and WO 0063223.

Compounds of formula (II), wherein A is —C(O)NH— or —NHC(O)—, —N(CH$_3$)—CH$_2$—, —CH$_2$—N(CH$_3$)—, R$_4$ and R$_5$ taken together with the intervening atoms form a cyclic group having the following structure:

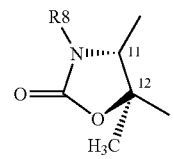

$R_3$ is $C_{1-4}$alkyl, or $C_{3-6}$alkenyl optionally substituted by 9 to 10 membered fused bicyclic heteroaryl and $R_6$ is hydrogen are known compounds or they may be prepared by analogous methods to those known in the art. Thus they can be prepared according to the procedures described in U.S. Pat. No. 6,262,030

Compounds of formula (II), wherein A is —C(O)—, $R_4$ or $R_5$ are hydroxy or $R_4$ and $R_5$ taken together with the intervening atoms form a cyclic group having the following structure:

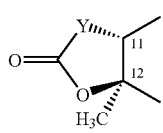

wherein Y is a bivalent radical selected from:
—O— and —N($R_8$)— and $R_3$ is $C_{1-4}$alkyl, or $C_{3-6}$alkenyl optionally substituted by 9 to 10 membered fused bicyclic heteroaryl are known compounds or they may be prepared by analogous methods to those known in the art. Thus they can be prepared according to the procedures described in EP 307177, EP 248279, WO 0078773, WO 9742204.

Compounds of formula (II), wherein A is —N(CH$_3$)—CH$_2$—, —CH$_2$—N(CH$_3$)—, $R_4$ or $R_5$ are hydroxy or $R_4$ and $R_5$ taken together with the intervening atoms form a cyclic group having the following structure:

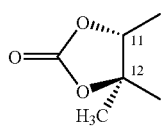

and $R_6$ is hydrogen are known compounds or they may be prepared by analogous methods to those known in the art. Thus they can be prepared according to the procedures described in EP 508699 and J. Chem. Res. Synop (1988 pages 152–153), U.S. Pat. No. 6,262,030.

Compounds of formula (II), wherein A is —C(NOCH$_2$OCH$_2$CH$_2$OCH$_3$)—, $R_4$ or $R_5$ are hydroxy or $R_4$ and $R_5$ taken together with the intervening atoms form a cyclic group having the following structure:

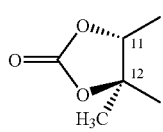

and $R_6$ is hydrogen, are known compounds or they may be prepared by analogous methods to those known in the art. Thus they can be prepared according to the procedures described in EP 284203.

Compounds of formula (II), wherein A is C(O)—, $R_4$ and $R_5$ taken together with the intervening atoms form a cyclic group having the following structure:

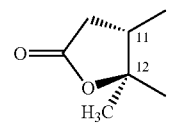

$R_6$ is hydrogen and $R_3$ is $C_{1-4}$ alkyl may be prepared by decarboxylation of a compound of formula (X), wherein $R_{14}$ is hydroxy protecting group, followed, if required by removal of the protecting group $R_2$ or $R_{14}$.

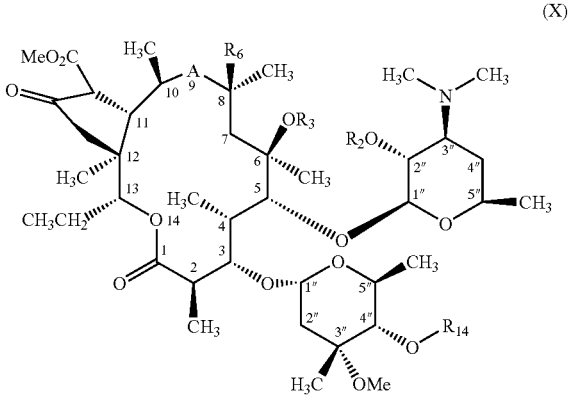

(X)

The decarboxylation may be carried out in the presence of a lithium salt such as lithium chloride, preferably in an organic solvent such as dimethylsulphoxide.

Compounds of formula (II), wherein A is C(O)—, $R_4$ and $R_5$ taken together with the intervening atoms form a cyclic group having the following structure:

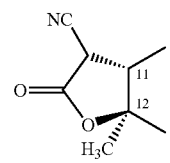

and $R_3$ is $C_{1-4}$ alkyl may be prepared by cyclisation of chlorine derivatives (XI)

(XI)

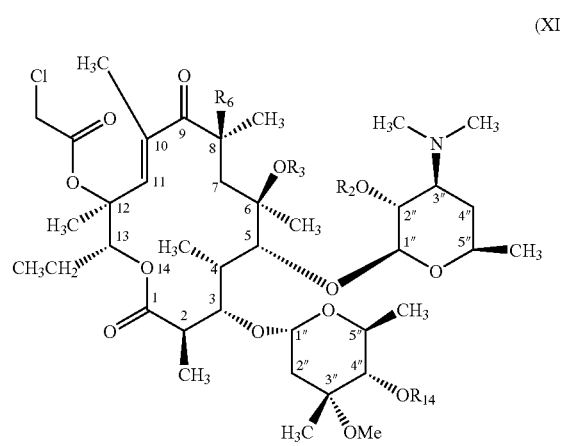

(XIII)

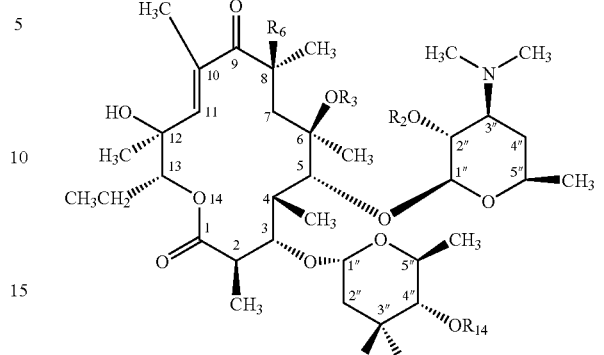

with potassium cyanide and conveniently in the presence of a solvent such as N—N dimethylformamide.

Compounds of formula (X) may be prepared by reaction of a compound of formula (XII)

(XII)

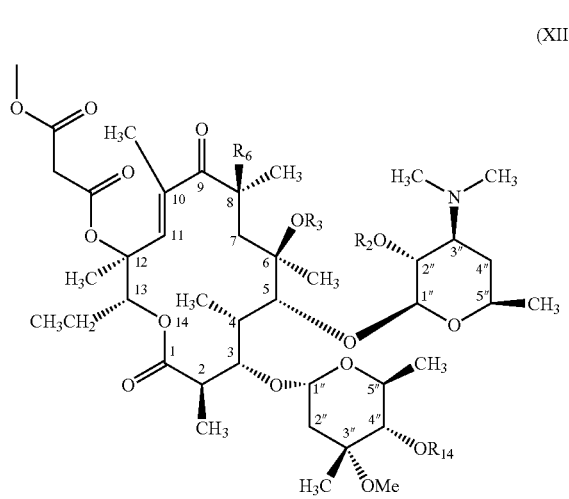

in the presence of a strong base such as 1,8 diazabicyclo [5.4.0]undec-7-ene. This reaction is conveniently carried out in an organic solvent such acetonitrile, N,N dimethylformamide and the like.

Compounds of formula (XII) may be prepared by a reaction of a compounds of formula (XIII)

with a acyl chloride of formula $ClCOCH_2COOMe$ (XIV), in the presence of a tertiary base such as pyridine, dimethylaminopyridine or triethylamine and at a temperature within the range of 0° to 30° C.

Compounds of formula (XIII) may be prepared by reacting a compound of formula (II) wherein $R_{14}$ is hydroxy protecting group, $R_4$ and $R_5$ taken together with the intervening atoms form a cyclic group having the following structure:

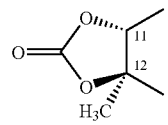

with a strong base such as 1,8 diazabicyclo[5.4.0]undec-7-ene.

Compounds of formula (XI) may be prepared by reaction of compounds of formula (XIII) with a suitable activated derivative of the acid $HOCOCH_2Cl$ (XV). Thus, for example, the esterification may be carried out by reaction with anhydride $(ClCH_2CO)_2O$ (XVI) in a suitable aprotic solvent such as a halohydrocarbon (e.g. dichloromethane) or N,N-dimethylformamide and in the presence of a tertiary base such as pyridine, dimethylaminopyridine or triethylamine and at a temperature within the range of 0° to 120° C.

Compounds of formula (III) wherein X is $-U(CH_2)_mN(R_{13})-$, in which U is $-N(R_{13})-$, $-O-$ or $-S-$ or X is a group selected from:

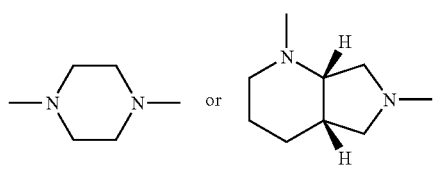

may be prepared by reaction of XR$_7$ (IV), wherein X has the meaning defined above with R$_{15}$OC(O)(CH$_2$)nL(XV) wherein R$_{15}$ is carboxyl protecting group and L is a suitable leaving group, followed by removal of R$_{15}$.

Compounds of formula (IV) wherein X is —U(CH$_2$)$_m$Z in which Z is —N(R$_{13}$)—, —O—, or —S— or X is a group selected from:

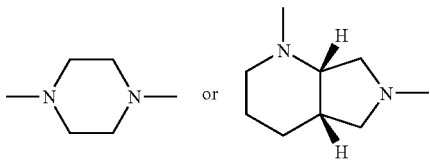

may be prepared by reaction of a compound of formula R$_7$L (XVI), wherein L is a suitable leaving group such as chlorine, fluorine or bromine, with a compound of formula —U(CH$_2$)$_m$Z (XVII) in which Z is —N(R$_{13}$)—, —O—, or —S— or with piperazine or with 1H-pyrrolo[3,4-b]pyridine, octahydro.

Suitable hydroxy protecting reagents are those described by T. W. Greene and P. G. M Wuts in Protective Groups in Organic Synthesis 2$^{nd}$ ed., John Wiley & Son, Inc 1991, which is incorporated by reference. Examples of suitable hydroxy protecting reagents include acetic anhydride, benzoic anhydride or a trialkylsilyl chloride in a protic solvent. Examples of aprotic solvents are dichloromethane, N,N-dimethylformamide, dimethylsulfoxide, tetrahydrofuran and the like. Suitable R$_{15}$ carboxyl protecting group include t-butyloxy, allyl or benzyloxy.

Acid addition salts of the compounds of general formula (I) may prepared by various methods known to those skilled in those art. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

In order that the invention may be more fully understood the following examples are given by way of illustration only.

In the Preparations and Examples, unless otherwise stated:

Proton Magnetic Resonance ($^1$H-NMR) spectra were recorded on Bruker Avance DRX 300 and DRX 500 or Varian 500 MHz as solutions in chloroform d-1, unless otherwise stated. Chemical shifts are reported in ppm downfield (δ) from Me$_4$Si, used as internal standard, and are assigned as singlets (s), doublets (d), doublets of doublets (dd), triplets (t), quartets (q) or multiplets (m).

Carbon Magnetic Resonance ($^{13}$C-NMR) spectra were recorded on Bruker Avance DPX 75 and DRX 125 MHz as solutions in chloroform d-1, unless otherwise stated. Chemical shifts are reported in ppm downfield (δ) from Me$_4$Si, used as internal standard.

Mass spectra were acquired with a Hewlett Packard 1100 MSD system equipped with a binary pump (Agilent Technologies), operating in positive electrospray ionisation mode.

LC/MS data were obtained by using a HP 1100 LC system (Agilent Technologies) equipped with a Sedex Evaporative Light Scattering Detector model 75 (Sedere) coupled with a Platform LCZ Mass Spectometer (Micromass) operating in positive electrospray ionisation mode. The chromatographic analysis conditions were: column Waters XTerra MS C18 (4.6×30 mm, 2.5 µm); flow rate 0.8 mL/min; mobile phase: aqueous solution of NH$_4$OAc (10 mM, pH 6.8) (A) and acetonitrile (B).

LC purifications were performed with a Waters 600 semi-preparative system equipped with a binary pumping system and a Jasco-UV detector. The chromatographic analysis conditions were: column Supelcosil ABZ+Plus (10 cm×21.2 mm, 5 µm); flow rate 8 mL/min; mobile phase: aqueous solution of NH$_4$OAc (10 mM, pH 6.8) (A) and acetonitrile (B).

Column chromathography was carried out over silica gel 60 (230–400 mesh ASTM—Merck AG Darnstaadt, Germany). The TLC monitoring was performed using Merck 60 F$_{254}$ as TLC plate. Resin washings were carried out on Extract-clean Tube from Alltech.

Purifications of crude products were performed by SCX-cartridges from Varian.

The following abbreviation are used in the text: brine for saturated aqueous solution of sodium chloride, DBU for 1,8-diazabicyclo[5.4.0]undec-7-ene, DCE for 1,2-dichloroethane, DCM for dichloromethane, NMP for 1-methyl-2-pyrrolidinone, DIPEA for N,N-diisopropylethylamine, DMAP for 4-dimethylaminopyridine, DMF for N,N-dimethylformamide, DMSO for dimethyl sulfoxide, EDC for 1-(3-dimethylaminopropyl)-3-ethylcarbodiimide hydrochloride, Et$_2$O for diethyl ether, EtOAc for ethyl acetate, HATU for O-7-azabenwtriazol-1-yl)-N,N,N',N'-tetramethyluronium hexafluorophosphate, MeOH for methanol, iPrOH for isopropanol; TEA for triethylamine, AcOH for acetic acid, THF for tetrahydrofuran, Ac$_2$O for acetic anhydride, TFA for trifluoroacetic acid and petrol refers to petroleum ether, boiling point 40–60° C.

Solutions were dried over anhydrous sodium sulphate or potassium carbonate.

Intermediate 1

6-[(2-amino-ethyl)amino]-1-benzyl-1,4-dihydro-4-oxo-quinoline-3-carboxylic acid

To a solution of 1-Benzyl-6-chloro-1,4-dihydro-4-oxo-quinoline-3-carboxylic acid (300 mg) in 1-methyl-2-pyrrolidinone (6 mL) was added ethylenediamine (170 mg) under argon atmosphere. The mixture was heated at 120° C. for 18 h and then at 145° C. for 4 h. The reaction mixture was cooled and poured into water (12 mL). The pH value was adjusted with acetic acid to 7.0–7.5. The reaction mixture was extracted with DCM (5×30 mnL). The organic phase was dried over Na$_2$SO$_4$, filtered and concentrated under reduced pressure. The crude product was purified by silica SPE-column (eluent: from DCM 100% to DCM/MeOH/NH$_4$OH 85/13/2) giving the title compound (80 mg).

$^{13}$C-NMR (75 MHz, DMSO-d6) δ: 176.1; 165.4; 149.0, 138.1; 134.2; 133.5; 131.9; 129.8, 129.5, 129.2; 127.1; 126.4; 118.9; 58.3; 42.8; 42.2.

Intermediate 2

7-[(2-amino-ethyl)amino]-1-benzyl-1,4-dihydro-4-oxo-quinoline-3-carboxylic acid

To a solution of 7-chloro-1-benzyl-1,4-dihydro-4-oxo-quinoline-3-carboxylic acid (1.0 g) in 1-methyl-2-pyrrolidinone (10 mL) was added ethylenediamine (0.95 g). The mixture was heated at 130° C. for 10 h. The reaction mixture was cooled and poured into DCM (20 mL). The precipitate obtained was dispersed in MeOH, filtered to give the title compound (560 mg).

$^1$H-NMR (300 MHz, DMSO-d6) δ: 8.95 (s, 1H), 8.05 (d, 1H), 7.36 (m, 5H), 6.94 (d, 1H), 6.83 (m, 1H), 6.56 (s, 1H), 5.68 (s, 4H), 3.09 (m, 2H). $^{13}$C-NMR (75 MHz, DMSO-d6) δ: 176.3, 166.5, 153.6, 148.6, 142.3, 135.5, 128.7, 127.8, 126.8, 126.7, 114.5, 94.9, 56.3, 45.8.

Intermediate 3

7-[(2-amino-ethyl)amino]-1-ethyl-1,4-dihydro-4-oxo-quinoline-3-carboxylic acid

To a solution of 7-chloro-1-ethyl-4-oxo-1,4-dihydro-quinoline-3-carboxylic acid (1,7 g) in 1-methyl-2-pyrrolidinone (20 mL) was added ethylenediamine (2.1 g). The mixture was heated at 130° C. for 10 h. The reaction mixture was cooled and poured into DCM (20 mL). The precipitate obtained was dispersed in MeOH, filtered to give the title compound (830 mg).

MS; m/z (ES): 276 [MH]$^+$. $^1$H NMR (500 MHz, DMSO-d6) δ: 8.80 (s, 1H), 8.03 (d, 1H), 7.17 (m, 1H), 6.95 (dd, 1H), 6.65 (s, 1H), 4.46 (q, 2H), 3.28 (q, 2H), 2.84 (q, 2H), 1.40 (t, 3H). $^{13}$C-NMR (125 MHz, DMSO-d6) δ: 176.1, 166.8, 153.7, 147.8, 141.8, 126.9, 115.0, 106.5, 95.9, 48.5, 44.6, 39.9, 14.2.

Intermediate 4

7-[(2-amino-ethyl)amino]-1-cyclopropyl-1,4-dihydro-4-oxo-quinoline-3-carboxylic acid To a solution of 7-chloro-1-cyclopropyl-1,4-dihydro-4-oxo-quinoline-3-carboxylic acid (2.0 g) in 1-methyl-2-pyrrolidinone (20 mL) was added ethylenediamine (2.3 g). The mixture was heated at 130° C. for 10 h. The reaction mixture was cooled and poured into DCM (20 mL). The precipitate obtained was dispersed in MeOH, filtered to give the title compound (910 mg).

$^1$H-NMR (500 MHz, DMSO-d6) δ: 8.41 (s, 1H), 7.89 (d, 1H), 7.15 (m, 1H), 6.88 (s, 1H), 6.84 (dd, 1H), 6.56 (s, 1H), 3.56 (m, 1H), 3.16 (m, 2H), 2.75 (t, 2H), 1.17 (m, 2H), 1.01 (m, 2H). $^{13}$C-NMR (125 MHz, DMSO-d6) δ: 176.1, 166.5, 153.6, 147.1, 143.7, 126.7, 114.3, 106.1, 44.5, 39.7, 35.3, 7.4.

Intermediate 5 and Intermediate 6

6-[(2-aminoethyl)amino]-7-chloro-1,4-dihydro-1-ethyl-4-oxo-quinoline-3-carboxylic acid (5) and 7-[(2-amino-ethyl)amino]-1,4-dihydro-1-ethyl-6-fluoro-4-oxo-quinoline-3-carboxylic acid (6)

7-Chloro-1,4-dihydro-1-ethyl-6-fluoro-4-oxo-quinoline-3-carboxylic acid (250 mg) was dissolved in N,N-dimethylacetamide (5 mL) and ethylenediamine (223 mg) was added. The reaction mixture was stirred for 10 h at 100° C., then left overnight at room temperature and heated again at 100° C. for 7 h. Water (5 mL) was added and the resulting precipitate was filtered, washed with water (5 mL) and dried to give a mixture containing the title compounds (120 mg).

MS; m/z (ES): 310.2 [MH]$^+$ (intermediate 5), 294.2 [MH]$^+$ (intermediate 6).

Intermediate 7 and Intermediate 8

6-[(2-amino-ethyl)amino]-7-chloro-1-cyclopropyl-1,4-dihydro-4-oxo-quinoline-3-carboxylic acid hydrochloride (7) and 7-[(2-amino-ethyl)amino]-1-cyclopropyl-1,4-dihydro-6-fluoro-4-oxo-quinoline-3-carboxylic acid hydrochloride (8)

7-Chloro-1-cyclopropyl-1,4-dihydro-6-fluoro-4-oxo-quinoline-3-carboxylic acid (56.3 g) and ethylenediamine (36 g) were dissolved in N,N-dimethylacetamide (650 mL) at 100° C. and stirred for 8.5 h at 115° C. Water (700 mL) was added to the reaction mixture cooled at room temperature. The reaction mixture was stirred at room temperature for 2 h, cooled at 0–5° C. and stirred for 1 h. The precipitate obtained was filtered, washed with cold water, cold EtOH, and dried at 110° C. under reduced pressure for 1 h. The crude product was treated with HCl (6% aqueous solution) heating for 1 h in the presence of charcoal. After filtration, the solution was cooled to 35–40° C. and a first precipitation happened. The precipitate was filtered, washed with water and dried at 110° C. for 1 h. The title compound 7 (6.4 g) was obtained as hydrochloride salt. The mother liquors, after first precipitation, were cooled at room temperature and stirred overnight. The precipitate was filtered, washed with water and dried at 110° C. for 1 h to give a mixture containing the title compounds 7 and 8 (14.18 g). Where necessary, the hydrochloride salts were converted to the corresponding free bases before use using standard conditions.

Intermediate 7

$^1$H-NMR (300 MHz, CF$_3$COOD) δ: 8.94 (s, 1H), 8.40 (s, 1H), 7.40 (s, 1H), 3.85 (m, 1H), 3.76 (m, 2H), 5.45 (m, 2H), 1.42 (m, 2H), 1.77 (m, 2H).

Intermediate 9

7-[(2-amino-butyl)amino]-1-cyclopropyl-1,4-dihydro-4-oxo-quinoline-3-carboxylic acid To a solution of 7-chloro-1-cyclopropyl-1,4-dihydro-4-oxo-quinoline-3-carboxylic acid (1.0 g) in 1-methyl-2-pyrrolidinone (10 mL) was added butylenediamine (1.7 g). The mixture was heated at 130° C. for 16 h. The reaction mixture was cooled and poured into DCM (20 mL). The precipitate obtained was dispersed in MeOH and filtered to give the title compound (450 mg).

MS; (ES) m/z: 316.4 [MH]$^+$.

Intermediate 10

6-[(2-amino-ethyl)amino]-3-carboxyquinoline-7-chloro-1-cylopropyl-1,4-dihydro-4-oxo methyl ester.

A suspension of intermediate 7 (120 mg) in a solution of HCl in MeOH (3%, 30 mL) was sonicated in ultrasonic water bath at 60° C. for 3 h and then at room temperature for 48 h. The solvent was evaporated under reduced pressure and the crude product was purified by flash chromatography (eluent: MeOH/DCM/NH$_4$OH 9/5/0.5. affording the title compound (80 mg).

$^1$H-NMR (300 MHz, DMSO-d6) δ: 8.37 (s, 1H), 8.04 (s, 1H), 7.36 (s, 1H), 5.77 (t, 1H), 3.37 (s, 3H, O-Me), 3.64 (m, 1H), 3.20 (q, 2H), 2.85 (t, 2H), 1.23 (m, 2H), 1.08 (m, 2H).

Intermediates 11 and 12

6-[(3-terbutoxycarbonylaminopropyl)amino]-7-chloro 1-cyclopropyl-1,4-dihydro-4-oxo-quinoline-3-carboxylic acid (11) and 7-[(3-terbutoxycarbonylaminopropyl)amino]-1-cyclopropyl-1,4-dihydro-6-fluoro-4-oxo-quinoline-3-carboxylic acid (12)

In a sealed tube 1-N-tert-butoxycarbonyl)-3-propanediamine (5 mL) was added to a solution of 7-chloro-1-cyclopropyl-1,4-dihydro-6-fluoro-4-oxoquinoline-3-carboxylic acid (3 g) in DMSO (6 mL). The reaction mixture was stirred at 110° C. for 15 h. The reaction mixture was allowed to cool at 50° C. and was poured into ice, acetic acid was added to reach pH=5. A precipitate appeared and was separated by filtration and washed with ether to afford a mixture of 11 and 12 as a yellow solid (4.4 g). The mixture was purified by flash chromatography (eluent: from EtOAc/cyclohexane/AcOH 80/15/5 to EtOAc/AcOH 90/10) affording the title compound 11 (801 mg) and the title compound 12 (780 mg).

Intermediate 13

6-[(3-aminopropyl)amino]-7-chloro-1-cyclopropyl-1,4-dihydro-4-oxo-quinoline-3-carboxylic acid A solution of intermediate 11 (100 mg) in 10% TFA/DCM (1 mL) was stirred at room temperature for 2 h. The solvent was partially evaporated under reduced pressure. For five times the residual was diluted in DCM (2 mL) and concentrated under reduced pressure. Final solvent evaporation afforded the title compound (103 mg).

MS; m/z (ES): 336 [MH]$^+$. $^1$H-NMR (500 MHz, DMSO) δ: 8.56 (s, 1H), 8.22 (s, 1H), 7.35 (s, 1H), 6.54 (bt, 1H), 3.82 (m, 1H), 2.69 (t, 2H), 2.49 (m, 2H), 1.71 (m, 2H), 1.28 (m, 2H), 1.16 (m, 2H).

Intermediate 14

7-[(3-aminopropyl)amino]-1-cyclopropyl-1,4-dihydro-6-fluoro-4-oxo-quinoline-3-carboxylic acid A solution of intermediate 12 (100 mg) in 10% TFA/DCM (1 mL) was stirred at room temperature for 2 h. The solvent was partially evaporated under reduced pressure. For five times the residual was diluted in DCM (2 mL) and concentrated under reduced pressure. Final solvent evaporation afforded the title compound (103.4 mg).

MS; m/z (ES): 320 [MH]$^+$. H-NMR (500 MHz, DMSO) δ: 8.56 (s, 1H), 7.78 (d, 1H), 7.31 (bm, 1H), 7.15 (d, 1H), 3.72 (m, 1H), 2.70 (t, 2H), 2.50 (m, 2H), 1.74 (m, 2H), 1.29 (m, 2H), 1.15 (m, 2H).

Intermediates 13 and 14 (Mixture)

6-[(3-aminopropyl)amino]-7-chloro-1-cyclopropyl-1,4-dihydro-4-oxo-quinoline-3-carboxylic acid and 7-[(3-aminopropyl)amino]-1-cyclopropyl-1,4-dihydro-6-fluoro-4-oxo-quinoline-3-carboxylic acid To a solution of 7-chloro-1-cyclopropyl-1,4-dihydro-6-fluoro-4-oxo-quinoline-3-carboxylic acid (300 mg) in DMSO (1 mL), N-(tert-butoxycarbonyl)-3-propanediamine (0.37 mL) was added and the mixture was stirred at 110° C. for 3 h. The reaction was diluted with DCM (3 mL), washed with water (3×50 mL), dried over Na$_2$SO$_4$, filtered and concentrated under reduced pressure. The crude product was dissolved in HCOOH (5 mL) and stirred at room temperature for 12 h. The solvent was removed in vacuo, the crude product was washed several times with DCM (3×50 mL) and Et$_2$O (1×50 mL) and each time the solvent was evaporated under reduced pressure. The crude product obtained was purified by SCX cartridge (eluent:DCM followed by MeOH and by NH$_3$ (0.2 N in MeOH)) affording the mixture of the title compounds (180 mg).

Intermediate 15 and Intermediate 16

6-[(2-tertbutoxycarbonylaminoethyl)amino]-7-chloro-1-cyclopropyl-1,4-dihydro-4-oxo-quinoline-3-carboxylic acid (15)

and 7-[(2-tertbutoxycarbonylaminoethyl)amino]-1-cyclopropyl-1,4-dihydro-6-fluoro-4-oxo-quinoline-3-carboxylic acid (16)

In a sealed tube N-(tert-butoxycarbonyl)ethylenediamine (5 mL) was added to a solution of 7-chloro-1-cyclopropyl-6-fluoro-4-oxo-1,4-dihydro-quinoline-3-carboxylic acid (3 g) in DMSO (6 mL). The reaction mixture was stirred at 110° C. for 15 h. The reaction mixture was allowed to cool at 50° C. and was poured into ice, acetic acid was added to reach pH=5. A precipitate appeared and was separated by filtration and washed with ether to afford a 40:60 mixture of title compounds (4.4 g).

Intermediate 17 and Intermediate 18

6-[(2-tertbutoxycarbonylaminoethyl)amino]-7-chloro-1-cyclopropyl-1,4-dihydro-4-oxo-quinoline-3-carboxylic acid amide (17)

and 7-[(2-tertbutoxycarbonylaminoethyl)amino]-1-cyclopropyl-1-dihydro-6-fluoro-4-oxo-quinoline-3-carboxylic acid amide (18)

To a solution of a 40:60 mixture of intermediates 15 and 16 (1 g) in anhydrous DCM (20 mL) and anhydrous THF (30 mL) at −5° C. was added N-methylmorpholine (0.56 mL) followed by dropwise addition of isobutylchloroformate (0.64 mL). The reaction mixture was stirred for 1 h at room temperature and NH$_4$OH (33%, 20 mL) was added. The reaction mixture was concentrated under reduced pressure and an aqueous saturated solution of NH$_4$Cl (20 mL) was added. The obtained mixture was extracted with DCM (3×20 mL), the combined organic phase was dried over Na$_2$SO$_4$, filtered and concentrated under reduced pressure. The crude product was purified by flash chromatography (eluent DCM/MeOH from 99:1 to 95:5) affording a 40:60 mixture of title compounds (528 mg).

Intermediate 19 and Intermediate 20

6-[(2-aminoethyl)amino]-7-chloro-1-cyclopropyl-1,4-dihydro-4-oxo-quinoline-3-carboxylic acid amide-trifluoroacetic acid salt (19)

and 7-[(2-aminoethyl)amino]-1-cyclopropyl-1,4-dihydro-6-fluoro-4-oxo-quinoline-3-carboxylic acid amide-trifluoroacetic acid salt (20)

A 40:60 mixture of intermediates 17 and 18 (528 mg) was dissolved in a TFA solution (30 mL, 10% in DCM) and the reaction mixture was stirred at room temperature overnight. The reaction mixture was concentrated under reduced pressure to afford a 40:60 mixture of title compounds (544 mg).

HPLC/MS analysis (mobile phase: A/B from 95/5 to 10/90 in 10 min, 10/90 for 5 min, mass range 100–800 amu): retention time: 6.19 min (321 [MH]$^+$) and 5.63, (305 [MH]$^+$).

Intermediate 21

2'-acetyl-8a-aza-8a-homoerythromycin A

To a solution of 8a-aza-8a-homoerythromycin A (2.0 g) in DCM (100 mL) NaHCO$_3$ (900 mg) and Ac$_2$O (0.280 mL) were added. The resulting solution was stirred overnight at room temperature. To this mixture brine (100 mL) and water (50 mL) were added. The organic layer was separated, washed with brine (50 mL), dried over Na$_2$SO$_4$, filtered and evaporated under reduced pressure to afford the title compound (2.1 g).

MS; m/z (ES): 791.1 [MH]$^+$.

Intermediate 22

2'-O-acetyl-4''-O-propenoyl-8a-aza-8a-homoerythromycin A

Intermediate 21 (290 mg) was dissolved in toluene (10 mL) and the solvent was evaporated. This operation was repeated 2 times. The residue was dissolved again in toluene (15 mL) and the solution was stirred under argon. TEA (0.470 mL) was added followed by 3-chloropropionyl chloride (0.101 mL) added in three portions over a period of 10 minutes. After 15 h TEA (0.235 mL) and 3-chloropropionyl chloride (0.050 mL) were added. Three h later TEA (0.170 mL) and 3-chloropropionyl chloride (0.025 mL) were added. After one h a saturated aqueous solution of NaHCO$_3$ (30 mL) was added and the aqueous phase was extracted with toluene (3×20 mL). The organic phase was dried over Na$_2$SO$_4$, filtered and concentrated under reduced pressure to afford the title compound (261 mg).

Intermediate 23

4"-O-propenoyl-8a-aza-8a-homoerythromycin A

Intermediate 22 (225 mg) was dissolved in MeOH (30 mL) and stirred overnight. The solvent was evaporated under reduced pressure affording the title compound (221 mg).

MS; m/z (ES): 803.7 [MH]$^+$.

Intermediate 24

2'-O-acetyl-6-O-methyl-8a-aza-8a-homoerythromycin A

To a solution of 6-O-Methyl 8a-aza-8a-homoerythromycin A (1.62 g) in DCM (100 mL), NaHCO$_3$ (713 mg), and Ac$_2$O (0.230 mL) were added and stirred overnight. To this mixture brine (100 mL) and water (50 mL) were added. The organic layer was separated, washed with brine (50 mL), dried over Na$_2$SO$_4$ filtered and evaporated under reduced pressure affording the title compound (1.67 g).

MS; m/z (ES): 805.1 [MH$^+$.

Intermediate 25

2'-O-acetyl-4"-O-propenoyl-6-O-methyl-8a-aza-8a-homocrythromycin A

To a solution of intermediate 24 (1.80 g) in dry toluene (30 mL), under an argon atmosphere, was added TEA (2.90 mL) in one portion. To the reaction mixture was added 3-chloropropionyl chloride (0.63 mL) during several minutes. The reaction mixture was stirred for 2 h. Two more equivalents of TEA and one equivalent of 3-chloropropionyl chloride were added to the reaction solution and stirred for additional 2 h. The reaction was quenched via addition saturated NaHCO$_3$ (60 mL). The layers were separated and aqueous layer was extracted with toluene (3×30 mL). The combined toluene extracts were washed with brine (20 mL) dried over K$_2$CO$_3$, filtered and concentrated under reduced pressure affording the title compound (1.8 g).

MS; m/z (ES): 859 [MH]$^+$.

Intermediate 26

4"-O-propenoyl-6-O-methyl-8a-aza-8a-homoerythromycin A

The intermediate 25 (1.8 g) was dissolved in MeOH (100 mL) and the solution was stirred at room temperature for 24 h and then at 60° C. for 2 h. The solvent was removed under reduced pressure and the residue was purified by flash chromatography (eluent MeOH/DCM/NH$_4$OH 5/90/0.5) affording the title compound (1.54 g).

MS; m/z (ES): 817.5 [MH]$^+$.

Intermediate 27 and Intermediate 28

6-O-ethyl-8a-aza-8a-homoerythromycin A (27) and 6-O-ethyl-9a-aza-9a-homoerythromycin A (28)

To a suspension of 6-O-ethylerythromycin A 9(E)- and 9(Z)-oximes (3.76 g) in acetone and water (230 mL, mixture 1/1) at 0° C. was added NaHCO$_3$ (5.69 g). A solution of p-toluenesulphonyl chloride (6.46 g) in acetone (55 mL) was added dropwise for 30 min and the resulting suspension was stirred for 15 h at room temperature. Acetone was evaporated under reduced pressure, DCM (100 mL) and H$_2$O (100 mL) were added. The pH of the resulting solution was adjusted to 9.5 with NaOH (2M). The organic layer was separated and washed with brine (50 mL), dried over K$_2$CO$_3$, filtered and the filtrate was concentrated under reduced pressure. The residue was purified by flash chromatography (eluent: ethyl-acetate/n-hexane/diethylamine 6/3/0.2) affording the title compound 27 (0.835 g) and the title compound 28 (1.38 g).

MS; m/z (ES): 777.5 [MH]$^+$.

Intermediate 29

2'-O-acetyl-6-O-ethyl-8a-aza-8a-homoerythromycin A

To a solution of intermediate 27 (735 mg) in DCM (20 mL), NaHCO$_3$ (358 mg) and acetic anhydride (0.098 mL) were added stirring at room temperature for 20 h. Saturated solution of NaHCO$_3$ (20 mL) was added, water layer was washed with DCM (2×10 mL), organic layer was washed with brine (20 mL) dried over K$_2$CO$_3$, filtered and the filtrate was concentrated under reduced pressure, affording the title compound (661 mg).

MS; m/z (ES): 819.4 [MH]$^+$.

Intermediate 30

2'-O-acetyl-6-O-ethyl-4"-O-propenoyl-8a-aza-homoerythromycin A

To a solution of intermediate 29 (149 mg) in dry toluene (5 mL) under nitrogen atmosphere TEA (0.229 mL) was added at room temperature, then 3-chloropropionyl chloride (0.05 mL) was added in three portions during 3 h. A saturated solution of NaHCO$_3$ (5 mL) was added, water layer was washed with toluene (2×5 mL), organic layer was washed with brine (10 mL), dried over K$_2$CO$_3$, filtered and the filtrate was concentrated under reduced pressure, affording the title compound (139 mg).

MS m/z (ES) 873.4 [MH]$^+$.

Intermediate 31 and Intermediate 32

6-O-(2-propenyl)-8a-aza-8a-homoerythromycin A (31) and 6-O-(2-propenyl)-9a-aza-9a-homoerythromycin A (32)

To a suspension of 6-O-2-propenyl-erythromycin A 9(E)- and 9(Z)-oximes (4.25 g) in acetone/water 1/1 (250 mL) cooled to 0° C. NaHCO$_3$ (6.34 g) was added. Then a solution of p toluenesulphonyl chloride (7.19 g) in acetone (55 mL) was added dropwise in 30 min and the resulting suspension was stirred for 15 h allowing to rise to room temperature. Acetone was evaporated under reduced pressure and DCM (100 mL) and water (100 mL) were added. The pH of the solution was adjusted to 9.5 by addition of NaOH (2M). The organic layer was washed with brine (50 mL), dried over K$_2$CO$_3$ filtered and evaporated under reduced pressure. The residue was purified by flash chromatography (eluent: EtOAc/n-hexane/Et$_2$NH 6/3/0.2) affording the title compound 31 (2.36 g) and the title compound 32 (0.97 g).

MS; m/z (ES): 789.4 [MH]$^+$.

Intermediate 33

6-O-propyl-8a-aza-8a-homoerythromycin A

A solution of intermediate 31 (2.3 g) in MeOH (40 mL) was acidified to pH 5–5.5 using HCl (1M). Then 10% Pd/C (0.82 g) was added and the mixture was hydrogenated at 20 bar for 20 h. MeOH was evaporated under reduced presure, then DCM (50 mL) and water (50 mL) were added. The pH was adjusted to 9.5 using NaOH (1M). The aqueous phase was extracted with DCM (10 mL) and the organic layer was washed with brine (50 mL), dried over K$_2$CO$_3$, filtered and evaporated under reduced pressure affording the title compound (1.84 g).

MS; m/z (ES): 791.4 [MH]$^+$.

Intermediate 34

2'-O-acetyl-6-O-propyl-8a-aza-8a-homoerythromycin A

To a solution of intermediate 33 (0.27 g) in DCM (10 mL), NaHCO$_3$ (131 mg) and acetic anhydride (0.039 mL) were added at room temperature. The resulting suspension was stirred at room temperature for 20 h. A saturated solution of NaHCO$_3$ (10 mL) was added, and the aqueous layer was extracted with DCM (2×10 mL). The organic phase was washed with brine (10 mL), dried over K$_2$CO$_3$, filtered, and evaporated under reduced pressure affording the title compound (0.25 g).

MS; m/z (ES): 833.4 [MH]$^+$.

Intermediate 35

2'-O-acetyl-4''-O-propenoyl-6-O-propyl-8a-aza-8a-homoerythromycin A

To a solution of intermediate 34 (149 mg) in dry toluene (5 mL) at room temperature, under nitrogen atmosphere TEA (0.229 mL) was added, then 3-chloropropionyl chloride (0.052 mL) was added in three portions every hour and then stirred for 2 h. A saturated solution of NaHCO$_3$ (5 mL) was added and the aqueous phase was washed with toluene (2×5 mL). The organic solution was washed with brine (10 mL), dried over K$_2$CO$_3$ filtered, and the filtrate was evaporated under reduced pressure affording the title compound (139 mg).

MS; m/z (ES): 887.5 [MH]$^+$.

Intermediate 36

2'-O-acetyl-11,12-carbonate-11,12-dideoxy-4''-O-(1H-1-imidazolylcarbonyl)-6-O-methyl-8a-aza-8a-homocrythromycin A A solution of intermediate 24 (2.0 g) in dry DMF (20 mL) was cooled to 0° C. in an ice-water bath, under argon atmosphere. Then 1,1'-carbonyldiimidazole (3.20 g) was added in one portion, followed by portionwise addition of NaH (60% oil suspension, 0.47 g). The resulting mixture was stirred under argon atmosphere at 0° C. for 1 h. The reaction was quenched by dropwise addition of cold water (100 mL) during which a solid material precipitated. The solid was filtered and dried to give the title compound (2.02 g).

MS; m/z (ES): 925.9 [MH]$^+$.

Intermediate 37

2'-O-acetyl-4''-O-trimethylsilyl-8a-aza-8a-homoerythromycin A

Intermediate 21 (1.0 g) was dissolved in DCM (10 mL) and cooled to 0–5° C., then pyridine (0.31 mL) and trimethylsilylchloride (0.33 mL) were added and the resulting mixture stirred for 2 h. The reaction mixture was washed with an aqueous solution of NaH$_2$PO$_4$ (30 mL), with water (30 mL) and brine (30 mL), and the solvent concentrated under reduced pressure affording the title compound (0.94 g).

MS; m/z (ES): 862 [MH]$^+$.

Intermediate 38

11-O-[3-(3-quinolyl)-2-propenyl]-8a-aza-8a-homoerythromycin A

The intermediate 37 (0.9 g) and cis-propenylquinolyl t-butyl carbonate (0.630 g) were dissolved in toluene (18 mL) then the solvent was removed under reduced pressure. This operation was repeated twice, then the residue was dissolved in toluene (25 mL) and approximately 7 mL of solvent was removed in vacuo. The residual solution was transferred to a three-neck round-bottom flask and deoxygenated with argon. Tris(dibenzylideneacetone)dipalladium (0) (40 mg) and 1,4-Bis(diphenylphosphino)butane (37 mg) were added and the mixture heated at 80° C. for 1 h. The solvent was removed under reduced pressure. The residue was dissolved in MeOH (200 mL), formic acid was added adjusting the pH to 5 and the solution stirred overnight. The mixture was evaporated under reduced pressure to give a crude product that was purified by flash chromatography (eluent: CHCl$_3$/MeOH/NH$_4$OH 6/1/0.1) affording the title compound (260 mg).

MS; m/z (ES): 917 [MH]$^+$.

Intermediate 39

2'-O-acetyl-11-O-[3-(3-quinolyl)-2-propenyl]-8a-aza-8a-homoerythromycin A

To a solution of intermediate 38 (0.30 g) NaHCO$_3$ (900 mg) and Ac$_2$O (0.280 mL) were added at room temperature. The resulting solution was stirred overnight. To this mixture brine (100 mL) and water (50 mL) were added. The organic layer was separated, washed with brine (50 mL), dried, filtered and evaporated under reduced pressure affording the title compound (0.30 g).

MS; m/z (ES): 958 [MH]$^+$.

Intermediate 40

4''-O-propenyl-11-O-[3-(3-quinolyl-2-propenyl]-8a-aza-8a-homoerythromycin A

To a solution of intermediate 39 in dry toluene (5 mL), TEA (0.26 mL) and 3-chloropropionyl chloride (0.070 mL) were added. The reaction mixture was stirred for 0.5 h then quenched by addition of a saturated aqueous solution of sodium bicarbonate (15 mL). The aqueous phase was extracted with toluene (10 mL). The combined toluene extracts were washed with brine (20 mL), dried over potassium carbonate filtered and concentrated under reduced pressure. The crude product was dissolved in MeOH (60 mL) and stirred at room temperature for 24 h. The solvent was evaporated to give the title compound (0.25 g).

MS; m/z (ES): 971 [MH]$^+$.

Intermediate 41

2'-O-acetyl-6-O-methyl-9a-aza-9a-homoerythromycin A

To a solution of 6-O-methyl-9a-aza-9a-homoerythromycin A (4.0 g) in DCM (60 mL) and acetone (10 mL) NaHCO$_3$ (2.2 g) and Ac$_2$O (1.5 mL) were added. The reaction mixture was stirred for 1 h then DCM (75 mL) and water (75 mL) were added. The organic phase was separated, washed with brine (50 mL), dried over Na$_2$SO$_4$, filtered and evaporated under reduced pressure affording the title compound (4.02 g).

Intermediate 42

2'-O-acetyl-4''-O-propenyl-6-O-methyl-9a-aza-9a-homoerythromycin A

To a solution of intermediate 41 (3.0 g) in dry toluene (30 mL), was added TEA (2.07 mL) under argon atmosphere. The reaction mixture was cooled to 15° C. and 3-chloropropionyl chloride (0.71 mL), was added dropwise. The water bath was removed and the reaction mixture was stirred for 2 h, then TEA (1 mL) and 3-chloropropionyl chloride (0.48 mL) were added and the reaction solution was stirred for additional 2 h. A saturated aqueous solution of NaHCO$_3$ (60 mL), and EtOAc (30 mL), were added and the aqueous phase was extracted with EtOAc (2×30 mL). The combined organic extracts were dried over K₂CO₃, filtered and concentrated under reduced pressure affording of the title compound (3.17 g).

MS; m/z (ES): 859 [MH]⁺.

Intermediate 43

4″-propenoyl-6-O-methyl-9a-aza-9a-homoethromycin A

Intermediate 42 (2.9 g), was dissolved in MeOH (100 mL) and the solution was stirred at room temperature for 24 h then at 60° C. for 2 h. The solvent was evaporated and the residue was purified by flash chromatography (eluent: MeOH/DCM/NH₄OH 5/90/0.5) affording the title compound (1.8 g).

MS; m/z (ES): 817 [MH]⁺.

Intermediate 44

2′-O-acetyl-6-O-ethyl-9a-aza-9a-homoerythromycin A

To a solution of intermediate 28 (1.33 g) in DCM (30 mL) at room temperature, NaHCO₃ (650 mg) and Ac₂O (0.178 mL) were added. The resulting suspension was stirred at room temperature for 20 h. A saturated aqueous solution of NaHCO₃ (20 mL) was added, the aqueous phase was extracted with DCM (2×20 mL), and the combined organic solution was washed with brine (20 mL), dried over K₂CO₃, filtered and evaporated under reduced pressure affording the title compound (1.29 g).

MS; m/z (ES): 819.4 [MH]⁺.

Intermediate 45

2′-acetyl-4″-O-propenoyl-6-O-ethyl-8a-aza-8a-homoerythromycin A

To a solution of intermediate 44 (0.21 g) in dry toluene (5 mL) at room temperature, under nitrogen atmosphere, TEA (0.321 mL), was added. Then 3-chloropropionyl chloride (0.073 mL) was added in three portions over three hour and then stirred for 2 h. A saturated solution of NaHCO₃ (5 mL) was added and the aqueous phase was washed with toluene (2×10 mL). The organic solution was washed with brine (10 mL), dried over K₂CO₃, filtered, and evaporated under reduced pressure affording the title compound (0.20 g).

MS; m/z (ES): 873.4 [MH]⁺.

Intermediate 46

6-O-propyl-9a-aza-9a-homoerythromycin A

To a solution of intermediate 32 (1.27 g) in MeOH (40 mL), an aqueous solution of HCl (1M) was added until pH=5–5.5 was obtained. To the solution 10% Pd/C (0.45 g) was added and the mixture was hydrogenated at 15 bars for 20 h. The solution was concentrated under reduced presure and DCM (50 mL) and water (50 mL) were added. The pH of the resulting mixture was adjusted to 9.5 by addition of NaOH (1M). The aqueous phase was washed with of DCM (30 mL), and the organic solutions were combined and washed with brine (50 mL), dried over K₂CO₃ and evaporated under reduced pressure affording the title compound (0.97 g).

MS; m/z (ES): 791.4 [MH]⁺.

Intermediate 47

2′-O-acetyl-6-O-propyl-9a-aza-9a-homoerythromycin A

To a solution of intermediate 46 (0.97 mg) in DCM (50 mL) at room temperature were added NaHCO₃ (0.46 g) and Ac₂O (0.139 mL). The resulting suspension was stirred at room temperature for 20 h. An aqueous saturated solution of NaHCO₃ (50 mL) was added, and extracted with DCM (2×20 mL). The combined organic solution was washed with brine (40 mL), dried over K₂CO₃, filtered and evaporated under reduced pressure affording the title compound (0.95 g).

MS; m/z (ES): 833.4 [MH]⁺.

Intermediate 48

2′-O-acetyl-4″-O-propenoyl-6-O-propyl-8a-aza-8a-homoerythromycin A

To a solution of intermediate 47 (0.95 g) in dry toluene (25 mL) at room temperature, under nitrogen atmosphere triethylamine (0.958 mL) was added, then 3-chloropropionyl chloride (0.218 mL) was added in three portions every hour and then stirred for 2 h. An aqueous saturated solution of NaHCO₃ (25 mL) was added and the aqueous phase was washed with toluene (2×25 mL). The organic phase was washed with brine (50 mL), dried over K₂CO₃ filtered, and evaporated under reduced pressure affording the title compound (0.92 g).

MS; m/z (ES): 887.4 [MH]⁺.

Intermediate 49

2′-O-acetyl-11,12-carbonate-11,12-dideoxy-4″-O-propenoyl-azithromycin

A solution of intermediate 2′-O-acetyl-11,12-carbonate-11,12-dideoxy-azithromycin (10.9 g) in toluene (300 mL) was stirred at room temperature under argon atmosphere. To this solution TEA (12.66 mL) and 3-chloro-propionyl chloride (1.94 mL) were added in two portions over a period of 10 minutes. After 20 minutes the solution was diluted with a saturated aqueous solution of NaHCO₃ (300 mL) and extracted with toluene (4×80 mL). The collected organic phase was dried, filtered and concentrated under reduced pressure affording the title compound (11.0 g).

MS; m/z (ES): 872 [MH]⁺.

Intermediate 50

11,12-carbonate-11,12-dideoxy-4″-O-propenoyl azithromycin

A solution of intermediate 49 (11.0 g) in MeOH (200 mL) was stirred at room temperature for 48 h. The solvent was evaporated under reduced pressure affording the title compound (9.81 g).

MS; m/z (ES): 829.1 [MH]⁺. ¹H-NMR (500 MHz,) δ: 6.45 (d, 1H), 6.17 (dd, 1H), 5.87 (d, 1H), 5.11 (d, 1H), 4.88 (dd, 1H), 4.77 (d, 1H), 4.53 (d, 1H), 4.47–4.40 (m, 3H), 3.72 (m, 1H), 3.60 (d, 1H), 3.33 (s, 3H), 3.25 (dd, 1H), 2.87–2.85 (m, 2H), 2.58 (m, 1H), 2.44–2.38 (m, 2H), 2.32 (s, 6H), 2.21 (s, 3H), 2.06 (m, 1H), 2.00 (m, 1H), 1.92 (m, 1H), 1.84 (m, 1H), 170–1.56 (m, 4H), 1.45 (s, 3H), 1.40 (dd, 1H), 1.29 (s, 3H), 1.25 (m, 1H), 1.22 (d, 3H), 1.18 (d, 6H), 1.12 (s, 3H), 108–1.06 (2d, 6H), 0.93 (m, 6H).

Intermediate 51

4″-O-propenoyl-azithromycin

To a solution of intermediate 50 (1.3 g) in acetonitrile (50 mL), a saturated aqueous solution of potassium carbonate (30 mL) was added at room temperature. The resulting mixture was heated to 70° C. for 8 h. The mixture was then diluted with water (100 mL), extracted with EtOAc (4×30 mL). The collected organic phase was dried, filtered and concentrated under reduced pressure. The crude product was purified by flash chromatography (eluent: DCM/MeOH/NH₃ 90/9/0.5) affording the title compound (530 mg).

MS; m/z (ES): 804 [MH]⁺.

Intermediate 52

2'-O-acetyl-4"-O-imidazolylcarbonyl azithromycin

To a solution of 2'-O-acetyl azithromycin (0.8 g) in dry toluene (30 mL) under an argon atmosphere $K_2CO_3$ (420 m), and 1,1'-carbonyldiimidazole (0.170 g) were added. The reaction mixture was stirred at RT for 20 h, and at 40° C. for additional 5 h. A saturated solution of $NaHCO_3$ (30 mL) was added and the aqueous phase was washed with toluene (2×30 mL). The combined organic solution was dried over $K_2CO_3$ and concentrated under reduced pressure affording the title compound (0.82 g)

MS; m/z (ES): 885 [MH]$^+$.

Intermediate 53

2'-O-acetyl-6-O-methyl-azithromycin

To a solution of 6-O-methyl-azithromycin (205 mg) in DCM (10 mL), $NaHCO_3$ (112.8 mg) and $Ac_2O$ (0.030 mL) were added. The mixture was stirred at room temperature for 20 h, then brine (20 mL) was added. The solution was extracted with DCM and the organic phase was dried. The solvent was concentrated under reduced pressure affording the title compound (220 mg).

MS; m/z (ES): 805 [MH]$^+$.

Intermediate 54

4"-O-propenoyl-6-O-methyl-azithromycin

A solution of intermediate 53 (215 mg) in DCM (10 mL) was stirred under argon atmosphere for 10 min. TEA (0.222 mL) and 3-chloro-propionylchloride (0.051 mL) were added in two portions. 15 min later again TEA (0.111 mL) and 3-chloro-propionylchloride (0.026 mL) were added. 12 h later TEA (0.111 mL) and 3-chloro-propionylchloride (0.026 mL) were added. The reaction mixture was stirred at room temperature for 2 h. A saturated aqueous solution of $NaHCO_3$ (20 mL) was added. The layers were separated and the organic phase was dried. The solvent was concentrated under reduced pressure and the residue (240 mg) was dissolved in MeOH (20 mL) and stirred at room temperature for 14 h. The solvent was concentrated under reduced pressure affording the title compound (220 mg).

MS; m/z (ES): 817.6 [MH]$^+$.

Intermediate 55

2'-O-acetyl-11,12-(aminocarbonyloxy)-11,12-dideoxy-4-O-methyl-erythromycin A

To a solution of 11,12-(aminocarbonyloxy)-11,12-dideoxy-6-O-methyl-erythromycin A in DCM (50 mL) was added $NaHCO_3$ (478 mg) at room temperature. To this solution $Ac_2O$ (0.153 mL) was added and stirred overnight. To this mixture brine (50 mL) and water (20 mL) were added. The organic layer was separated, washed with brine (20 mL), dried, filtered and evaporated under reduced pressure, affording the title compound (1.2 g).

MS; m/z(ES): 816.2 [MH]$^+$.

Intermediate 56

2'-O-acetyl-11,12-(aminocarbonyloxy)-11,12-dideoxy-6-O-methyl-4"-O-propenoyl-erythromycin A

Intermediate 55 was dissolved in toluene (50 mL) and the solvent was evaporated. This was performed 2 times. After that the residue was again dissolved in toluene (45 mL) and stirred under argon. To this solution TEA (1.8 mL) and 3-chloropropionylchloride (0.40 mL) (in 3 portions in a period of 20 minutes) were added. 20 min later a saturated aqueous solution of $NaHCO_3$ (50 mL) was added. The aqueous solution was extracted with toluene (3×50 mL), the combined organic solution dried over $K_2CO_3$ and the solvent removed under reduced pressure affording the title compound (1.04 g).

MS; m/z (ES): 870.1 [MH]$^+$.

Intermediate 57

11,12-(aminocarbonyloxy)-11,12-dideoxy-6-O-methyl-4"-O-propenoyl-erythromycin A

A solution of intermediate 56 in McOH (30 mL) was stirred at room temperature overnight. The solvent was concentrated under reduced pressure affording the title compound (1.2 g).

MS; m/z (ES): 828.1 [MH]$^+$. $^1$H-NMR (500 MHz) δ: 6.44 (d, 1H), 6.13 (dd, 1H), 5.89 (d, 1H), 5.11 (dd, 1H), 4.98 (d, 1H), 4.75 (d, 1H), 4.60 (d, 1H), 4.36 (m, 1H), 3.80 (d, 1H), 3.73 (m, 1H), 3.70 (s, 1H), 3.62 (d, 1H), 3.34 (m, 1H), 3.32 (s, 3H), 3.22 (m, 1H), 2.95 (s, 3H). $^{13}$C-NMR (125 MHz) δ: 218.4; 176.9; 166.2; 158.8; 132.0; 128.4; 102.5; 96.2; 84.3; 80.7; 79.1; 78.8; 77.8; 76.1; 73.2; 71.4; 68.2; 65.83; 63.6; 58.2; 58.2; 50.6; 49.9; 45.6; 45.5; 41.1; 40.7; 40.0; 39.9; 37.8; 35.5; 22.4; 21.9; 21.4; 20.1; 18.6; 18.5; 16.1; 14.1; 13.6; 10.8; 9.5.

Intermediate 58

2'-O-acetyl-11,12-dideoxy-6-O-methyl-11,12-(methylaminocarbonloxy)-erythromycin A

11,12-dideoxy-6-O-methyl-11,12-(methylaminocarbonyloxy)erythromycin A (0.87 g) was dissolved in DCM (20 mL) and acetone (3 mL). Solid $NaHCO_3$ (0.6 g) and $Ac_2O$ (0.6 mL) were added and the reaction mixture was stirred for 1 h, then DCM (50 mL) and water (50 mL) were added. The organic phase was separated, washed with brine (20 mL), dried over $K_2CO_3$, filtered and concentrated under reduced pressure, affording the title compound (0.875 g).

MS; m/z (ES): 829.2 [MH]$^+$.

Intermediate 59

11,12-dideoxy-6-O-methyl-11,12-(methylaminocarbonyloxy)-4"-O-propenoyl-erythromycin A

To a solution of intermediate 58 (0.85 g) in dry toluene (10 mL) under argon atmosphere, TEA (0.85 mL) and 3-chloropropionyl chloride (0.196 mL, in 2 portions over a period of 20 minutes) were added and the reaction mixture was stirred for 1 h. Then a saturated solution of $NaHCO_3$ (30 mL) was added and the mixture was extracted with toluene (2×60 mL). The combined organic solution was washed with brine (20 mL) dried over $K_2CO_3$, filtered and concentrated under reduced pressure. The residue was dissolved in MeOH (70 mL) and heated at 60° C. for 4 h then allowed to stand at room temperature for 24 h. The solvent was concentrated under reduced pressure affording the title compound (620 mg).

MS; m/z (ES): 841 [MH]$^+$. $^1$H-NMR (300 MHz) δ: 6.44 (d, 1H), 6.13 (dd, 1H), 5.90 (d, 1H), 4.97 (m, 2H), 4.75 (d, 1H), 4.60 (d, 1H), 4.36 (m, 1H), 3.77 (m, 3H), 3.64 (d, 1H), 3.55 (s, 1H).

Intermediate 60

2'-O,4"-O-diacetyl-11-deoxy-10,11-didehydro-12-O-(1H-1-imidazolcarbonyl)-6-O-methyl-erythromycin A

A solution of 2'-O, 4"-O-diacetyl-6-O-methyl-erythromycin A (4.0 g) was dissolved in DMF (20 mL) at 0° C. under argon atmosphere and N,N-carbonyldiimidazole (1.6 g) was added. Then NaH (1.2 g, 50% suspension in oil) was added portionwise in a period of 30 min. The reaction mixture was stirred for 4 h then H$_2$O (60 mL) was added. The precipitate was filtered, washed with water and dried, affording the title compound (4.1 g).

Intermediate 61

2'-O,4"-O-diacetyl-11,12-dideoxy-11,12-(ethylaminocarbonyloxy)-6-O-methyl-erythromycin A Intermediate 60 (3.5 g) was dissolved in CH$_3$CN (35 mL) and H$_2$O (4 mL) at room temperature and the reaction solution was cooled to 0° C. in an ice-water bath, under an argon atmosphere. EtNH$_2$ (1.7 g) was added and the reaction mixture was stirred for 20 h. Water (50 mL) was added and the precipitate was filtered, washed with water and dried, affording the title compound (2.6 g).

Intermediate 62

11,12-dideoxy-11,12-ethylaminocarbonyloxy)-6-O-methyl-erythromycin A

Intermediate 61 (2.5 g) was dissolved in MeOH (140 mL) and a saturated aqueous solution of K$_2$CO$_3$ (10 mL) was added and the reaction mixture was stirred at 75° C. for 4 h and at room temperature overnight. The volume of the solution was halved under reduced pressure and EtOAc (100 mL) and water (50 mL) were added to the residue. The organic layer was separated, dried and evaporated to afford the title compound (2.4 g).

Intermediate 63

2'-O-acetyl-11,12-dideoxy-11,12-(ethylaminocarbonyloxy)-6-O-methyl-erythromycin A Intermediate 62 (1.5 g) was dissolved in DCM (40 mL) and acetone (5 mL). Solid NaHCO$_3$ (1.2 g) and Ac$_2$O (0.8 mL) were added and the mixture was stirred for 1 h. Then DCM (60 mL) and water (60 mL) were added and the organic phase was separated, washed with brine (20 mL), dried and evaporated affording the title compound (1.5 g).

MS; m/z (ES): 843.2 [MH]$^+$.

Intermediate 64

11,12-dideoxy-11,12-(ethylaminocarbonyloxy)-6-O-methyl-4"-O-propenoyl-erythromycin A To a solution of intermediate 63 (1.45 g) in dry toluene (17 mL) under argon atmosphere TEA (1.42 mL) and 3-chloropropionyl chloride (0.49 mL, in 3 portions in a period of 20 minutes) were added. The reaction mixture was stirred for 1 h, then a saturated solution of NaHCO$_3$ (50 mL) was added and the aqueous phase was extracted with toluene (2×70 mL). The combined organic solution ws washed with brine (20 mL), dried over K$_2$CO$_3$, filtered and concentrated under reduced pressure. The residue was dissolved in MeOH (100 mL) and heated at 60° C. for 4 h then at room temperature for 24 h. The solvent was evaporated and the crude product was purified by flash chromatography (eluent: MeOH/DCM/NH$_4$OH 5/90/0.5) affording the title compound (1.4 g).

MS; m/z (ES): 855 [MH]$^+$. $^1$H-NMR (500 MHz) δ: 6.44 (d, 1H), 6.13 (dd, 1H), 5.89 (d, 1H), 4.99 (m, 2H), 4.75 (d, 1H), 4.60 (d, 1H), 4.38 (m, 1H), 3.77–3.55 (m, 6H), 3.32 (s, 3H), 3.20 (m, 1H), 3.06 (m, 1H), 3.05 (s, 3H), 2.95 (m, 1H), 2.61–2.52 (m, 2H), 2.43 (d, 1H), 2.31 (s, 6H), 1.98–1.89 (m, 2H), 1.73 (d, 1H), 1.68–1.64 (m, 2H), 1.55–1.49 (m, 1H), 1.39 (s, 3H), (d, 1H),1.38 (s, 3H), 1.25–1.12 (m), 1.02 (d, 3H), 0.84 (t, 3H). $^{13}$C-NMR (125 MHz) δ: 216.1; 176.3; 165.8; 157.2; 131.5; 128.0; 102.2; 96.0; 82.6; 79.8; 78.7; 77.6; 76.1; 75.9; 73.7; 71.1; 67.9; 65.3; 63.2; 60.0; 50.5; 49.5; 45.6; 45.1; 40.3; 38.9; 38.8; 38.7; 38.6; 35.2; 28.8; 21.9; 21.7; 21.0; 20.1; 18.9; 18.6; 18.3; 15.9; 14.2; 14.1; 12.7; 10.3; 9.1.

Intermediate 65

2'-O-acetyl-11,12-dideoxy-11,12-(N-(4-phenylbutyl)amino)carbonyloxy]-6-O-methyl-erythromycin A To a solution of 11,12-dideoxy-11,12-[(N-(4-phenylbutyl)amino)carbonyloxy]-6-O-methyl-erythromycin A (0.550 g) in DCM (17 mL), acetic anhydride (0.101 mL) and NaHCO$_3$ (0.140 g) were added. The mixture was stirred at room temperature for 24 h then a saturated solution of NaHCO$_3$ (25 mL) was added. The organic phase was separated, washed with brine (15 mL) and water (15 mL) dried and evaporated affording the title compound (0.530 g).

MS; m/z (ES): 904 [MH]$^+$.

Intermediate 66

2'-O-acetyl-11,12-dideoxy-11,12-[(N-(4-phenylbutyl)amino)carbonyloxy]-6O-methyl-4"-O-Propenoyl-erythromycin A To a solution of intermediate 65 (0.500 g) in dry toluene (8 mL) under argon atmosphere, TEA (0.440 mL) and 3-chloropropionyl chloride (0.116 mL) were added in two portions. The reaction mixture was stirred at room temperature for 0.5 h. A saturated solution of NaHCO$_3$ (25 mL) was added, and the aqueous phase was extracted with toluene (2×10 mL). The combined organic extracts were washed with brine (25 mL), dried over K$_2$CO$_3$ filtered and concentrated under reduced pressure affording the title compound (0.450 g).

Intermediate 67

11,12-dideoxy-11,12-[(N-(4-phenylbutyl)amino)carbonyloxyl-6-O-methyl-4"-O-propenoyl-erythromycin A Intermediate 66 (0.450 g) was stirred in MeOH (110 mL) at room temperature for 48 h. Evaporation under reduced pressure gave the title compound (0.420 g).

MS; m/z (ES): 959 [H]$^+$.

Intermediate 68

2'-O-acetyl-6-O-methyl-4"-propenoyl-erythromycin A

To a solution of 2'-O-acetyl-6-O-methylerythromycin A (1.1 g) in DCM (20 mL) pyridine (1.7 mL) and acryloylchloride (1.1 mL) were added at 0° C. After 2 h a further addition of pyridine (1.7 mL) and of acryloylchloride (1.1 mL) was performed. The reaction mixture was quenched with a saturated solution of NH$_4$Cl (10 mL) and extracted with DCM (3×20 mL). The organic phase was washed with a saturated solution of NaHCO$_3$ (10 mL), water (10 mL), dried over Na$_2$SO$_4$, filtered and evaporated under reduced pressure. The crude product was purified by flash-chromatography (DCM/MeOH/NH$_3$ 95/5/0.5) affording the title compound (470 mg).

Intermediate 69

6-O-methyl-4"-propenoyl-erythromycin A

Intermediate 68 (1.82 g, mmol) was dissolved in MeOH (100 mL) and stirred at 60° C. for 4 h, then at room temperature for 16 h. The solvent was evaporated under reduced pressure and the crude product was purified by flash chromatography (eluent: MeOH/DCM/NH$_4$OH 5/90/0) affording the title compound (1.4 g).

MS; m/z (ES): 802 [MH]$^+$. $^1$H-NMR (500 MHz) δ: 6.44 (d, 1H), 6.13 (dd, 1H), 5.89 (d, 1H), 5.07 (d, 1H), 5.00 (d, 1H), 4.75 (d, 1H), 4.60 (d, 1H), 4.38 (m, 1H), 3.97 (s, 1H), 3.80–3.73 (m, 2m), 3.66 (d, 1H), 3.46 (s, 1H), 3.32 (s, 3H), 3.21–3.18 (m, 2H), 3.04 (s, 3 H), 3.00 (m, 1H), 2.92 (m, 1H), 2.56 (m, 2H), 2.43 (d, 1H), 2.31 (s, 6H). $^{13}$C-NMR (75 MHz) δ: 221.0; 175.7; 165.8; 131.5; 128.0; 102.1; 96.0; 80.5, 78.8, 78.3; 78.0; 76.6; 74.3, 72.7; 71.1; 69.1; 67.8; 65.3; 63.2; 50.7; 49.5; 45.3; 44.9; 40.3; 39.2; 38.8; 37.2; 35.2; 28.9; 21.7, 21.1; 19.7, 18.3, 18.0, 15.9; 12.3; 10.6; 9.1.

Intermediate 70

2-O-acetyl-4''-O-iodoethanoyl-6-O-methyl-erythromycin A

To a solution of 2'-O-acetyl-6-O-methyl-erythromycin A (600 mg) in anhydrous DCM (40 mL), pyridine (0.18 mL) and chloroacetyl chloride (0.06 mL) were added and the reaction mixture was stirred at room temperature for 15 min. A second addition of pyridine (0.18 mL) and chloroacetyl chloride (0.06 mL) was performed. After further 15 min a third addition of pyridine (0.18 mL) and chloroacetyl chloride (0.06 mL) was performed followed by a fourth addition of pyridine (0.18 mL) and chloroacetyl chloride (0.06 mL) after further 30 min. The reaction mixture was further stirred for 1 h, then brine was added (20 mL). The aqueous phase was extracted with DCM (3×20 mL) and the combined organic layers were washed with a saturated aqueous solution of NaHCO$_3$ (20 mL). The organic phase was dried, filtered and concentrated under reduced pressure. To the crude product dissolved in acetone (4 mL), a solution of sodium iodide (570 mg) in acetone (6 mL), was added. The reaction mixture was then stirred at room temperature for 1 h, filtered and the filtrate concentrated under reduced pressure. The crude product was dissolved in EtOAc (10 mL), water (10 mL) was added and the aqueous phase was extracted with EtOAc (3×10 mL). The combined organic layers were washed with a saturated aqueous solution of Na$_2$S$_2$O$_5$ (10 mL), dried, filtered and concentrated under reduced pressure affording the title compound (546 mg).

$^1$H-NMR (500 MHz) δ: 5.00 (d, 1H), 4.81 (bt, 1H), 4.74 (d, 1H), 4.66 (d, 1H), 4.34 (m, 1H), 3.76 (m, 1H), 3.71 (d+d, 2H), 3.37 (s, 3H), 2.40 (d, 1H), 2.10 (s, 3H), 1.67 (m, 2H), 1.32 (m, 1H), 1.24 (d, 3H), 1.13 (d, 3H).

Intermediate 71

6-O-propyl-erythromycin A

To a solution of 6-O-(2-propenyl)erythromycin A (2.5 g) in MeOH (60 mL), Pd/C (10%, 0.85 g) was added and the mixture was hydrogenated at room temperature at 15 bar for 20 h.

The catalyst was filtered and washed with MeOH and the solvent was evaporated under reduced pressure. DCM (50 mL) and water (50 mL) were added and the pH was adjusted to 9.5 by addition of NaOH (1M). The organic phase was dried over K$_2$CO$_3$, filtered and evaporated under reduced pressure affording the title compound (2.27 g).

MS; m/z (ES): 776.6 [MH]$^+$.

Intermediate 72

2'-O-acetyl-6-O-propyl-erythromycin A

To a solution of intermediate 71 (1.0 g) in DCM (30 mL), NaHCO$_3$ (0.487 g) and Ac$_2$O (0.134 mL) were added at room temperature. The solution was stirred for 24 h then water (20 mL) was added and the pH was adjusted to 9.5 by addition of NaOH (1M), organic layer was dried over K$_2$CO$_3$, filtered and evaporated under reduced pressure affording the title compound (1.0 g).

MS; m/z (ES): 818.6 [MH]$^+$.

Intermediate 73

2'-O-acetyl-4''-O-propenoyl-6-O-propyl-erythromycin A

Intermediate 72 (1.0 g) was dissolved in dry toluene (40 mL) under N$_2$, TEA (0.513 mL) and 3-chloropropionyl chloride (0.116 mL) were added and the solution was stirred for 30 minutes. Additional amounts of TEA (0.513 mL) and 3-chloropropionyl chloride (0.116 mL) were added after a 1 h and after 2 h. The reaction mixture was quenched by addition of a saturated aqueous solution of NaHCO$_3$ (30 mL), the organic layer was washed with brine, dried over K$_2$CO$_3$, filtered and concentrated under reduced pressure to give the title compound (1.01 g).

Intermediate 74

4'-O-propenyl-6-O-propyl-erythromycin A

The intermediate 73 (1.01 g) was dissolved in MeOH (50 mL) and was stirred at room temperature for 20 h. The solvent was removed under reduce pressure and DCM (50 mL) and water (30 mL) were added. The pH was adjusted at 9.5 by addition of NaOH (1M) and the organic phase was dried over K$_2$CO$_3$, filtered and evaporated under reduced pressure affording the title compound (0.92 g).

MS; m/z (ES): 830.6 [MH]$^+$.

Intermediate 75

11,12-carbonate-2',4''-O-diacetyl-11,12-dideoxy-6-O-methyl-erthromycin A

To a solution of 2',4''-O-diacetyl-6-O-methyl-erythromycin A (200 g) in anhydrous DCM (1.6 L), pyridine (117 mL) and a solution of triphosgene (71.2 g) in DCM (400 mL) were added at 0° C. under a nitrogen atmosphere. The resulting mixture was stirred at 0° C. for 30 min and then at room temperature for 15 h. The mixture was then diluted with water (750 mL) and extracted with DCM (2×500 mL). The organic phase was washed with water (3×300 mL), dried, filtered and evaporated under reduced pressure to give the title compound (200 g).

MS; m/z (ES): 858 [MH]$^+$.

Intermediate 76

11-deoxy-2',4''-O-diacetyl-10,11-didehydro-6-O-methyl-erythromycin A

To a solution of intermediate 75 (50.5 g) in 2/1 mixture of anhydrous toluene/EtOAc (675 mL), DBU (9.24 mL) was added at room temperature. The resulting mixture was heated to 85° C. for 8 h. A further addition of DBU (4.4 mL) was performed and the reaction mixture was stirred at room temperature for 5 h. The mixture was then diluted with brine (250 mL), extracted with EtOAc (2×350 mL) dried, filtered. Solvent evaporation of under reduced pressure and crystallisation from acetone/water gave the title compound (46 g).

MS; m/z (ES): 814 [MH]$^+$.

Intermediate 77

12-chloroethanoyl-11-deoxy-2',4''-O-diacetyl-10,11-didehydro-6-O-methyl-erythromycin A To a solution of intermediate 76 (20 g) in anhydrous DCM (340 mL) at 0° C., pyridine (6 mL) and chloroacetic anhydride (8.4 g) were added and the reaction mixture was allowed to reach room temperature. After 16 h the reaction mixture was washed with water (300 mL) the organic phase was firstly washed with a saturated aqueous solution of NH$_4$Cl (150 mL) and then with brine (150 mL). The combined aqueous phase was extracted with DCM (2×300 mL). The organic phase was dried, filtered and evaporated under reduced pressure. The crude product was precipitated from acetone/water affording the title compound (20.4 g).

MS; m/z (ES): 890 [MH]$^+$.

Intermediate 78

(11S,11aR)-11-(carboxycyanomethyl)-11-deoxy-2',4"-O-di-acetyl-6-O-methyl-erthromycin A Intermediate 77 (27.4 g) was dissolved in anhydrous DMF (275 mL) and potassium cyanide (5 g) was added. The mixture was stirred at room temperature for 4.5 h, quenched with a saturated aqueous solution of NaHCO$_3$ (250 mL) and extracted with DCM (3×300 mL). The organic phase was dried over Na$_2$SO$_4$, filtered and concentrated under reduced pressure. The residue was dissolved in acetone (100 mL) and the compound was precipitated by addition of water (250 mL). Filtration afforded the title compound (25.8 g).

MS; m/z (ES): 881 [MH]$^+$.

Intermediate 79

(11S,11aR)-11-(carboxycyanomethyl)-11-deoxy-6-O-methyl-erythromycin A

To a solution of intermediate 78 (300 mg) in anhydrous MeOH (40 mL) was added an aqueous solution of lithium hydroxide (1M, 4 mL) and the reaction mixture was stirred at room temperature for 48 h. A solution of HCl (10% v/v) was slowly added to reach pH=8, the solvent was partially evaporated under reduced pressure. The solution was diluted with water (20 mL) and extracted with DCM (8×20 mL). The collected organic phase was dried, over Na$_2$SO$_4$, filtered and concentrated under reduced pressure. The crude product was purified by flash chromatography (eluent: DCM/MeOH 85/15) affording the title compound (150 mg).

MS; m/z (ES): 797 [MH]$^+$. TLC: MeOH/DCM 10/90 (Rf=0.23).

Intermediate 80

(11S,11aR)-2'-O-acetyl-11-(carboxycyanomethyl)-11-deoxy-6-O-methyl-erythromycin A To a solution of intermediate 79 (150 mg) in anhydrous DCM (20 mL) NaHCO$_3$ (48 mg) was added followed by acetic anhydride (0.020 mL). The reaction mixture was stirred at room temperature overnight. The NaHCO$_3$ was filtered off, the organic phase was washed with water (3×20 mL), the combined organic phase was dried, filtered and concentrated under reduced pressure yielding the title compound (0.145 g).

MS; m/z (ES): 839 [MH]$^+$. TLC: MeOH/DCM 5/95 (Rf=0.24).

Intermediate 81

(11S,11aR)-2'-O-acetyl-4"-O-propenoyl-11-(carboxycyanomethyl)-11-deoxy-6-O-methyl-erythromycin A To a solution of intermediate 80 (90 mg) in anhydrous DCM (10 mL) cooled to 0° C. pyridine (0.174 mL) was added followed by propenoyl chloride (0.174 mL). The reaction mixture was warmed to room temperature and stirred for 24 h, then washed with water (3×10 mL). The organic phase was then firstly washed with a saturated aqueous solution of NaHCO$_3$ (2×10 mL) and then with brine (2×10 mL). The combined aqueous phase was extracted with DCM (2×10 mL) and the combined organic phase was dried, filtered and concentrated under reduced pressure. The crude material was filtered trough a silica gel pad (eluent: DCM/MeOH 95/5) yielding the title compound (90 mg).

MS; m/z (ES): 893 [MH]$^+$. TLC: MeOH/DCM 5/95 (Rf=0.42).

Intermediate 82

2'-O-acetyl-roxithromycin

To a solution of roxithromycin (500 mg) and NaHCO$_3$ (150 mg) in anhydrous DCM (50 mL) acetic anhydride (0.062 mL) was added. The reaction mixture was stirred at room temperature overnight, filtered and the filtrate washed with water (3×20 mL). The combined aqueous phase was extracted with DCM (3×20 mL) and the combined organic phase was dried, filtered and concentrated under reduced pressure yielding the title compound (510 mg).

MS; m/z (ES): 879 [MH]$^+$. TLC: MeOH/DCM 5/95 (Rf=0.28).

Intermediate 83

2'-acetyl-4"-O-propenoyl-roxithromycin

To a solution of intermediate 82 (50 mg) in anhydrous toluene (10 mL), triethylamine (0.016 mL) and 3-chloropropionyl chloride (0.008 mL) were added. The reaction mixture was stirred at room temperature overnight. Water (3 mL) was added and the reaction mixture was extracted with EtOAc (3×10 mL). The combined organic phase was dried over Na$_2$SO$_4$, filtered and concentrated under reduced pressure. The crude material was filtered trough a silica gel pad (eluent: DCM/MeOH 95/5) yielding the title compound (49 mg).

MS; m/z (ES): 933 [MH]$^+$. TLC: MeOH/DCM 5/95 (Rf=0.36).

Intermediate 84

6-(2-amino-ethylamino)-7-chloro-1-cyclopropyl-1H-quinolin-4-one and 7-(2-amino-ethylamino)-1-cylopropyl-6-fluoro-1H-quinolin-4-one A solution of a 40:60 mixture of intermediates 15 and 16 (147 mg) in aqueous HCl (2 N, 5 mL) was heated at 100° C. for 4 days in a sealed tube. The reaction mixture was concentrated under reduced pressure. The crude product was purified by preparative TLC (eluent: DCM/MeOH/NH$_4$OH 90/10/1.5) to give the title compounds (23 mg, a 70/30 mixture of Cl/F derivatives).

$^1$H-NMR (500 MHz) δ for 6-(2-amino-ethylamino)-7-chloro-1-cyclopropyl-1H-quinolin-4-one 8.05 (s, 1H), 7.85 (d, 1H), 7.35 (s, 1H), 6.10 (d, 1H), 3.50–2.70 (m, 5H), 1.30–0.98 (m, 4H). $^1$H-NMR (500 MHz) δ for 7-(2-amino-ethylamino)-1-cyclopropyl-6-fluoro-1H-quinolin-4-one: 7.81 (d, 1H), 7.65 (d, 1H), 7.00 (d, 1H), 6.03 (d, 1H), 3.50–2.70 (m, 5H), 1.30–0.98 (m, 4H).

Intermediate 85

7-(2-amino-ethylamino)-1-cyclopropyl-6-fluoro-4-oxo-1,4-dihydro-quinoline-3-carboxylic acid methyl ester A suspension of intermediate 8 (2.0 g, 6.55 mmol) in 3% H$_2$SO$_4$ in MeOH (170 ml) was stirred at 60° C. for 48 h during which time the reaction mixture became a solution. The reaction solution was neutralised and the solvent was evaporated. The crude product was purified via flash chromatography on silica gel by using MeOH—CH$_2$Cl$_2$—NH$_4$OH=9–5–0.5 affording the title compound (720 mg).

Intermediate 86

7-[(2-aminobutyl)amino]-1-methyl-1,4-dihydro-4-oxo-3-quinolinecarboxylic acid

To a solution of 7-chloro-1-methyl-4-oxo-1,4-dihydro-3-quinoline carboxylic acid (1.0 g, prepared according to H. Agui and T. Nakagome, J. Heterocycl. Chem., (1979), 16(7), 1353–60) in 1-methyl-2-pyrrolidinone (10 mL), was added 1,4-diaminobutane (1.84 g). The mixture was heated at 130° C. for 17 hours. The reaction mixture was cooled and poured into DCM (20 mL). The precipitate obtained was dispersed in MeOH and filtered to give the title compound (860 mg).

MS (ES) m/z: [MH]$^+$ 290.3.

Intermediate 87

7-[(2-aminoethyl)amino]-1-methyl-4-oxo-1,4-dihydro-3-quinoline carboxylic acid

To a solution of 7-chloro-1-methyl-4-oxo-1,4-dihydro-3-quinoline carboxylic acid (1.5 g, prepared according to H. Agui and T. Nakagome, J. Heterocycl. Chem., (1979), 16(7), 1353–60) in 1-methyl-2-pyrrolidinone (15 mL), was added ethylenediamine (1.9 g). The mixture was heated at 130° C. for 24 hours. The reaction mixture was cooled and poured into DCM (20 mL). The precipitate obtained was dispersed in MeOH, filtered giving the title compound (500 mg).

MS (ES) m/z: [MH]$^+$ 262.3.

Intermediate 88

7-[(2-aminoethyl)amino]-1-cyclopropyl-1,4-dihydro-4-oxo-6-fluoro-8-methoxy-3-quinoline carboxylic acid To a solution of 1-cyclopropyl-1,4-dihydro-4-oxo-6,7-difluoro-8-methoxy-3-quinoline carboxylic acid (1.0 g) in N,N-dimethylacetamide (10 ml), N-BOC-ethylenediamine (0.82 mg) was added. The mixture was heated at 120° C. for 12 h. Trifluoracetic acid (20 ml) was added and the reaction mixture was stirred at r.t. for 24 h. The solvent was evaporated under reduced pressure. The crude product was dissolved in water (5 ml) and pH adjusted with 20% NaOH to 7. The precipitate obtained was dispersed in MeOH and filtered to give the title compound (1.01 g).

MS; m/z (ES): 336.0 [MH]$^+$.

EXAMPLE 1

4″-O-[3-[[2-[(3-carboxy-7-chloro-1-cyclopropyl-1,4-dihydro-4-oxo-6-quinolinyl)amino]ethyl]amino]propionyl]-8a-aza-8a-homoerythromycin A To a solution of intermediate 23 (20 mg) in CH$_3$CN (0.4 mL) was added intermediate 7 (16 mg). The resulting mixture was heated at 70° C. for 24 h. The solvent was concentrated under reduced pressure and the residue was purified by silica SPE-column using a gradient solvent system DCM/MeOH/NH$_4$OH affording the title compound (11 mg).

MS; m/z (ES): 1124.5 [MH]$^+$. $^1$H-NMR (500 MHz) δ: 8.73 (s, 1H), 8.05 (s, 1H), 7.53 (s, 1H), 5.86 (br.s, 1H), 5.31 (t, 1H), 5.12 (d, 1H), 4.91 (dd, 1H), 4.70 (d, 1H), 4.53 (d, 1H), 4.33 (m, 2H), 4.19 (m, 1H), 3.83 (m, 1H), 3.76–3.70 (m, 1H), 3.68–3.64 (m, 1H), 3.58–3.55 (m, 2H), 3.49 (s, 1H), 3.39 (m, 1H), 3.29 (s, 3H).

EXAMPLE 2

4″-O-[3-[[2-[(3-carboxy-1-cyclopropyl-1,4-dihydro-6-fluoro-4-oxo-7-quinolinyl)amino]ethyl]amino]propionyl]-8a-aza-8a-homoerythromycin A To a solution of intermediate 23 (20 mg), in MeOH (0.4 mL), intermediate 8 (36 mg) was added. The resulting mixture was heated at 70° C. in an ultrasonic bath for 60 h. The mixture was filtered and the filtrate evaporated under reduced pressure. The residue was purified by silica SPE-column (eluent: from DCM 100% to DCM/MeOH/NH$_4$OH 85/13/2) to afford the title compound (13.6 mg).

Ms (ES) m/z: 1108 [MH]$^+$.

EXAMPLE 3

4″-O-[3-[[2-[(3-carboxy-7-chloro-1-cyclopropyl-1,4-dihydro-4-oxo-6-quinolinyl)amino]ethyl]amino]propionyl]-6-O-methyl-8a-aza-8a-homoerythromycin A To a solution of intermediate 25 (5 g) in i-PrOH (40 mL) intermediate 7 (2.8 g) was added. Reaction mixture was stirred at 80° C. for 24 h. Excess of amine was filtered from the reaction mixture and MeOH (100 mL) was added. The reaction mixture was stirred for 4 days. Reaction mixture was filtered and evaporated under reduced pressure to give the crude product mixture (5.94 g). The crude product was purified by flash chromatography in gradient solvent system DCM/MeOH/NH$_4$OH to give the title compound (1.385 g).

MS; m/z (ES): 1139.8 [MH]$^+$. $^1$H-NMR (500 MHz) δ: 8.73 (s, 1H), 8.04 (s, 1H), 7.54 (s, 1H), 5.61 (d, 1H), 5.28 (t, 1H), 5.08 (d, 1H), 4.94 (dd, 1H), 4.70 (d, 1H), 4.50 (d, 1H), 4.37 (m, 1H), 4.19 (m, 1H), 3.98 (d, 1H), 3.71–3.66 (m, 2H), 3.58–3.54 (m, 1H), 3.50 (s, 1H), 3.38 (m, 1H), 3.31 (s, 3H). $^{13}$C-NMR (75 MHz) δ: 177.5; 177.2; 174.3; 172.3; 167.3; 145.8; 143.1; 132.5; 127.6; 126.3; 118.0; 107.6; 104.5; 102.6; 95.3; 80.1; 78.9; 78.8; 77.4; 74.2; 72.9; 70.8; 70.3; 68.2; 65.4; 62.8; 51.8; 49.5; 47.5; 45.5; 44.4; 43.0; 42.8; 42.4; 42.3; 40.9; 40.4; 35.3; 35.1; 34.7; 29.0; 23.9; 21.7; 21.6; 21.3; 21.2; 18.0; 16.1; 15.0; 11.2; 9.6; 9.3; 8.1.

EXAMPLE 4

4″-O-[3-[(2-[(3-carboxy-1-cyclopropyl-1,4-dihydro-6-fluoro-4-oxo-7-quinolinyl)amino]ethyl]amino]propionyl]-6-O-methyl-8a-aza-8a-homoerythromycin A To a solution of intermediate 26 (134 mg) in i-PrOH (2.5 mL) intermediate 8 was added (100 mg) and shaken at 85° C. for 14 days. The reaction mixture was cooled to room temperature and filtered through silica gel cartridge (2 g) eluting with DCM (10 mL). The solvent was evaporated to give 100 mg of crude residue that was purified by silica SPE-column in gradient solvent system DCM/MeOH/NH$_4$OH affording the title compound (9.3 mg).

MS; m/z (ES): 1122.3 [MH]$^+$.

EXAMPLE 5

4″-O-[3-[[2-[(7-chloro-1-cyclopropyl-1,4-dihydro-3-methoxycarbonyl-4-oxo-6-quinolinyl)amino]ethyl]amino]propionyl]-6-O-methyl-8a-aza-8a-homoerthromycin A To a solution of intermediate 25 (100 mg) in i-PrOH (1 mL) intermediate 10 (60 mg) was added. This mixture was heated at 70° C. for 18 h. The solvent was evaporated and the residue was dissolved in MeOH and stirred at room temperature for 24 h. The solvent was evaporated and the residue purified by silica gel SPE-column (eluent: from DCM 100% to DCM/MeOH/NH4OH 85/13/2) affording the title compound (62 mg).

MS; m/z (ES): 1152.6 [MH]$^+$.

EXAMPLE 6

4"-O-[3-[4-(3-carboxy-1-cyclopropyl-1,4-dihydro-6-fluoro-4-oxo-7-quinolinyl)-1-piperazinyl]propionyl]-6-O-methyl-8a-aza-8a-homoerythromycin A A mixture of intermediate 26 (100 mg) and 1-cyclopropyl-1,4-dihydro-6-fluoro-4-oxo-7-piperazinyl-quinoline-3-carboxylic acid (203 mg) in MeOH (20 mL) was stirred at 60° C. for 2 days, then at room temperature for 2 days and then at 60° C. for 24 h. Isocyanate polymer-bound (600 mg) and DCM (60 mL) were added and stirred at room temperature for 48 h. The suspension was filtered and washed with DCM (10 mL). The filtrate was concentrated under reduced pressure affording the title compound (150 mg).

MS; m/z (ES): 11.49.4 [MH]$^+$.

EXAMPLE 7

4"-O-[3-[4-(3-carboxy-1-cyclopropyl-1,4-dihydro-4-oxo-7-quinolinyl)piperazinyl]propionyl]-6-O-methyl-8a-aza-8a-homoerthromycin A According to the same procedure described for example 6, reaction of intermediate 26 (10 mg) and 1-cyclopropyl-4-oxo-7-piperazinyl-1,4-dihydro-quinoline-3-carboxylic acid (19 mg) afforded the title compound (4.2 mg).

MS; m/z(ES): 1131.6 [MH]$^+$.

EXAMPLE 8

4"-O-[3-[4-(1-cycloproyl-1,4-dihydro-6-fluoro-4-oxo-7-quinolinyl)-piperazinyl]propionyl]-6-O-methyl-8a-aza-8a-homoerythromycin A According to the same procedure described for example 6, reaction of intermediate 26 (10 mg) and 1-cyclopropyl-5-fluoro-4-oxo-7-piperazinyl-1,4-dihydro-4-quinolinone (18 mg) afforded the title compound (5.1 mg).

MS; m/z (ES): 1105.6 [MH]$^+$.

EXAMPLE 9

4"-O-[3-[4-(3-carboxy-7-chloro-1-cyclopropyl-1,4-dihydro-4-oxo-6-quinolinyl)-1-piperazinyl]propionyl]-6-O-methyl-8a-aza-8a-homoerythromycin A According to the same procedure described for example 6, reaction of intermediate 26 (10 mg) and 7-chloro-1-cyclopropyl-4-oxo-6-piperazinyl-1,4-dihydroquinolone-3-carboxylic acid (21 mg) afforded the title compound (4.8 mg).

MS; m/z (ES): 11 65.8 [MH]$^+$.

EXAMPLE 10

4"-O-[3-[(4-[(3-carboxy-1-cyclopropyl-1,4-dihydro-6-fluoro-4-oxo-7-quinolinyl)amino]butyl]amino]propionyl]-6-O-methyl-8a-aza-8a-homoerythromycin A To a solution of intermediate 26 (100 mg) in i-PrOH (2 mL), 7-((4-aminobutyl)amino)-1-cyclopropyl-1,4-dihydro-6-fluoro-4-oxo-quinoline-3-carboxylic acid (61 mg) was added and shaken at 70° C. for 2 days. The solvent was evaporated and the residue was purified by flash chromatography in gradient solvent system DCM/MeOH/NH$_4$OH to give the title compound (48 mg).

MS m/z (ES): 1150.9 [MH]$^+$.

EXAMPLE 11

4"-O-[3-[[3-[(3-carboxy-1-cyclopropyl-6-fluoro-1,4-dihydro-4-oxo-7-quinolinyl)amino]propyl]amino]propionyl]-6-O-methyl-8a-aza-8a-homoerythromycin A To a solution of intermediate 25 (10 mg) in i-PrOH (3 mL) was added intermediate 14 (17 mg) and the reaction mixture was heated at 70° C. for 42 h. The reaction mixture was filtered washing the solid with i-PrOH, the combined filtered were concentrated under reduced pressure and stirred in MeOH for 72 h. Solvent evaporation gave the crude product which was purified by prepatative TLC (eluent: MeOH/NH$_4$OH 97/3) affording the title compound (3.6 mg).

$^1$H-NMR (500 MHz) δ: 8.73 (s, 1H), 7.93 (d, 1H), 7.00 (bm, 1H), 6.91 (d, 1H), 5.60 (bd, 1H), 4.70 (d, 1H), 4.40 (m, 1H), 4.20 (m, 1H), 3.50 (m, 1H), 3.40 (m, 2H), 2.94–2.90 (m, 4H), 2.65 (m, 2H), 1.95 (m, 2H), 1.39 (m, 2H), 1.16 (m, 2H).

EXAMPLE 12

4"-O-[3-[[3-[(3-carboxy-7-chloro-1-cyclopropyl-1,4-dihydro-4-oxo-7-quinolinyl)amino]propyl]amino]propionyl]-6-O-methyl-8a-aza-8a-homoerythromycin A To a solution of intermediate 25 (10 mg) in i-PrOH (3 mL) was added intermediate 13 (20 mg) and the reaction mixture was heated at 70° C. for 42 h. The reaction mixture was filtered washing the solid with i-PrOH, the combined filtered were concentrated under reduced pressure and stirred in MeOH for 72 h. Solvent evaporation gave the crude product which was purified by prepatative TLC (eluent: MeOH/NH$_4$OH 97/3) affording the title compound (3.9 mg).

$^1$H-NMR (500 MHz) δ: 8.73 (s, 1H), 8.02 (s, 1H), 7.52 (s, 1H), 5.86 (bs, 1H), 5.59 (bd, 1H), 4.70 (d, 1H), 4.38 (m, 1H), 3.55 (m, 1H), 3.40 (m, 2H), 2.93 (m, 2H), 2.85 (m, 2H), 2.71–2.55 (m, 2H), 2.00 (m, 2H), 1.40 (m, 2H), 1.16 (m, 2H).

EXAMPLE 13

4"-O-[3-[(2-[(3-carboxy-1-cyclopropyl-1,4-dihydro-4-oxo-7-quinolinyl)amino]ethyl]amino]propionyl]-6-O-methyl-8a-aza-8a-homoerythromycin A To solution of intermediate 26 (100 mg) in i-PrOH (1 mL), intermediate 4 (105 mg) was added and shaken at 70° C. for 22 h. The solvent was evaporated, and the residue was triturated with DCM (2 mL). The resulting suspension was filtered and washed with DCM (1 mL). The filtrate was concentrated under reduced pressure. The crude product was precipitated from EtOAc/n-hexane affording the title compound (20 mg).

MS; m/z (ES): 1105.0 [MH]$^+$.

EXAMPLE 14

4"-O-[3-[[2-[(3-carboxy-1,4-dihydro-1-ethyl-4-oxo-7-quinolinyl)amino]ethyl]amino]propionyl]-6-O-methyl-8a-aza-8a-homoerythromycin A A solution of intermediate 26 (90 mg) and intermediate 3 (90 mg) in i-PrOH (1 mL) was heated at 70° C. for 20 h. The solvent was evaporated, the residue was triturated with DCM (2 mL). The resulting suspension was filtered and washed with DCM (1 mL). The mother liquor was concentrated under reduced pressure. The crude product was precipitated from EtOAcn-hexane affording the title compound (38 mg).
MS; m/z (ES): 1093.3 [MH]$^+$.

EXAMPLE 15

4"-O-[3-[4-(3-carboxy-1-ethyl-6-fluoro-1,4-dihydro-1,8]naphthyridinyl)-4-oxo-[1-piperazinyl]propionyl]-6-O-methyl-8a-aza-8a-homoerythromycin A To a solution of intermediate 25 (20 mg) in anhydrous MeOH (2 mL) 1-ethyl-6-fluoro-4-oxo-7-piperazin-1-yl-1,4-dihydro-[1,8]naphthyridine-3-carboxylic acid (22 mg) was added. The reaction mixture was stirred at 40° C. overnight, the solvent was evaporated and the residue dissolved in DCM (3 mL). Isocyanate polymer-bound resin was added and the mixture was shaken at room temperature overnight. The resin was filtered and washed with DCM (3 mL), MeOH (3 mL) and DCM (3 mL). The collected organic extracts were evaporated under reduced pressure. The residue was dissolved in DCM (5 mL) and washed with water (3×3 mL). The organic phase was dried, filtered and concentrated under reduced pressure. The crude material was purified by flash chromatography (eluent: DCM/MeOH 90/10) affording the title compound (18 mg).
$^1$H-NMR (500 MHz) δ: 15.0 (bs, 1H), 8.71 (s, 1H), 8.12 (d, 1H), 5.57 (bd, 1H), 4.72 (d, 1H), 4.41 (q, 2H), 4.39 (m, 1H), 4.19 (m, 1H), 3.85 (m, 4H), 2.83–2.55 (m, 4H), 2.64 (m, 4H), 1.51 (t, 3H).

EXAMPLE 16

4"-O-[3-[(2-[(1-benzyl-3-carboxy-1,4-dihydro-4-oxo-6-quinolinyl)amino]ethyl]amino]propiony]-6-methyl-8a-aza-8a-homoerythromycin A To a solution of intermediate 26 (80 mg) in i-PrOH (1.5 mL) was added intermediate 1 (49 mg). The resulting mixture was stirred at 70° C. for 18 h. DBU (0.04 mL) was added and the reaction mixture was stirred at 50° C. for additional 24 h. The solvent was evaporated under reduced pressure, and the crude product was purified by flash chromatography (eluent: MeOH/DCM/NH$_4$OH 9/90/1.5) affording the title compound (30 mg).
MS; m/z (ES): 1154.2 [MH]$^+$.

EXAMPLE 17

4"-O-[3-[[2-[(3-carboxy-7-chloro-1-cyclopropyl-1,4-dihydro-4-oxo-6-quinolinyl)amino]ethyl]amino]propionyl]-6-O-ethyl-8a-aza-8a-homoerythromycin A To a solution of intermediate 30 (139 mg) in MeOH (5 mL) was added intermediate 7 (102.5 mg) and stirred at 60° C. for 24 h. The reaction suspension was filtered, concentrated under reduced pressure and the residue purified by flash chromatography (eluent: DCM/MeOH/NH$_4$OH 9/1.3/0.2) affording the title compound (37 mg).
MS; m/z (ES): 1153.7 [MH]$^+$. $^{13}$C-NMR (500 MHz) (δ/ppm): 177.5, 175.2, 172.3, 167.4, 145.8, 143.1, 132.5, 127.6, 126.3, 118.0, 107.6, 104.5, 103.1, 97.4, 78.8, 78.7, 77.5, 74.1, 73.1, 71.0, 70.9, 68.6, 65.4, 62.9, 49.5, 47.5, 45.4, 44.5, 42.8, 42.5, 41.9, 41.8, 40.7, 40.4, 35.8, 35.4, 34.5, 23.2, 21.5, 21.4, 21.3, 17.5, 16.1, 15.4, 10.8, 10.5, 9.9, 8.1.

EXAMPLE 18

4"-O-[3-[[2-[(3-carboxy-7-chloro-1-cyclopropyl-1,4-dihydro-4-oxo-6-quinolinyl)amino]ethyl]amino]propionyl]-6-O-propyl-8a-aza-8a-homoerythromycin A To a solution of intermediate 48 (220 mg) in MeOH (5 mL) was added intermediate 7 (182 mg) stirred at 60° C. for 24 h. The reaction suspension was filtered, methanol was evaporated under reduced pressure and the residue was purified by flash chromatography (eluent: DCM/MeOH/NH4OH 85/13/2) affording the title compound (23 mg).
MS; m/z (ES): 1167.3 [MH]$^+$. $^{13}$C-NMR (500 MHz) (δ/ppm): 177.5, 175.1, 172.2, 167.4, 145.8, 143.1, 132.5, 127.7, 126.4, 118.0, 107.6, 104.4, 102.9, 97.3, 78.9, 78.7, 77.4, 74.2, 73.0, 71.1, 70.9, 68.5, 65.4, 62.9, 49.5, 47.5, 45.4, 44.5, 42.8, 42.5, 42.0, 40.7, 40.4, 35.8, 35.4, 34.6, 23.2, 21.6, 21.5, 21.4, 21.3, 17.6, 16.2, 16.0, 10.8, 10.5, 9.9, 8.1.

EXAMPLE 19

11,12-carbonate-4"-O-[[[2-[(3-carboxy-7-chloro-1-cyclopropyl-1,4-dihydro-4-oxo-6-quinolinyl)amino]ethyl]amino]carbonyl]-11,12-dideoxy-6-O-methyl-8a-aza-9a-homoerythromycin A To a solution of intermediate 36 (105 mg) in DMF intermediate 7 (73 mg) and DBU (0.2 mL) were added. The resulting mixture was stirred under argon atmosphere at 60° C. for 1 h. Then EtOAc (30 mL) and a saturated aqueous solution of NaHCO3 (30 mL) were added. The aqueous phase was washed with EtOAc (2×15 mL), and the organic solutions were combined, dried and concentrated under reduced pressure.

The crude residue was dissolved in MeOH (50 mL) and the solution was stirred overnight. The solvent was evaporated, and the crude product was purified by flash chromatography (eluent: MeOH/DCM/NH4OH 9/90/1.5) affording the title compound (80 mg).
$^1$H-NMR (500 MHz) δ: 8.73 (s, 1H), 8.06 (s, 1H), 7.49 (s, 1H), 6.22 (d, 1H), 5.40 (t, 1H), 5.32 (t, 1H), 5.03 (d, 1H), 4.93 (dd, 1H), 4.60 (d, 1H), 4.41 (d, 1H), 4.38 (d, 1H), 4.34 (m, 1H), 4.13 (m, 1H), 4.02 (m, 1H), 3.67–3.62 (m, 3H), 3.57–3.55 (m, 2H), 3.47–3.43 (m, 2H), 3.31 (s, 3H),3.18 (s, 3H). $^{13}$C-NMR (75 MHz) δ: 177.5; 176.4; 170.4; 167.3; 157.5; 153.3; 145.9; 142.9; 132.7; 127.5; 126.2; 118.1; 107.6; 103.9; 102.9; 96.1; 85.6; 82.2; 80.38; 79.7; 79.6; 75.4; 73.2; 70.7; 68.7; 65.3; 63.1; 51.1; 49.6; 45.8; 45.05; 42.6; 42.4; 42.0; 40.3; 39.8; 35.4; 29.1; 22.8; 22.5; 21.9; 21.3; 21.1; 17.7; 14.6; 14.0; 12.3; 11.0; 10.5; 8.1.

EXAMPLE 20

4"-O-[3-[[2-[(3-carboxy-7-chloro-1-cyclopropyl-4-oxo-1,4-dihydro-6-quinolinyl) amino]ethyl]amino] propionyl]-11-O-[3-(3-quinolyl)-2-propenyl]-8a-aza-8a-homoerythromycin A To a suspension of intermediate 40 (0.1 g) in i-PrOH (4 mL) intermediate 7 (0.2 g) was added. The resulting mixture was stirred at 80° C. for 3 days, then the solvent was evaporated and the residue was purified by flash chromatography (eluent: CHCl$_3$/MeOH/NH4OH 6/1/0.1) affording the title compound (45 mg).

MS; m/z (ES): 1291.9 [MH]$^+$.

EXAMPLE 21

4"-O-[3-[[2-[(3-carboxy-7-chloro-1-cyclopropyl-1,4-dihydro-4-oxo-6-quinolinyl)amino]ethyl]amino] propionyl]-6-O-methyl-9a-aza-9a-homoerythromycin A To a solution of intermediate 43 (200 mg) in i-PrOH (2 mL) was added intermediate 7 (125 mg) and shaken for 7 h at 70° C., then at 80° C. overnight. The reaction was filtered and the filtrate was evaporated under reduced pressure. The residue was purified by flash chromatography in gradient solvent system DCM/MeOH/NH$_4$OH to afford the title compound (48 mg).

MS; m/z (ES): 1139.8 [MH]+.

EXAMPLE 22

4"-O-[3-[[4-[(3-carboxy-1-cyclopropyl-1,4-dihydro-6-fluoro-4-oxo-7-quinolinyl)amino]butyl]amino] propionyl]-6-O-methyl-9a-aza-9a-homoerythromycin A To a solution of intermediate 43 (100 mg) in i-PrOH (2 mL), 7-((2-aminobutyl)amino)-1-cyclopropyl-1,4-dihydro-6-fluoro-4-oxoquinoline-3-carboxylic acid (122 mg) was added and shaken at 70° C. for 24 h. The solvent was concentrated under reduced pressure. The residue was purified by flash chromatography in gradient solvent system DCM/MeOH/NH$_4$OH affording the title compound (34 mg).

MS; m/z (ES): 1150 [MH]+.

EXAMPLE 23

4"-O-[3-[[2-[(3-carboxy-7-chloro-1-cyclopropyl-1,4-dihydro-4-oxo-6-quinolinyl)amino]ethyl]amino] propionyl]-6-O-ethyl-9a-aza-9a-homoerythromycin A To a solution of intermediate 45 (200 mg) in methanol (5 mL) intermediate 7 (148 mg) was added and stirred at 60° C. for 24 h. The reaction suspension was filtered, methanol was evaporated under reduced pressure and the residue was purified by flash chromatography (eluent: DCM/MeOH/NH4OH 9/1.3/0.2) affording the title compound (34 mg).

MS; m/z (ES): 1153.0 [MH]$^+$. $^{13}$C-NMR (500 MHz,) δ: 179.2, 177.1, 172.2, 167.4, 145.9, 143.1, 132.5, 127.6, 126.3, 118.0, 107.6, 104.5, 101.3, 96.1, 80.0, 79.0, 78.6, 77.7, 74.2, 73.8, 72.8, 71.3, 67.3, 65.0, 63.3, 58.9, 50.8, 49.4, 47.6, 45.6, 44.5, 42.8, 40.6, 40.4, 39.8, 35.4, 35.2, 34.7, 34.3, 21.7, 21.3, 20.8, 20.7, 18.6, 18.3, 16.4, 16.1, 15.9, 11.2, 9.7, 8.1.

EXAMPLE 24

4"-O-[3-[[2-[(3-carboxy-7-chloro-1-cyclopropyl-1,4-dihydro-4-oxo-6-quinolinyl)-amino]ethyl]amino] propionyl]-6-O-propyl-9a-aza-9a-homoerythromycin A To a solution of intermediate 48 (100 mg) in methanol (5 mL) intermediate 7 (73 mg) was added and stirred at 60° C. for 24 h. The reaction suspension was filtered, and the solvent was evaporated under reduced pressure. The residue was purified by flash chromatography (eluent: DCM/MeOH/NH4OH 9/1.3/0.2) affording the title compound (10 mg).

MS; m/z (ES): 1167.3 [MH]$^+$.

EXAMPLE 25

11,12-carbonate-4"-O-[3-[[2-[(3-carboxy-7-chloro-1-cyclopropyl-1,4-dihydro-4-oxo-6-quinolinyl)amino] ethyl]amino]propionyl]-11,12-dideoxy-azithromycin To a suspension of intermediate 50 (1.0 g) in i-PrH (45 mL) intermediate 7 (2.0 g) was added. This mixture was heated at 70° C. for 48 h. The solvent was evaporated and the residue purified by flash chromatography (eluent: CHCl$_3$/MeOH/NH$_3$ 6/1/0.1) affording the title compound (120 mg).

MS; m/z (ES): 1151 [MH]$^+$. $^1$H-NMR (500 MHz) δ: 8.72 □s, 1H), 8.04 (s, 1H), 7.52 (s, 1H), 5.10 (d, 1H), 4.87 (dd, 1H), 4.72 (d, 1H), 4.48 (d, 1H), 4.44–4.37 (m, 3H), 3.70 (m, 1H), 3.58 (d, 1H), 3.31 (s, 3H), 3.27 (m, 1H), 2.87–2.84 (m, 2H), 2.67–2.55 (m, 3H), 2.44–2.36 (m, 8H), 2.21 (s, 3H), 2.07 (m, 1H), 2.00 (m, 1H), 1.92 (m, 1H), 1.87–1.79 (m, 2H), 1.68–1.55 (m, 3H), 1.45 (s, 3H).

EXAMPLE 26

11,12-carbonate-4"-O-[3-[[2-[(3-carboxy-1-cyclopropyl-1,4-dihydro-6-fluoro-4-oxo-7-quinolinyl) amino]ethyl]amino]propiony]-11,12-dideoxy azithromycin To a suspension of intermediate 50 (1.0 g) in i-PrOH (45 mL) intermediate 8 (2.0 g) was added. This mixture was heated at 70° C. for 48 h. The solvent was evaporated and the residue was purified by flash chromatography (eluent: CHCl$_3$/MeOH/NH$_3$ 6/1/0.1) affording the title compound (150 mg).

MS; m/z (ES): 1135 [MH]$^+$.

EXAMPLE 27

11,12-carbonate-4"-O-[3-[[2-[(3-carboxy-1-cyclopropyl-1,4-dihydro-4-oxo-7-quinolinyl)amino] ethyl]-amino]propiony]-11,12-dideoxy-azithromycin To a suspension of intermediate 50 (200 mg) in MeOH (2 mL) intermediate 4 (210 mg) was added. This mixture was heated at 70° C. for 20 h. The solvent was removed under reduced pressure then DCM (10 mL) was added and the precipitate was filtered off. The organic phase was evaporated under reduced pressure and the residue purified by flash chromatography (eluent: CHCl$_3$/MeOH/NH$_3$ 6/1/0.1) affording the title compound (55 mg).

MS; m/z: (ES): 1117 [MH]$^+$. $^1$H-NMR (500 MHz) δ: 8.56 (s, 1H), 8.11 (d, 1H), 6.88 (s, 1H), 6.81 (d, 1H), 5.12 (d, 1H), 4.88 (dd, 1H), 4.73 (d, 1H), 4.47–4.41 (m, 3H), 3.68 (m, 1H), 3.57 (d, 1H), 3.31 (s, 3H), 3.29 (dd, 1H), 3.04 (m, 4H), 2.87–2.86 (m, 2H), 2.68–2.63 (m, 3H), 2.44–2.35 (m, 8H), 2.30 (s, 3H), 2.06 (t, 1H), 1.99 (m, 1H), 1.93 (m, 1H), 1.83 (m, 1H), 1.74 (br d, 1H), 1.66–1.57 (m, 3H), 1.45 (s, 3H).

EXAMPLE 28

4"-O-[3-[[2-[(3-carboxy-7-chloro-1-cyclopropyl-1,4-dihydro-4-oxo-6-quinolinyl)amino]ethyl]amino]propiony]-azithromycin To a suspension of intermediate 51 (70 mg) in acetonitrile (10 mL), intermediate 7 (60 mg) and DBU (0.05 mL) were added. This mixture was heated at 70° C. for 18 h. The solvent was evaporated and the residue purified by flash chromatography (eluent: DCM/MeOH/NH$_3$ 90/9/1.5) affording the title compound (13 mg).

MS; m/z (ES): 1125 [MH]$^+$. $^{13}$C-NMR (75 MHz) δ: 178.5; 176.8; 171.7; 166.8; 145.2; 142.5; 131.9; 127.0; 125.6; 117.5; 106.8; 103.7; 101.8; 82.4; 78.2; 77.1; 76.9; 73.5; 73.0; 72.7; 72.3; 70.3; 69.4; 67.3; 64.9; 62.4; 62.0; 48.9; 46.9; 44.7; 43.8; 42.2; 41.9; 41.5; 39.8; 35.5; 34.8; 34.2; 34.0; 28.4; 27.0; 26.1; 21.4; 21.3; 20.7; 20.6; 17.1; 15.7; 13.8; 10.6; 8.3; 7.5; 6.5.

EXAMPLE 29

4"-O-[[[4-[(3-carboxy-1-cyclopropyl-1,4-dihydro-6-fluoro-4-oxo-7-quinolinyl)amino]butyl]amino]carbonyl]azithromycin To a solution of intermediate 52 (130 mg) in DMF (1 mL) 7-((2-aminobutyl)amino)-1-cyclopropyl-1,4-dihydro-6-fluoro-4-oxo-quinoline-3-carboxylic acid (54 mg) and DBU (0.2 mL) were added. The reaction mixture was stirred at room temperature for 24 h. Then EtOAc (30 mL) and H$_2$O (20 mL) were added. The pH of the reaction mixture was adjusted to 9.5 by addition of NaOH (1M). The layers were separated, and the aqueous layer was washed with EtOAc (2×5 mL). The combined organic layers were concentrated under reduced pressure. The residue was dissolved in MeOH (20 mL) and stirred at 60° C. for 4 h and then at room temperature overnight. The solvent was evaporated and the residue purified by flash chromatography (eluent DCM/MeOH/NH$_4$OH 90/10/1.5) affording the title compound (49 mg).

MS; m/z (ES): 1109.54 [MH]$^+$. $^1$H-NMR (500 MHz) δ: 8.69 (s, 1H), 7.91 (d, 1H), 7.00 (d, 1H), 5.18 (d, 1H), 5.12 (brs, 1H), 4.96 (brs, 1H), 4.71 (dd, 1H), 4.55 (d, 1H), 4.53 (d, 1H), 4.34 (m, 1H), 4.24 (d, 1H), 3.76 (m, 1H), 3.66 (s, 1H), 3.60 (d, 1H), 3.54 (m, 1H). $^{13}$C-NMR (125 MHz) δ: 178.2; 176.3; 166.9; 156.0; 151.2; 147.9; 146.2; 141.9; 141.8; 139.7; 109.5; 109.3; 107.1; 101.6; 95.2; 94.1; 83.12; 78.5; 77.4; 73.6; 73.0; 72.9; 72.7; 70.4; 69.4; 67.0; 64.8; 62.8; 62.1; 48.9; 44.7; 42.0; 41.6; 41.5; 39.9; 39.7; 35.6; 34.8; 34.4; 27.1; 29; 26.9; 26.2; 25.2; 21.4; 20.9; 20.6; 20.5; 17.2; 15.6; 14.1; 10.6; 8.7; 7.7; 6.7.

EXAMPLE 30

4"-O-[[[2-[(3-carboxy-7-chloro-1-cyclopropyl-1,4-dihydro-4-oxo-6-quinolinyl)amino]ethyl]amino]carbonyl]-azithromycin To a solution of intermediate 52 (150 mg) in DMF (2 mL) intermediate 7 (65 mg) and DBU (0.4 mL) were added. The reaction mixture was stirred at room temperature for 24 h then EtOAc (30 mL) and H$_2$O (20 mL) were added. The pH of the reaction mixture was adjusted to 9.5 by addition of NaOH (1M). The layers were separated, and the aqueous layer was extracted with EtOAc (2×15 mL). The combined organic layers were concentrated under reduced pressure. The residue was dissolved in MeOH (20 mL) and stirred at 60° C. for 4 h, then at room temperature overnight. The solvent was evaporated under reduced pressure and the residue was purified by flash chromatography (eluent DCM/MeOH/NH$_4$OH 90/10/1.5) affording the title compound (60 mg).

MS; m/z (ES): 1097.1 [MH]$^+$. $^1$H-NMR (300 MHz, CDCl$_3$) δ: 8.72 (s, 1H), 8.05 (s, 1H), 7.47 (s, 1H), 5.39 (t, 1H), 5.25 (m, 1H), 5.18 (d, 1H), 4.70 (dd, 1H), 4.59 (d, 1H), 4.51 (d, 1H), 4.36 (m, 1H), 4.25 (bs, 1H). $^{13}$C-NMR (75 MHz, CDCl$_3$) δ: 178.8; 177.5; 167.3; 157.7; 145.8; 142.9; 132.6; 127.5; 126.2; 118.2; 107.6; 103.7; 102.4; 94.7; 83.3; 79.7; 77.9; 74.2; 73.7; 73.6; 73.2; 70.9; 70.1; 67.8; 65.5; 63.3; 62.5; 49.5; 45.2; 45.1; 42.2; 42.0; 40.4; 39.8; 36.3; 35.4; 35.1; 29.5; 27.5; 26.7; 21.9; 21.6; 21.3; 21.2; 17.8; 16.2; 14.7; 11.3; 9.2; 8.2; 7.4.

EXAMPLE 31

4"-O-[3-[[2-[(3-carboxy-7-chloro-1-cyclopropyl-1,4-dihydro-4-oxo-3-quinolinyl)amino]ethyl]amino]propiony]-6-O-methyl-azithromycin To a solution of intermediate 54 (15 mg) in acetonitrile (0.6 mL) intermediate 7 (11.8 mg) and DBU (0.010 mL) were added. The mixture was stirred for 12 h at 80° C. The solvent was evaporated under reduced pressure and the residue was purified by silica SPE-column (eluent: from DCM 100% to DCM/MeOH/NH$_4$OH 85/13/2) affording the title compound (2.2 mg).

MS; m/z (ES): 1138.7 [MH]$^+$.

EXAMPLE 32

11,12-(aminocarbonyloxy)-4"-O-[3-[[2-[(3-carboxy-7-chloro-1-cyclopropyl-4-oxo-1,4-dihydro-6-quinolinyl)amino]ethyl]amino]propiony]-11,12-dideoxy-6-O-methyl-erythromycin A To a solution of intermediate 57 (20 mg) in acetonitrile (0.40 mL) intermediate 7 (15 mg) was added. This mixture was heated at 70° C. for 12 h. DBU (0.030 mL) was added and the reaction mixture was stirred at the same temperature for additional 3 h. The solvent was evaporated and the residue purified by flash chromatography (eluent: from DCM 100% to DCM/MeOH/NH$_4$OH 85/13/2) affording the title compound (5.8 mg).

MS; m/z (ES): 1148.8 [MH]$^+$. $^1$H-NMR (500 MHz) δ: 8.71 (s, 1H), 8.03 (s, 1H), 7.52 (s, 1H), 5.8 (s, 1H), 5.33 (bt, 1H), 5.10 (dd, 1H), 4.97 (d, 1H), 4.70 (d, 1H), 4.58 (d, 1H), 4.23–4.38 (m, 1H), 3.79 (d, 1H), 3.71–3.74 (m, 1H), 3.67 (s, 1H), 3.61 (d, 1H), 3.58 (d, 1H), 3.43 (m, 1H), 3.31 (s, 3H).

EXAMPLE 33

11,12-(aminocarbonyloxy)-4"-O-[3-[[2-[(3-carboxy-1-cyclopropyl-1,4-dihydro-6-fluoro-4-oxo-7-quinolinyl)amino]ethyl]amino]propiony]-11,12-dideoxy-6-O-methyl-erythromycin A To a solution of intermediate 57 (20 mg) in acetonitrile (0.40 mL) the intermediate 8 (15 mg) was added. This mixture was heated at 70° C. for 12 h. DBU (30 mL) was added and stirred at the same temperature for additional 3 h. The solvent was evaporated under reduced pressure and the residue purified by flash chromatography (eluent: from DCM 100% to DCM/MeOH/NH$_4$OH 85/13/2) affording the title compound (4.0 mg).

MS; m/z (ES): 1132.4 [MH]$^+$.

EXAMPLE 34

4"-O-[3-[[2-[(3-carboxy-7-chloro-1-cyclopropyl-1,4-dihydro-4-oxo-6-quinolinyl)amino]ethyl]amino]propionyl]-11,12-dideoxy-6-O-methyl-11,12-(methylaminocarbonyloxy)-erythromycin A To a solution of intermediate 59 (100 mg) in i-PrOH (2 mL) intermediate 7 (60 mg) and DBU (0.02 mL) were added. This mixture was heated at 70° C. for 36 h, then the solvent was evaporated and the residue purified by flash chromatography (eluent: DCM/MeOH/NH$_4$OH 90/10/1.5) affording the title compound (39 mg).

MS; m/z (ES): 1162 [MH]$^+$. $^1$H-NMR (500 MHz) δ: 8.73 (s, 1H), 8.04 (s, 1H), 7.54 (s, 1H), 5.27 (t, 1H), 4.96 (m, 2H), 4.70 (d, 1H), 4.56 (d, 1H), 4.34 (m, 1H), 3.75 (d, 1H), 3.72 (m, 1H), 3.63 (d, 1H), 3.56 (m, 1H), 3.54 (s, 1H). $^{13}$C-NMR (75 MHz) δ: 215.8; 177.5; 176.6; 172.2; 167.3; 157.7; 145.98; 143.1; 132.5; 127.6; 126.3; 118.0; 107,6; 104.5; 102.1; 95.9; 82.8; 79.8; 78.7; 78.6; 77.6; 75.9; 72.7, 71.0; 67.8; 65.2; 63.0; 62.0; 50.2; 49.6; 47.6; 45.5; 45.2; 44.4; 42.8; 40.3; 38.9; 38.8 (2C); 35.4; 35.1; 34.6; 32.5; 21.9; 21.8; 21.2; 20.0; 18.6; 18.3; 15.9; 13.9; 13.7; 10.3; 9.1; 8.1.

EXAMPLE 35

4"-O-[3-[[2-[(3-carboxy-7-chloro-1-cyclopropyl-1,4-dihydro-4-oxo-6-quinolinyl)amino]ethyl]-methyl-amino]propionyl]-11,12-dideoxy-6-O-methyl-11,12-(methylaminocarbonyloxy)-erythromycin A To a solution of example 34 (150 mg) in CHCl$_3$ (3 mL) formaldehyde (20 mL) and formic acid (18.2 mL) were added. This mixture was heated at 60° C. for 10 h, then CHCl$_3$ (30 mL) and a saturated solution of NaHCO$_3$ (20 mL) were added. The aqueous phase was washed with CHCl$_3$ (15 mL) and the combined organic layers were concentrated under reduced pressure. The residue was purified by flash chromatography (eluent: DCM/MeOH/NH$_4$OH 90/10/1.5) affording of the title compound (76 mg).

MS; m/z (ES): 1176.8 [MH]$^+$. $^1$H NMR (500 MHz, CDCl$_3$) δ: 8.73 (s, 1H), 8.05 (s, 1H), 7.51 (s, 1H), 5.33 (t, 1H), 4.98 (d, 1H), 4.95 (dd, 1H), 4.72 (d, 1H), 4.59 (d, 1H), 4.33 (m, 1H), 3.76 (d, 1H), 3.77–3.70 (m, 1H), 3.63 (d, 1H), 3.57 (m, 1H), 3.54 (s, 1H), 3.35 (m, 2H), 3,32 (s, 3H), 3.27 (m, 1H), 3.09 (s, 3H), 3.03 (m, 1H), 3.01 (s, 3H), 2.91 (m, 1H), 2.29 (s, 3H). $^{13}$C NMR (125 MHz, CDCl$_3$) δ: 215.7; 177.6; 176.6; 171.8; 167.4; 145.8; 143.2; 132.5; 127.6; 126.3; 118.0; 118.0; 107.6; 104.5; 101.9; 95.9; 82.8; 79.9; 78.6; 78.5; 76.0; 72.8; 71.0; 67.7; 65.2; 63.0; 62.1; 55.4; 52.8; 50.2; 49.5; 45.5; 45.2; 41.3; 40.7; 38.9; 38.8; 35.4; 35.1; 32.5; 21.9; 21.7; 21.1; 20.0; 18.5; 18.3; 15.9; 13.9; 13.7; 10.3; 9.2; 8.1. MS; m/z (ES): 855 [MH]$^+$.

EXAMPLE 36

4"-O-[3-[[2-[(3-carboxy-7-chloro-1-cyclopropyl-1,4-dihydro-4-oxo-6-quinolinyl)amino]ethyl]amino]propionyl]-11,12-dideoxy-11,12-(ethylaminocarbonyloxy)-6-O-methyl-erythromycin A To a suspension of intermediate 64 (100 mg) in i-PrOH (2 mL) intermediate 7 (56 mg) and DBU (0.02 mL) were added. This mixture was heated at 70° C. for 24 h then solvent was evaporated and the residue purified by flash chromatography (eluent: DCM/MeOH/NH$_4$OH 90/10/1.5) affording of the title compound (60 mg).

MS; m/z (ES): 1176.6 [MH]$^+$. $^{13}$C NMR (75 MHz, CDCl$_3$) δ: 216.1; 177.5; 176.3; 172.1; 167.3; 157.2; 145.9; 143.1; 132.6; 127.6; 126.3; 118.0; 107.6; 104.5; 102.0; 96.0; 82.6; 79.8; 78.7; 77.7; 76.1; 72.7; 71.0; 67.8; 65.2; 63.1; 60.0; 50.5; 49.5; 47.6; 45.6; 45.1; 44.4; 42.8; 40.4; 38.9; 38.8; 38.7; 38.6; 35.4; 35.1; 34.6; 29.5; 21.9; 21.8; 21.2; 20.1; 18.9; 18.3; 16.0; 14.2; 14.1; 12.5; 10.3; 9.2; 8.1.

EXAMPLE 37

4"-O-[3-[[2-[(3-carboxy-7-chloro-1-cyclopropyl-1,4-dihydro-4-oxo-6-quinolinyl)amino]ethyl]amino]propionyl]-11,12-dideoxy-6-O-methyl-11,12-[(N-(4-phenylbutyl)amino)carbonyloxy]-erythromycin A To a solution of intermediate 67 in i-PrOH (10 mL) and CH$_3$CN (2 mL) intermediate 7 (0.5 g) was added. This mixture was heated at 80° C. for 24 h then the solvent was evaporated and the residue purified by flash chromatography (eluent: DCM/MeOH/NH$_4$OH 90/10/1.5) affording the title compound (1.0 g).

MS; m/z (ES): 1281 [MH]$^+$.

EXAMPLE 38

4"-O-[3-[[2-[(3-carboxy-7-chloro-1-cyclopropyl-1,4-dihydro-4-oxo-6-quinolinyl)amino]ethyl]amino]propionyl]-6-O-methyl-erythromycin A To a suspension of intermediate 69 (500 mg) in acetonitrile (10 mL) were added intermediate 7 (300 mg) and DBU (0.4 mL). This mixture was heated at 70° C. for 18 h. The solvent was evaporated under reduced pressure and the residue purified by flash chromatography (eluent DCM/MeOH/NH$_4$OH 90/10/1.5) affording of the title compound (370 mg).

MS; m/z (ES): 1124.7 [MH]$^+$. $^1$H-NMR (300 MHz) δ: 8.73 (s, 1H), 8.04 (s, 1H), 7.54 (s, 1H), 5.26 (t, 1H), 5.06 (dd, 1H), 4.99 (d, 1H), 4.70 (d, 1H), 4.57 (d, 1H), 4.34 (m, 1H). $^{13}$C-NMR (75 MHz) δ: 221.0; 177.5; 175.7; 172.2; 167.284, 145.8; 143.1; 132.5; 127.6; 126.3; 118.0; 107.7; 104.6; 102.2; 96.0; 80.4; 78.9; 78.8; 78.3; 78.2; 76.6; 74.3; 72.7, 71.1; 69.1; 67.8; 65.2; 63.0; 50.67.

EXAMPLE 39

4"-O-[3-[[2-[(3-carboxy-1,4-dihydro-1-ethyl-4-oxo-7-quinolinyl)amino]ethyl]amino]propionyl]-6-O-methyl-erythromycin A A solution of intermediate 69 (100 mg) and intermediate 3 (103 mg) in MeOH (1 mL) was shaken at 70° C. for 16 h. The solvent was evaporated and the residue was triturated with DCM (2 mL). The solid material was filtered and washed with DCM (1 mL). The mother liquor was concentrated under reduced pressure. The crude product was precipitated from EtOAc/n-hexane 1/1 affording the title compound (10 mg).
MS; m/z (ES): 1077.8 [MH]+.

EXAMPLE 40

4"-O-[3-[[2-[(3-carboxy-1-cyclopropyl-1,4-dihydro-4-oxo-7-quinolinyl)amino]ethyl]amino]propionyl]-6-O-methyl-erythromycin A A solution of intermediate 69 (100 mg) and intermediate 4 (107 mg) in MeOH (1 mL) was shaken at 70° C. for 16 h. The solvent was evaporated and the residue was triturated with DCM (2 mL). The solid was filtered and washed with DCM (1 mL). The mother liquor was concentrated under reduced pressure. The crude product was precipitated from EtOAc/n-hexane 1/1 two times affording the title compound (15 mg).
MS; m/z (ES): 1090.8 [MH]+.

EXAMPLE 41

4"-O-[3-[[2-[(3-carboxy-1-cyclopropyl-1,4-dihydro-6-fluoro-4-oxo-7-quinolinyl)amino]butyl]amino]propionyl]-6-O-methyl-erythromycin A To a solution of intermediate 69 (100 mg) in i-PrOH (2 mL) 7-((2-aminobutyl)amino)-1-cyclopropyl-1,4-dihydro-6-fluoro-4-oxo-quinoline-3-carboxylic acid (62 mg) was added. This mixture was heated at 80° C. for 72 h then the solvent was evaporated and the residue purified by flash chromatography (eluent: DCM/MeOH/NH$_4$OH 90/9/1.5) affording the title compound (141 mg).
MS; m/z (ES): 1136.1 [MH]+.

EXAMPLE 42

4"-O-[3-[[2-[(3-carboxy-7-chloro1,4-dihydro-1-ethyl-4-oxo-6-quinolinyl)amino]ethyl]amino]propiony]-6-O-methyl-erythromycin A and 4"-O-[3-[[2-[(3-carboxy-1,4-dihydro-1-ethyl-6-fluoro-4-oxo-7-quinolinyl)amino]ethyl]amino]propiony]-6-O-methyl-erythromycin A To a solution of intermediate 69 (133 mg) in i-PrOH (2 mL) intermediate 5 and intermediate 6 (100 mg, mixture 1/1) were added. The reaction mixture was heated at 80° C. for 10 days. The solvent was evaporated and the residue purified by flash chromatography (eluent: DCM/MeOH/NH$_4$OH 90/9/1.5) affording the title compounds as 1/1 mixture (140 mg).
MS; m/z (ES): 112.1 [MH]+; 1096.1 [MH]+.

EXAMPLE 43

4"-O-[3-[[3-[(3-carboxy-7-chloro-1-cyclopropyl-1,4-dihydro-4-oxo-6-quinolinyl)-amino]propyl]amino] propionyl]-6-O-methyl-erythromycin A To a solution of intermediate 68 (10 mg) in i-PrOH (2.5 mL) intermediate 13 (20 mg) was added and the reaction mixture was heated at 70° C. for 32 h. The reaction mixture was filtered washing the solid with i-PrOH. The combined solution was concentrated under reduced pressure and stirred in MeOH for 72 h. Solvent evaporation gave the crude product, which was purified by preparative TLC (eluent: MeOH/NH$_4$OH 97/3) affording the title compound (4.4 mg).
$^1$H-NMR (500 MHz) δ: 8.73 (s, 1H), 8.02 (d, 1H), 7.53 (bs, 1H), 5.83 (bs, 1H), 4.70 (d, 1H), 4.36 (m, 1H), 3.60–3.40 (m, 2H), 2.92 (m, 2H), 2.85 (m, 2H), 2.65 (m, 2H), 2.00 (m, 2H), 1.39 (m, 2H), 1.16 (m, 2H).

EXAMPLE 44

4"-O-[3-[[3-[(3-carboxy-1-cyclopropyl-1,4-dihydro-6-fluoro-4-oxo-7-quinolinyl)-amino]propyl]amino] propionyl]-6-O-methyl-erythromycin A To a solution of intermediate 68 (7 mg) in i-PrOH (2 mL) intermediate 14 (14 mg) was added and the reaction mixture was heated at 70° C. for 32 h. The reaction mixture was filtered washing the solid with i-PrOH. The combined solution was concentrated under reduced pressure and stirred in MeOH for 72 h. Solvent evaporation gave the crude product which was purified by preparative TLC (eluent: MeOH/NH$_4$OH 97/3) affording the title compound (3.6 mg).
$^1$H-NMR (500 MHz) δ: 8.73 (s, 1H), 7.94 (d, 1H), 7.02 (bs, 1H), 6.91 (d, 1H), 4.70 (d, 1H), 4.36 (m, 1H), 3.50–3.30 (m, 4H), 2.96–2.88 (m, 4H), 2.70–2.55 (m, 2H), 1.39 (m, 2H), 1.16 (m, 2H).

EXAMPLE 45

4"-O-[3-[[2-[(3-carboxy-1-cyclopropyl-6-fluoro-1,4-dihydro-4-oxo-7-quinolinyl)-amino]ethyl]amino] propionyl]-6-O-methyl-erythromycin A To a solution of intermediate 8 (50.4 mg) in anhydrous DMSO (1 mL), DIPEA (0.02 mL) was added and the reaction mixture was stirred at room temperature for 1 h. This mixture was added to a solution of intermediate 68 (50 mg) in DMSO (1 mL) and the reaction mixture was heated at 80° C. for 12 h. The reaction mixture was cooled to room temperature and DCM (10 mL) was added followed by water (10 mL). The organic phase was washed with water (3×10 mL), dried, filtered and concentrated under reduced pressure. The crude product was dissolved in MeOH (0.5 mL) and the solution was heated at 40° C. for 12 h. The solvent was evaporated under reduced pressure, the crude obtained was dissolved in DCM (0.1 mL). Et$_2$O (0.5 mL) was added and a precipitate was obtained. The solid was filtered and the filtrate was evaporated under reduced pressure to afford the title compound (23 mg).
HPLC/MS analysis (mobile phase: A/B from 70/30 to 45/55 in 10 min, from 45/55 to 10/90 in 5 min, 10/90 for 5 min, mass range 150–1000 amu): retention time: 9.15 min, MS; m/z (ES): 1108 [MH]+. $^1$H-NMR (500 MHz) δ: 8.73 (s, 1H), 7.97 (d, 1H), 7.00 (d, 1H), 5.49 (bm, 1H), 4.70 (d, 1H), 4.35 (bm, 1H), 3.50 (m, 1H), 3.35 (m, 2H), 3.05 (m, 2H), 3.00 (m, 2H), 2.68☐2.50 (m, 2H), 1.38 (m, 2H), 1.20 (m, 2H).

EXAMPLE 46

4"-O-[3-[4-(3-carboxy-1-cyclopropyl-6-fluoro-1,4-dihydro-4-oxo-7-qinolinyl)-1-piperazinyl]propionyl]-6-O-methyl-erythromycin A To a solution of intermediate 68 (20 mg) in MeOH (1 mL), DIPEA (0.021 mL) and 1-cyclopropyl-6-fluoro-4-oxo-7-piperazin-1-yl-1,4-dihydro-quinoline-3-carboxylic acid (40 mg) were added and the reaction mixture was heated at 40° C. for 24 h. The solvent was evaporated and the residue dissolved in DCM (2 mL). Isocyanate polymer-bound (Aldrich, loading 2 mmol/g, 120 mg) was added and the mixture was shaken at room temperature overnight. The resin was filtered and washed with DCM (2 mL), MeOH (2 mL) and DCM (2 mL). The collected organic extracts were evaporated under reduced pressure. The residue was dissolved in DCM (3 mL) and washed with water (3×3 mL), the combined aqueous phase was extracted with DCM (3×3 mL). The organic phase was dried over $Na_2SO_4$, filtered and concentrated under reduced pressure. The crude material was purified by flash chromatography (eluent: DCM/MeOH 90/10) affording the title compound (7.8 mg).

$^1$H-NMR (500 MHz) δ: 15.00 (bs, 1H), 8.79 (s, 1H), 8.04 (d, 1H), 7.35 (d, 1H), 4.72 (d, 1H), 4.35 (m, 1H), 3.55 (m, 1H), 3.40–3.10 (m, 2H), 2.86–2.64 (m, 6H), 2.60 (m, 4H), 1.39 (m, 2H), 1.15 (m, 2H).

EXAMPLE 47

4"-O-[3-[4-(3-carboxy-1-ethyl-1,4-dihydro-6-fluoro-4-oxo-[1,8]naphtylridinyl)-1-piperazinyl]propionyl]-6-O-methylerythromycin A To a solution of intermediate 68 (20 mg) in anhydrous MeOH (2 mL) 1-ethyl-6-fluoro-4-oxo-7-piperazin-1-yl-1,4-dihydro[1,8]naphthyridine-3-carboxylic acid (19 mg) was added. The reaction mixture was stirred at 40° C. overnight, the solvent was evaporated under reduced pressure and the residue dissolved in DCM (3 mL). Isocyanate polymer-bound (Aldrich, loading 2 mmol/g, 118 mg) was added and the mixture was shaken at room temperature overnight. The resin was filtered and washed with DCM (3 mL), MeOH (3 mL) and DCM (3 mL). The collected organic extracts were evaporated under reduced pressure. The residue was dissolved in DCM (5 mL) and washed with water (3×3 mL), the combined aqueous phase was extracted with DCM (3×3 mL). The organic phase was dried over $Na_2SO_4$, filtered and concentrated under reduced pressure. The crude product was purified by flash chromatography (eluent: DCM/MeOH 90/10) affording the title compound (12 mg).

$^1$H-NMR (500 MHz) δ: 15.00 (bs, 1H), 8.71 (s, 1H), 8.12 (m, 1H), 4.72 (d, 1H), 4.41 (q, 2H), 4.35 (m, 1H), 3.85 (m, 4H), 2.84–2.54 (m, 4H), 2.64 (m, 4H), 1.51 (t, 3H).

EXAMPLE 48

4"-O-[3-[4-(3-carboxy-1-cyclopropyl-6-fluoro-1,4-dihydro-4-oxo-7-quinolinyl)-1-piperazinyl]ethanoyl]-6-O-methyl-erythromycin A To a solution of intermediate 70 (82 mg) in DMSO (0.5 mL), a preformed solution of DIPEA (0.054 mL) and 1-cyclopropyl-6-fluoro-4-oxo-7-piperazin-1-yl-1,4-dihydro-quinoline-3-carboxylic acid (38 mg) in DMSO (1.3 mL) was added. The reaction mixture was stirred at room temperature for 6 h. Water (10 mL) and EtOAc (10 mL) were added and the aqueous phase was extracted with EtOAc (3×10 mL). The organic phase was dried, filtered and concentrated under reduced pressure. The crude material was purified by flash chromatography (eluent: DCM/MeOH 90/10) and heated in MeOH (12 mL) at 40° C. for 16 h. Solvent evaporation under reduced pressure afforded the title compound (37 mg).

$^1$H-NMR (500 MHz) δ: 15.00 (bs, 1H), 8.76 (s, 1H), 7.99 (d, 1H), 7.36 (d, 1H), 4.75 (d, 1H), 4.36 (m, 1H), 3.55 (m, 1H), 3.45–3.25 (d+d, 2H), 3.41 (m, 4H), 2.84 (m, 4H), 1.40–1.16 (m, 4H).

EXAMPLE 49

4"-O-[2-[[2-[(3-carboxy-7-chloro-1-cyclopropyl-1,4-dihydro-4-oxo-6-quinolinyl)amino]ethyl]amino]ethanoyl]-6-O-methyl-erythromycin A To a solution of intermediate 70 (40 mg) in DMSO (0.3 mL), a preformed solution of DIPEA (0.036 mL) and intermediate 7 (23 mg) in DMSO (0.7 mL) was added. The reaction mixture was stirred at room temperature for 16 h. Water (5 mL) and EtOAc (10 mL) were added and the aqueous phase was extracted with EtOAc (3×10 mL). The organic phase was dried, filtered and concentrated under reduced pressure. The crude material was purified by flash chromatography (eluent: DCM/MeOH 90/10) and heated in MeOH (12 mL) at 50° C. for 16 h. Solvent evaporation under reduced pressure afforded the title compound (11 mg).

$^1$H-NMR (500 MHz) δ: 15.07 (bs, 1H), 8.74 (s, 1H), 8.05 (s, 1H), 7.55 (s, 1H), 5.30 (t, 1H), 4.75 (d, 1H), 3.55 (m, 1H), 3.41 (bm, 2H), 3.45–3.40 (m, 1H), 3.04–3.00 (m, 2H), 1.39–1.1 (m, 4H).

EXAMPLE 50

4"-O-[2-[[2-[(3-carboxy-1-cyclopropyl-6-fluoro-1,4-dihydro-4-oxo-7-quinolinyl)amino]ethyl]amino]ethanoyl]-6-O-methyl-erthromycin A To a solution of intermediate 70 (46 mg) in DMSO (0.3 mL), a preformed solution of DIPEA (0.036 mL) and intermediate 8 (24 mg) in DMSO (0.7 mL) was added. The reaction mixture was stirred at room temperature for 16 h. Water (5 mL) and EtOAc (10 mL) were added and the aqueous phase was extracted with EtOAc (3×10 mL). The organic phase was dried, filtered and concentrated under reduced pressure. The crude material was purified by flash chromatography (eluent: DCM/MeOH 90/10) and heated in MeOH (12 mL) at 50° C. for 16 h. Solvent evaporation under reduced pressure afforded the title compound (10 mg).

$^1$H-NMR (500 MHz) δ: 15.30 (bs, 1H), 8.70 (s, 1H), 7.94 (d, 1H), 7.01 (d, 1H), 5.51 (bm, 1H), 4.75 (d, 1H), 3.60 (d, 1H), 3.51 (m, 1H), 3.40 (d, 1H), 3.38 (m, 2H), 3.10–3.02 (m, 2H), 1.40–1.06 (m, 4H).

EXAMPLE 51

4"-O-[3-[[2-[(3-carbamoyl-1-cyclopropyl-6-fluoro-1,4-dihydro-4-oxo-7-quinolinyl)amino]ethyl]amino]propionyl]-6-O-methyl-erthromycin A and 4"-O-[3-[[2-[(3-carbamoyl-7-chloro-1-cyclopropyl-1,4-dihydro-4-oxo-6-quinolinyl)amino]ethyl]amino]propionyl]-6-O-methyl-erythromycin A A suspension of a 40/60 mixture of intermediates 19 and 20 (50 mg) in i-PrOH (1 mL) and DBU (0.64 mL) was heated at 50° C. for 30 min in a sealed tube. Intermediate 69 (50 mg) was added and the reaction mixture was stirred at 70° C. for 24 h then concentrated under reduced pressure. Water (10 mL) was added and the obtained mixture was extracted with EtOAc (3×10 mL). The combined organic phase was dried, filtered and concentrated under reduced pressure. The crude product was purified by preparative TLC (eluent DCM/MeOH/NH₄OH 90/10/2) and stirred in MeOH (10 mL) at 50° C. overnight. Solvent evaporation under reduced pressure gave the title compound (13 mg).

¹H-NMR (500 MHz) δ: 9.83 (bm, 1H), 8.77 (s, 1H), 7.97 (d, 1H), 6.96 (d, 1H), 5.68 (bm, 1H), 5.24 (bm, 1H), 4.70 (d, 1H), 4.36 (m, 1H), 3.47–3.30 (m, 3H), 3.04–2.80 (m, 4H), 2.65–2.52 (m, 4H), 1.35–1.12 (m, 4H).

EXAMPLE 52

4"-O-[3-[[2-[(3-carboxy-1-cyclopropyl-4-oxo-1,4-dihydro-6-quinolinyl)amino]ethyl]amino]propionyl]-6-O-methyl-erythromycin A To a solution of example 38 (60 mg) in MeOH (20 mL), Pd/C (10%, 30 mg) was added and the mixture was hydrogenated at room temperature at 15 bar for 20 h. The catalyst was filtered and washed with MeOH and the filtrate was concentrated under reduced pressure. The residue was purified by flash chromatography (eluent DCM/MeOH/NH₃ 90/13/2) affording the title compound (23 mg).

MS; m/z (ES): 1089.6 [MH]⁺. ¹³C-NMR (75 MHz) δ: 177.9, 175.7, 172.3, 167.8, 147.0, 145.1, 133.2, 127.5, 122.2, 118.4, 107.3, 104.2, 102.0, 96.0, 80.4, 78.8, 78.3, 78.1, 74.3, 72.7, 71.1, 69.1, 67.8, 65.2, 63.0, 50.7, 49.5, 47.7, 45.3, 44.9, 44.5, 42.8, 40.3, 39.2, 38.8, 37.2, 35.4, 35.2, 34.5, 21.8, 21.2, 21.0, 19.7, 18.4, 18.0, 16.0, 12.4, 10.6, 9.1, 8.1.

EXAMPLE 53

4"-O-[3-[[2-[(3-carboxy-7-chloro-1-cyclopropyl-1,4-dihydro-4-oxo-6-quinolinyl)amino]ethyl]amino]propionyl]-6-O-propyl-erythromycin A To a solution of intermediate 74 (200 mg) in i-PrOH (5 mL) intermediate 7 (150 mg) was added and the mixture was shaken at 80° C. for 60 h. The solvent was evaporated, the residue was triturated with DCM (2 mL). The solid was filtered, washed with DCM (1 mL) and the mother liquor was concentrated under reduced pressure. The crude product was precipitated from EtOAc/n-hexane 1/1 two times affording the title compound (8.3 mg).

MS; m/z (ES): 1152.3 [MH]⁺. ¹³C-NMR (500 MHz) (δ/ppm): 177.9, 175.7, 172.3, 167.8, 147.0, 145.1, 133.2, 127.5, 122.2, 118.4, 107.3, 104.2, 102.0, 96.0, 80.4, 78.8, 78.3, 78.1, 74.3, 72.7, 71.1, 69.1, 67.8, 65.2, 63.0, 50.7, 49.5, 47.7, 45.3, 44.9, 44.5, 42.8, 40.3, 39.2, 38.8, 37.2, 35.4, 35.2, 34.5, 21.8, 21.2, 21.0, 19.7, 18.4, 18.0, 16.0, 12.4, 10.6, 9.1, 8.1.

EXAMPLE 54

(11S,11aR)-11-(carboxycyanomethyl)-4"-O-[3-[4-(3-carboxy-1-cyclopropyl-1,4-dihydro-4-oxo-7-quinolinyl)piperazinyl]propionyl]-11-deoxy-6-O-methyl-erythromycin A To a solution of intermediate 81 (10 mg) in anhydrous MeOH (0.5 mL), 1-cyclopropyl-1,4-dihydro-4-oxo-7-(piperazin-1-yl)-quinoline-3-carboxylic acid (18 mg) and DIPEA (0.010 mL) were added. The reaction mixture was stirred at 40° C. overnight then the solvent was evaporated and the residue dissolved in DCM (2 mL). Isocyanate polymer-bound (Aldrich, loading 2 mmol/g, 56 mg) was added and the mixture shaken at room temperature overnight. The resin was filtered and washed with DCM (2 mL), MeOH (2 mL) and DCM (2 mL). The collected organic extracts were evaporated under reduced pressure. The residue was dissolved in DCM (3 mL) and washed with water (3×3 mL), the combined aqueous phase was extracted with DCM (3×3 mL). The organic phase was dried, filtered and concentrated under reduced pressure. The crude material was purified by flash chromatography (eluent: DCM/MeOH 90/10) affording the title compound (9 mg).

¹H-NMR (500 MHz) δ: 15.36 (bs, 1H), 11.29 (mb, 1H), 8.77 (s, 1H), 8.32 (d, 1H), 7.20 (d, 1H), 7.14 (dd, 1H), 5.26 (dd, 1H), 4.98 (d, 1H), 4.73 (m, 2H), 4.65 (bm, 1H), 4.30 (bm, 1H), 3.88 (d, 1H), 3.80 (bm, 1H), 3.69–3.64 (m, 3H), 3.51 (m, 1H), 3.46 (m, 4H), 3.33 (s, 3H), 3.10 (m, 7H), 3.02 (m, 1H), 2.90 (m, 1H), 2.79 (m, 2H), 2.68 (m, 4H), 2.59 (m, 3H), 2.42 (d, 1H), 1.93 (m, 1H), 1.86 (m, 1H), 1.75 (m, 2H), 1.66 (m, 1H), 1.7–1.2 (m, 2H), 1.5 (s, 3H), 1.37 (m+s, 5H), 1.17 (s, 3H), 1.27–1.04 (m, 20H), 0.91 (t, 3H).

EXAMPLE 55

(11S,11aR)-11-(carboxycyanomethyl)-4"-O-[3-[4(1-cyclopropyl-6-fluoro-1,4-dihydro-4-oxo-7-quinolinyl)piperazinyl]propionyl]-11-deoxy-6-O-methyl-erythromycin A To a solution of intermediate 81 (10 mg) in anhydrous MeOH (0.5 mL), 1-cyclopropyl-1,4-dihydro-6-fluoro-4-oxo 7-(piperazin-1-yl)-quinoline (16 mg) and DIPEA (0.010 mL) were added. The reaction mixture was stirred at 40° C. overnight, the solvent was evaporated and the residue dissolved in DCM (2 mL). Isocyanate polymer-bound (Aldrich, loading 2 mmol/g, 0.056 g) was added and the mixture was shaken at room temperature overnight. The resin was filtered and washed with DCM (2 mL), MeOH (2 mL) and DCM (2 mL). The combined organic extracts were evaporated under reduced pressure. The residue was dissolved in DCM (3 mL) and washed with water (3×3 mL), the combined aqueous phase was extracted with DCM (3×3 mL). The organic phase was dried, filtered and concentrated under reduced pressure. The crude material was purified by flash chromatography (eluent: DCM/MeOH 90/10) affording the title compound (7 mg).

¹H-NMR (500 MHz) δ: 7.99 (d, 1H), 7.62 (d, 1H), 7.26 (d, 1H), 6.16 (d, 1H), 5.26 (dd, 1H), 4.98 (d, 1H), 4.74 (d, 1H), 4.73 (d, 1H), 4.63 (d, 1H), 4.33 (m, 1H), 3.88 (d, 1H), 3.78 (m, 1H), 3.67 (d, 1H), 3.35 (m, 1H), 3.32 (s, 1H), 3.26 (m, 4H), 3.25 (m, 2H), 3.10 (s, 3H), 3.09 (s, 1H), 3.02 (m, 1H), 2.90 (m, 1H), 2.82–2.78 (m, 2H), 2.73–2.69 (m, 5H), 2.61–2.57 (m, 3H), 2.42 (m, 1H), 2.48 (s, 6H), 1.93 (m, 1H), 1.87 (m, 1H), 1.87–1.70 (m, 3H), 1.70–1.65 (m, 3H), 1.49 (s, 3H), 1.37 (s, 3H), 1.27 (d, 3H), 1.26 (m, 2H), 1.22 (d, 3H), 1.17 (s, 3H), 1.14 (s, 3H), 1.12 (s, 3H), 1.10 (s, 3H), 1.05 (m, 2H), 1.05 (d, 3H), 0.91 (t, 3H).

EXAMPLE 56

(11S,11aR)-11-(carboxycyanomethyl)-4"-O-[3-[[2-[(3-carboxy-1-cyclopropyl-6-fluoro-1,4-dihydro-4-oxo-7-quinolinyl)amino]ethyl]amino]propionyl]-11-deoxy-6-O-methyl-erythromycin A To a solution of intermediate 81 (10 mg) in MeOH (1 mL) DIPEA (0.01 mL) and intermediate 8 (17 mg) were added. The reaction was stirred at 60° C. for 3 days then cooled to room temperature and DCM (2 mL) and 4-benzyloxybenzaldehyde polymer-bound (Aldrich, loading 2.5–3 mmol/g, 56 mg) were added. The reaction mixture was shaken at room temperature for 24 h. The resin was filtered and washed with DCM (2 mL), MeOH (2 mL) and DCM (2 mL). The combined organic extracts were evaporated under reduced pressure. The crude material was purified by flash chromatography (eluent: DCM/MeOH 90/10) affording the title compound (6 mg).

HPLC/MS analysis (mobile phase: A/B from 80/20 to 10/90 in 20 min, mass range 150–1000 amu): retention time: 10.18 min, MS; m/z (ES): 1156 [MH]$^+$.

EXAMPLE 57

(11S,11aR)-4"-O-[3-[4-(3-carboxy-7-chloro-1-cyclopropyl-1,4-dihydro-4-oxo-7-quinolinyl)-piperazinyl]propionyl]-11-(carboxycyanomethyl)-11-deoxy-6-O-methyl-erythromycin A To a solution of intermediate 81 (10 mg) in anhydrous MeOH (0.5 mL), 7-chloro-1-cyclopropyl-1,4-dihydro-4-oxo-6-(piperazin-1-yl)-quinoline-3-carboxylic acid (20 mg) and DIPEA (0.010 mL) were added. The reaction mixture was stirred at 60° C. for 2 days, the solvent was evaporated and the residue dissolved in DCM (2 mL). Isocyanate polymer-bound (Aldrich, loading 2 mmol/g, 56 mg) was added and the mixture was shaken at room temperature overnight. The resin was filtered and washed with DCM (2 mL), MeOH (2 mL) and DCM (2 mL). The combined organic extracts were evaporated under reduced pressure. The residue was dissolved in DCM (3 mL) and washed with water (3×3 mL) the combined aqueous phase was extracted with DCM (3×3 mL). The organic phase was dried over Na$_2$SO$_4$, filtered and concentrated under reduced pressure. The crude material was purified by flash chromatography (eluent: DCM/MeOH 90/10) affording the title compound (10 mg).

$^1$H-NMR (500 MHz) δ: 14.47 (bs, 1H), 8.82 (s, 1H), 8.03 (d, 1H), 8.11 (d, 1H), 5.26 (dd, 1H), 4.98 (d, 1H), 4.74 (s, 1H), 4.73 (d, 1H), (4.63 (d, 1H), 4.32 (m, 1H), 3.87 (d, 1H), 3.78 (m, 1H), 3.67 (d, 1H), 3.57 (m, 1H), 3.33 (s, 3H), 3.28 (bm, 1H), 3.18 (bs, 1H), 3.10 (m+s, 3H+1H), 3.02 (m, 1H), 2.91 (m, 1H), 2.80 (m, 2H), 2.71 (bm, 4H), 2.59 (m, 4H), 2.44 (s, 6H), 2.43 (d, 1H), 1.95–1.82 (m, 2H), 1.76–1.60 (m, 5H), 1.49 (s, 3H), 1.43 (m, 1H), 1.38 (s, 3H), 1.26 (s, 3H), 1.25 (m, 1H), 1.22 (d, 3H), 1.22 (m, 2H), 1.18 (d, 3H), 1.14 (d, 3H), 1.12 (d, 3H), 1.11 (d, 3H), 1.05 (d, 3H), 0.91 (t, 3H).

EXAMPLE 58

(11S,11aR)-4"-O-[3-[[2-[(3-carboxy-7-chloro-1-cyclopropyl-1,4-dihydro-4-oxo-6-quinolinyl)amino]ethyl]amino]propionyl]-11-(carboxycyanomethyl)-11-deoxy-6-O-methyl-erythromycin A A solution of intermediate 7 (54 mg) and DIPEA (0.030 mL) in anhydrous i-PrOH (2 mL) was left in ultrasonic bath for 1 min. Intermediate 81 (60 mg) was added and the reaction mixture was stirred at 120° C. for 7 days. The solvent was evaporated, the residue dissolved in MeOH (3 mL) and the mixture stirred at room temperature overnight. After solvent evaporation, the residue was dissolved in DCM (3 mL), 4-benzyloxybenzaldehyde polymer-bound (Aldrich, loading 2.5–3 mmol/g, 160 mg) was added and the mixture was shaken at room temperature overnight. The resin was filtered and washed with DCM (7 mL), MeOH (7 mL) and DCM (7 mL). The combined organic extracts were concentrated under reduced pressure. The residue was dissolved in DCM (10 mL) and washed with water (3×10 mL) and the combined aqueous phase was extracted with DCM (3×10 mL). The organic phase was dried over Na$_2$SO$_4$, filtered and concentrated under reduced pressure. The crude material was purified by flash chromatography (eluent: DCM/MeOH 90/10) affording the title compound (29 mg).

$^1$H-NMR (500 MHz) δ: 8.74 (s, 1H), 8.05 (s, 1H), 7,55 (s, 1H), 5.25 (m, 2H), 4.97 (d, 1H), 4.74 (d, 1H), 4.71 (d, 1H), 4.57 (d, 1H), 4.33 (m, 1H), 3.87 (d, 1H), 3.70 (m, 1H), 3.65 (d, 1H), 3.56 (m, 1H), 3.39 (m, 2H), 3.32 (s, 3H), 3.19 (dd, 1H), 3.09 (m+s, 4H), 3.02–2.95 (m, 5H), 2.90 (m, 1H), 2.61–2.53 (m, 4H), 2.42 (m, 4H), 2.31 (s, 6H), 1.92–1.58 (m, 7H), 1.49 (s, 3H), 1.43 (m, 2H), 1.36 (s, 3H), 1.86–1.26 (m, 6H), 1.19 (m, 1H), 1.13–1.11 (m, 9H), 1.04 (m, 3H), 0.91 (t, 3H).

EXAMPLE 59

(11S,11aR)-11-(carboxycyanomethyl)-4"-O-[3-[4-(3-carboxy-1-cyclopropyl-1,4-dihydro-6-fluoro-4-oxo-7-quinolinyl)piperazinyl]propionyl]-11-deoxy-6-O-methyl-erythromycin A To a solution of intermediate 81 (40 mg) in anhydrous MeOH (2 mL), 1-cyclopropyl-1,4-dihydro-6-fluoro-4-oxo-7-(piperazin-1-yl)-quinoline-3-carboxylic acid (82 mg) and DIPEA (0.038 mL) were added. The reaction mixture was stirred at 40° C. overnight, the solvent was evaporated and the residue dissolved in DCM (4 mL). Isocyanate polymer-bound (Aldrich, loading 2 mmol/g, 220 mg) was added and the reaction mixture was shaken at room temperature overnight. The resin was filtered and washed with DCM (4 mL), MeOH (4 mL) and DCM (4 mL). The combined organic extracts were evaporated under reduced pressure. The residue was dissolved in DCM (5 mL) and washed with water (3×3 mL), the combined aqueous phase was extracted with DCM (3×3 mL). The organic phase was dried, filtered and concentrated under reduced pressure. The crude material was purified by flash chromatography (eluent: DCM/MeOH 90/10) affording the title compound (19 mg).

$^1$H-NMR (500 MHz) δ: 14.98 (bs, 1H), 8.80 (s, 1H), 8.05 (d, 1H), 8.03 (d, 1H), 7.35 (d, 1H), 5.26 (dd, 1H), 4.98 (d, 1H), 4.74 (m, 2H), 4.72 (d, 1H), 4.60 (d, 1H), 4.34 (m, 1H), 3.88 (d, 1H), 3.75 (m, 1H), 3.67 (d, 1H), 3.54 (m, 1H), 3.33 (s, 3H), 3.32 (m, 1H), 3.21 (m, 1H), 3.10 (m, 5H), 3.02 (m, 1H), 2.90 (m, 1H), 2.85–2.70 (m, 2H), 2.70 (m, 4H), 2.58 (m, 4H), 2.43 (d, 1H), 2.32 (s, 6H), 1.92 (m, 1H), 1.86 (m, 1H), 1.76 (m, 2H), 1.66 (m, 2H), 1.58 (m, 1H), 1.50 (s, 3H), 1.43 (m, 1H), 1.39 (m, 1H), 1.37 (s, 3H), 1.30 (m, 1H), 1.25 (d, 3H), 1.21 (d, 3H), 1.22 (m, 1H), 1.17 (s, 3H), 1.14 (d, 3H), 1.13 (d, 3H), 1.12 (d, 3H), 1.05 (d, 3H), 0.91 (t, 3H).

EXAMPLE 60

(11S,11aR)-11-carboxycyanomethyl)-4"-O-[3-[rel-(4aS,7aS)-6-(3-carboxy-1-cyclopropyl-6-fluoro-1,4-dihydro-4-oxo-7-quinolinyl)octahydro-1H-pyrrolo[3,4-b]pyridin-1-yl]propionyl]-11-deoxy-6-O-methyl-erythromycin A To a solution of intermediate 81 (40 mg) in anhydrous MeOH (2 mL), 1-cyclopropyl-6-fluoro-8-methoxy-7-(octahydro-pyrrolo[3,4-b]pyridin-6-yl)-4-oxo-1,4-dihydro-quinoline-3-carboxylic acid (98 mg) and DIPEA (0.038 mL) were added. The reaction mixture was stirred at 40° C. overnight, the solvent was evaporated and the residue dissolved in DCM (4 mL). Isocyanate polymer-bound (Aldrich, loading 2 mmol/g, 220 mg) was added and the mixture was shaken at room temperature overnight. The resin was filtered and washed with DCM (4 mL), MeOH (4 mL) and DCM (4 mL). The collected organic extracts were evaporated under reduced pressure. The residue was dissolved in DCM (5 mL) and washed with water (3×3 mL), the combined aqueous phase was extracted with DCM (3×3 mL). The organic phase was dried over $Na_2SO_4$, filtered and concentrated under reduced pressure. The crude material was purified by flash chromatography (eluent: DCM/MeOH 90/10) affording the title compound (44 mg).

$^1$H-NMR (500 MHz) δ: 15.05 (bs, 1H), 8.78 (s, 1H), 7.81 (d, 1H), 5.26 (dd, 1H), 4.95 (d, 1H), 4.74 (s, 1H), 4.60 (d, 1H), 4.56 (d, 1H), 4.60 (d, 1H), 4.32 (m, 1H), 4.01 (d, 1H), 3.90 (m, 1H), 3.87 (d, 1H), 3.70 (m, 1H), 3.65 (m, 3H), 3.56 (m, 1H), 3.30 (s, 3H), 3.18 (m, 1H), 3.17 (m, 1H), 3.09 (m, 1H), 3.10 (m, 4H), 3.02 (m, 1H), 2.95 (m, 1H), 2.91 (m, 1H), 2.78 (m, 2H), 2.62 (m, 4H), 2.60 (m, 1H), 2.52 (m, 3H), 2.36 (d, 1H), 2.35 (m, 1H), 2.29 (s, 6H), 1.92 (m, 1H), 1.90 (m, 1H), 1.86 (m, 1H), 1.76 (m, 1H), 1.72–1.68 (m, 5H), 1.60 (m, 2H), 1.49 (s, 3H), 1.37 (s, 3H), 1.25 (d, 3H), 1.30 (m, 1H), 1.20 (m, 2H), 1.14–1.06 (m, 9H), 1.15 (s, 3H), 1.11 (d, 3H), 1.05 (d, 3H), 0.91 (t, 3H).

EXAMPLE 61

(11S,11aR)-11-(carboxycyanomethyl)-4"-O-[3-[4-(3-carboxy-1-ethyl-6-fluoro-1,4-dihydro-4-oxo-[1,8]naphthyridinyl)piperazinyl]propionyl]-11-deoxy-6-O-methyl-erythromycin A To a solution of intermediate 81 (20 mg) in anhydrous MeOH (2 mL) 1,4-dihydro-1-ethyl-6-fluoro-4-oxo-7-(piperazin-1-yl)-[1,8]naphthyridine-3-carboxylic acid (21 mg) was added. The reaction mixture was stirred at room temperature overnight, the solvent was evaporated and the residue dissolved in DCM (3 mL). Isocyanate polymer-bound (Aldrich, loading 2 mmol/g, 134 mg) was added and the mixture was shaken at room temperature overnight. The resin was filtered and washed with DCM (3 mL), MeOH (3 mL) and DCM (3 mL). The collected organic extracts were evaporated under reduced pressure. The residue was dissolved in DCM (5 mL) and washed with water (3×3 mL) the combined aqueous phase was extracted with DCM (3×3 mL). The organic phase was dried over $Na_2SO_4$, filtered and concentrated under reduced pressure. The crude material was purified by flash chromatography (eluent DCM/MeOH 90/10) affording the title compound (14 mg).

$^1$H-NMR (500 MHz) δ: 15.00 (bs, 1H), 8.70 (s, 1H), 8.12 (d, 1H), 4.74 (d, 1H), 4.72 (d, 1H), 4.40 (q, 2H), 4.35 (m, 1H), 3.85 (m, 4H), 2.78 (m, 1H), 2.75 (m, 2H), 2.73 (m, 1H), 2.57 (m, 2H), 1.51 (t, 3H).

EXAMPLE 62

(11S,11aR)-11-(carboxycyanomethyl)-4"-O-[3-[[2-[(3-carboxy-1,4-dihydro-1-ethyl-4-oxo-7-quinolinyl)amino]ethyl]amino]propionyl]-11-deoxy-6-O-methyl-erythromycin A A solution of intermediate 81 (100 mg) and intermediate 3 (93 mg) in MeOH (1 mL) was shaken at 70° C. for 16 h. The solvent was evaporated and the residue triturated with DCM (2 mL). The solid was filtered and washed with DCM (1 mL). The mother liquor was concentrated under reduced pressure to give a crude product that was precipitated from EtOAc/n-hexane 1/1 two times affording the title compound (27 mg).

MS; m/z (ES): 1127.1 [MH]$^+$.

EXAMPLE 63

(11S,11aR)-11-(carboxycyanomethyl)-4"-O-[3-[[2-[(3-carboxy-1-cyclopropyl-1,4-dihydro-4-oxo-7-quinolinyl)amino]ethyl]amino]propionyl]-11-deoxy-6-O-methyl-erythromycin A A solution of intermediate 81 (100 mg) and intermediate 4 (97 mg) in MeOH (1 mL) was shaken at 70° C. for 22 h. The solvent was evaporated, the residue was triturated with DCM (2 mL). The solid was filtered and washed with DCM (1 mL). The mother liquor was concentrated under reduced pressure. The crude product was precipitated from EtOAc/n-hexane two times affording the title compound (23 mg).

MS; m/z (ES): 1138.8 [MH]$^+$.

EXAMPLE 64

4"-O-[3-[4-(3-carboxy-1-cyclopropyl-1,4-dihydro-6-fluoro-4-oxo-7-quinolinyl)-1-piperazinyl]propionyl]-roxithromycin To a solution of intermediate 83 (40 mg) in anhydrous MeOH (2 mL), 1-cyclopropyl-1,4-dihydro-6-fluoro-4-oxo-7-(piperazin-1-yl)-quinoline-3-carboxylic acid (50 mg) and DIPEA (0.050 mL) were added. The reaction mixture was stirred at 40° C. overnight, the solvent was evaporated and the residue dissolved in DCM (4 mL). Isocyanate polymer-bound (Aldrich, loading 2 mmol/g, 114 mg) was added and the mixture was shaken at room temperature overnight. The resin was filtered and washed with DCM (4 mL), MeOH (4 mL) and DCM (4 mL). The collected organic extracts were evaporated under reduced pressure. The residue was dissolved in DCM (5 mL) and washed with water (3×3 mL) the combined aqueous phase was extracted with DCM (3×3 mL). The organic phase was dried, filtered and concentrated under reduced pressure. The crude material was purified by flash chromatography (eluent: DCM/MeOH 90/10) affording the title compound (33 mg).

$^1$H-NMR (500 MHz) δ: 15.00 (bs, 1H), 8.78 (s, 1H), 8.03 (d, 1H), 7.35 (d, 1H), 5.18 (dd, 2H), 4.70 (d, 1H), 4.38 (m, 1H), 3.75 (m, 2H), 3.56 (m, 3H), 3.42 (s, 3H), 3.32 (m, 4H), 2.86–2.74 (m, 2H), 2.70 (m, 2H), 2.59 (m, 2H), 1.40 (m, 2H), 1.20 (m, 2H).

EXAMPLE 65

4"-O-[3-[4-(3-carboxy-1-ethyl-6-fluoro-1,4-dihydro-4-oxo-[1,8]naphthyridinyl)piperazinyl]propionyl]-roxithromycin To a solution of intermediate 83 (20 mg) in anhydrous MeOH (2 mL), 1-ethyl-6-fluoro-4-oxo-7-piperazin-1-yl-1,4-dihydro-[1,8]naphthyridine-3-carboxylic acid (21 mg) was added. The reaction mixture was stirred at 40° C. overnight, the solvent was evaporated and the residue dissolved in DCM (3 mL). Isocyanate polymer-bound (Aldrich, loading 2 mmol/g, 128 mg) was added and the mixture was shaken at room temperature overnight. The resin was filtered and washed with DCM (3 mL), MeOH (3 mL) and DCM (3 mL). The collected organic extracts were evaporated under reduced pressure. The residue was dissolved in DCM (5 mL) and washed with water (3×3 mL). The organic phase was dried, filtered and concentrated under reduced pressure. The crude material was purified by flash chromatography (eluent: DCM/MeOH 90/10) affording the title compound (19 mg).

$^1$H-NMR (500 MHz) δ: 15.04 (bs, 1H), 8.70 (s, 1H), 8.12 (d, 1H), 5.18 (d+d, 2H), 4.72 (d, 1H), 4.41 (q, 2H), 4.38 (m, 1H), 3.85 (m, 4H), 3.75 (m, 2H), 3.57 (t, 2H), 3.42 (s, 3H), 2.81–2.54 (m, 6H), 1.51 (t, 3H).

EXAMPLE 66

4"-O-[3-[4-(3-carboxy-7-chloro-1-cyclopropyl-1,4-dihydro-4-oxo-6-quinolinyl)amino]ethyl]amino]propionyl]-roxithromycin To a solution of intermediate 83 (20 mg) in anhydrous i-PrOH (0.5 mL), intermediate 7 (17 mg) and DIPEA (0.030 mL) were added. The reaction mixture was stirred at 120° C. for 2 days, the solvent was evaporated and the residue dissolved in MeOH (3 mL) and stirred overnight at room temperature. The solvent was evaporated and the residue dissolved in DCM (3 mL). 4-Benzyloxybenzaldehyde polymer-bound resin (Aldrich, loading 2.5–3 mmol/g 65 mg) was added and the mixture was shaken at room temperature overnight. The resin was filtered and washed with DCM (3 mL), MeOH (3 mL) and DCM (3 mL). The collected organic extracts were evaporated under reduced pressure. The residue was dissolved in DCM (5 mL) and washed with water (3×3 mL). The organic phase was dried, filtered and concentrated under reduced pressure. The crude material was purified by flash chromatography (eluent: DCM/MeOH 70/30) affording the title compound (9 mg).

$^1$H-NMR (500 MHz) δ: 8.74 (s, 1H), 8.05 (d, 1H), 7.55 (s, 1H), 5.27 (bm, 1H), 5.18 (d+d, 2H), 4.70 (d, 1H), 4.36 (m, 1H), 3.80–3.70 (m, 2H), 3.58–3.53 (m, 3H), 3.42 (s, 3H), 3.40 (m, 2H), 3.02 (m, 2H), 2.98–2.93 (m, 2H), 2.60 (m, 2H), 1.39 (m, 2H), 1.16 (m, 2H).

EXAMPLE 67

4"-O-[3-[4-(3-carboxy-1-cyclopropyl-1,4-dihydro-6-fluoro-4-oxo-7-quinolinyl)amino]ethyl]amino]propionyl]-roxithromycin A mixture of intermediate 8 (0.010 mL) in i-PrOH (2 mL) was left in a ultrasonic bath for 1 minute. Intermediate 83 (20 mg) was added and the reaction mixture was stirred for 6 days at 120° C. The solvent was evaporated under reduced pressure, the residue dissolved in MeOH (4 mL) and the mixture stirred at room temperature overnight. After solvent evaporation the residue was dissolved in DCM (3 mL) and 4-benzyloxybenzaldehyde polymer-bond (Aldrich, loading 2.5–3 mmol/g, 0.14 g) was added. The reaction mixture was shaken at room temperature overnight. The resin was filtered off and washed with DCM (3 mL), MeOH (3 mL), DCM (3 mL); the combined organic extracts were evaporated under reduced pressure. The residue was dissolved in DCM (5 mL) washed with water (3×3 mL). The collected aqueous phase was extracted with DCM (2×5 mL). The organic phase was dried, filtered and concentrated under reduced pressure. The crude material was purified by flash chromatography (eluent: DCM/MeOH 80/20) affording the title compound (7.5 mg).

$^1$H-NMR (500 MHz) δ: 8.73 (s, 1H), 7.98 (d, 1H), 7.00 (d, 1H), 5.48 (bm, 1H), 5.18 (m, 2H), 4.70 (d, 1H), 4.38 (m, 1H), 3.80–3.68 (m, 2H), 3.58–3.46 (m, 3H), 3.42 (s, 3H), 3.42 (m, 2H), 3.05 (m, 2H), 2.98–2.90 (m, 2H), 2.65 (m, 2H), 2.59 (m, 2H), 1.38 (m, 2H), 1.15 (m, 2H).

EXAMPLE 68

4"-O-[2-[[3-[(3-carboxy-7-chloro-1-cyclopropyl-1,4-dihydro-4-oxo-6-quinolinyl)-amino]propyl]amino]ethanoyl]-6-O-methyl-erythromycin A and 4"-O-[2-[[3-[(3-carboxy-1-cyclopropyl-1,4-dihydro-6-fluoro-4-oxo-7-quinolinyl)-amino]propyl]amino]ethanoyl]-6-O-methyl-erythromycin A To a solution of intermediate 70 (100 mg) in anhydrous MeCN (1 mL), intermediates 13 and 14 (mixture, 33 mg) in DMSO (5 mL) were added. The reaction mixture was stirred at room temperature for 2 h and then at 60° C. for 3 h. The reaction mixture was diluted with DCM (10 mL), washed with water (3×100 mL), the organic phase was dried over Na$_2$SO$_4$, filtered and concentrated under reduced pressure. The crude product was purified by flash chromatography (eluent: from DCM to MeOH:DCM 95:5). The compound obtained was diluted in MeOH (0.5 mL) and stirred at room temperature for 2 days. Solvent evaporation under reduced pressure gave the crude compound, which was purified by flash chromatography (eluent: from DCM to MeOH: NH$_4$OH 98:2) to give the title compound (2 mg, mixture of Cl/F derivatives 85/15).

$^1$H-NMR (500 MHz) for 4"-O-[2-[[3-[(3-carboxy-7-chloro-1-cyclopropyl-1,4-dihydro-4-oxo-7-quinolinyl)-amino]propyl]amino]ethanoyl]-6-O-methyl-erythromycin A δ: 15.09 (bs, 1H), 8.74 (d, 1H), 8.03 (s, 1H), 7.54 (s, 1H), 5.72 (bm, 1H), 5.00 (d, 1H), 4.75 (d, 1H), 4.37 (m, 1H), 3.76 (m, 1H), 3.58–3.40 (m, 1H), 3.32 (s, —OCH3), 3.05–2.90 (m, 2H), 2.45 (d, 1H), 2.00 (m, 2H), 1.70 (m, 1H), 1.40–1.12 (m, 10H). $^1$H-NMR (500 MHz) for 4"-O-[2-[[3-[(3-carboxy-1-cyclopropyl-1,4-dihydro-6-fluoro-4-oxo-7-quinolinyl)-amino]propyl]amino]ethanoyl]-6-O-methyl-erythromycin A δ: 15.39 (bs, 1H), 8.73 (d, 1H), 7.96 (d, 1H), 6.91 (s, 1H), 6.24 (bm, 1H). HPLC/MS analysis (mobile phase: A/B from 70/30 to 40/60 in 14 min, from 40/60 to 10/90 in 3 min, 10/90 for 8 min, mass range 150–1000 amu): retention time: 10.4 min (1108 [MH]$^+$) and 11.33 min (1124 [MH]$^+$).

EXAMPLE 69

4"-O-[2-[[2-[(7-chloro-1-cyclopropyl-1,4-dihydro-4-oxo-6-quinolinyl)-amino]ethyl]amino]propionyl]-6-O-methyl-erythromycin A and 4"-O-[2-[[2-[(1-cyclopropyl-6-fluoro-1,4-dihydro-4-oxo-7-quinolinyl)-amino]ethyl]amino]propionyl]-6-O-methyl-erythromycin A To a suspension of intermediate 84 (23 mg) in i-PrOH (1 mL), DBU (0.026 ml) was added and the reaction mixture was heated at 50° C. for 30 min in a sealed tube. Intermediate 68 (50 mg) was added to the reaction mixture, the tube was sealed and the reaction mixture was stirred at 70° C. for 24 h then concentrated under reduced pressure. The crude product was purified by preparative TLC (eluent: DCM/MeOH/NH$_4$OH 90/10/1.5) and then stirred in MeOH (10 mL) at 50° C. for 16 h. Solvent evaporation under reduced pressure gave the title compound (22 mg, a 70/30 mixture of Cl/F derivatives).

$^1$H-NMR (500 MHz) for 4"-O-[2-[[2-[(7-chloro-1-cyclopropyl-1,4-dihydro-4-oxo-7-quinolinyl)-amino]ethyl]

amino]propionyl]-6-O-methyl-erythromycin A δ 7.90 (s, 1H), 7.58 (d, 1H), 7.56 (s, 1H), 6.16 (d, 1H), 4.99 (d, 1H), 4.91 (m, 1H), 4.70 (d, 1H) 4.35 (m, 1H), 3.76 (m, 1H), 3.39–3.331 (m, 3H), 3.31 (s, —OCH3), 3.04–2.95 (m, 4H), 2.61–2.53 (m, 2H), 2.42 (m, 1H), 1.90 (m, 1H), 1.30–1.12 (m, 10H). $^1$H-NMR (500 MHz) for 4"-O-[2-[[2-[(1-cyclopropyl-6-fluoro-1,4-dihydro-4-oxo-7-quinolinyl)amino]ethyl]amino]propionyl]-6-O-methyl-erythromycin A δ7.95 (d, 1H), 7.58 (d, 1H), 6.91 (d, 1H), 6.12 (d, 1H). HPLC/MS analysis (mobile phase: A/B from 70/30 to 45/55 in 20 min, from 45/55 to 10/90 in 5 min, mass range 200–1300 amu): retention time: 17.82 min (1061 [MH]$^+$) and 21.15 min (1078 [MH]$^+$).

EXAMPLE 70

4"-O-[3-[acetyl-[2-[(3-carboxy-7-chloro-1-cyclopropyl-1,4-dihydro-4-oxo-6-quinolinyl)-amino]ethyl]amino]propionyl]-6-O-methyl-erythromycin A To a solution of example 38 (60 mg) in DCM (3 mL), NaHCO$_3$ (42.3 mg) and acetic anhydride (5 µL) were added. The reaction mixture was stirred for 30 min at room temperature. Water (20 mL) was added and the mixture was extracted with DCM (3×10). The organic phase was dried over Na$_2$SO$_4$, filtered and concentrated under reduced pressure to give 56 mg. The crude product (10 mg) was diluted in MeOH (3 mL) and stirred at room temperature for 2 days. Solvent evaporation under reduced pressure gave the crude compound, which was purified by flash chromatography (eluent: DCM/MeOH: 98/2) to give the title compound (9 mg).

HPLC/MS analysis (mobile phase: A/B from 70/30 to 45/55 in 20 min, 45/55 for 10 min, mass range 200–1200 amu): retention time: 24.2 min (1166 [MH]$^+$).

EXAMPLE 71

4"-O-(3-(2-(3-carboxy-7-chloro-1-cyclopropyl-4-oxo-1,4-dihydro-6-quinolinyl)amino)ethyl)-methyl-amino)propionyl)-11,12-dideoxy-11,12-(ethylaminocarbonyloxy)-6-O-methyl-erythromycin A To a solution of example 36 (0.065 g) in chloroform (0.4 mL), was added formaldehyde (0.0159 mL) and formic acid (0.0143 mL). The solution was stirred at room temperature for 2 days. The solvent was then removed in vacuo and the residue subjected to flash chromatography. Evaporation of combined pure fractions afforded 20 mg of pale yellow solid.

FAB-MS m/z 1191 (MH+, 61%).

EXAMPLE 72

4"-O-(3-{[2-(1-cyclopropyl-6-fluoro-3-methoxycarbonyl-4-oxo-1,4-dihydro-quinolin-7-ylamino)-ethyl]-amino}-propionyl)-11,12-dideoxy-6-O-methyl-11,12-(aminocarbonyloxy)-erythromycin A To a solution of intermediate 57 (700 mg) in CH$_3$CN (15 ml), H$_2$O (2 ml) and Et$_3$N (0.5 ml) was added intermediate 85 (540 mg). The reaction mixture was stirred at 60° C. for 18 h. DCM (40 mL) and a saturated solution of NaHCO$_3$ (30 mL) were added to the reaction mixture. The aqueous phase was washed with DCM (30 mL). The combined organic layers were concentrated under reduced pressure and the residue was purified on silica gel using: DCM/MeOH/NH$_4$OH 90/9/0.5 affording the title compound (669 mg).

MS; m/z(ES): 1147.0 [MH]$^+$. $^1$H-NMR (500 MHz, characteristic peaks) δ: 8.50 (s, 1H), 7.92 (bs, 1H), 6.93 (bs, 1H), 5.81 (s, 1H), 5.12 (dd, 2H), 4.97 (d, 1H), 4.70 (d, 1H), 4.54 (d, 1H), 4.35 (m, 1H), 3.91 (s, 3H), 3.81 (d, 1H), 3.68 (m, 2H), 3.61 (d, 1H), 3.31 (s, 1H), 3.18 (dd, 1H), 2.42 (d, 1H), 2.30 (s, 6H), 1.42 (s, 3H), 1.36 (s, 3H), 0.87 (t, 3H).

EXAMPLE 73

4"-O-{3-[(2-[(3-carboxymethyl-7-chloro-1-cyclopropyl-4-oxo-1,4-dihydro-6-quinolinyl)amino]ethyl)amino]propiony}-11,12-dideoxy-6-O-methyl-11,12-(aminocarbonyloxy)-erythromycin A To a solution of intermediate 57 (500 mg) in CH$_3$CN (10 ml), H$_2$O (1 ml) and Et$_3$N (0.2 ml) was added intermediate 10 (410 mg) and the resulting mixture was heated at 70° C. for 5 h. The solvent was evaporated in vacuo and to the residue was added DCM (50 mL). The resulting suspension was filtered and DCM was evaporated in vacuo. The residue was purified on an SPE-column in gradient solvent system DCM/MeOH/NH$_4$OH affording of the title compound (302 mg).

MS; m/z (ES): 1162.5 [MH]$^+$. $^1$H-NMR (500 MHz, characteristic peaks) δ: 8.50 (s, 1H), 7.88 (s, 1H), 7.62 (s, 1H), 5.79 (s, 1H), 5.10 (dd, 2H), 5.00 (t, 1H), 4.97 (d, 1H), 4.70 (d, 1H), 4.54 (d, 1H), 4.33 (m, 1H), 3.91 (s, 3H), 3.80 (d, 1H), 3.68 (m, 2H), 3.60 (d, 1H), 3.44–3.40 (m, 1H), 3.36 (m, 2H), 3.31 (s, 1H), 3.17 (dd, 1H), 2.99 (t, 2H), 2.94 (s, 6H), 2.89–2.84 (m, 1H), 1.41 (s, 3H), 1.18 (d, 2H).

EXAMPLE 74

4"-O-{3-[(2-[(3-carboxymethyl-7-chloro-1-cyclopropyl-4-oxo-1,4-dihydro-6-quinolinyl)amino]ethyl)-methyl-amino]propionyl}-11,12-dideoxy-6-O-methyl-11,12-(aminocarbonyloxy)-erythromycin A To a solution of example 73 (0.300 mg) in CHCl$_3$ (10 mL), formaldehyde (90 mL) and formic acid (60 mL) were added. This mixture was heated at 60° C. over night (18 h). DCM (40 mL) and a saturated solution of NaHCO$_3$ (20 mL) were added to the reaction mixture. The aqueous phase was washed with DCM (2×30 mL). The combined organic layers were concentrated under reduced pressure. The residue was purified on column chromatography on silica gel using: DCM/MeOH/NH$_4$OH 90/5/0.5 affording the title compound (170 mg).

MS; m/z (ES): 1176.93 [MH]$^+$.

EXAMPLE 75

4"-O-(3-{[2-(3-carboxy-1-cyclopropyl-4-oxo-1,4-dihydro-quinolinyl-6-ylamino)-ethyl]-methyl-amino}-propionyl)-11,12-dideoxy-6-O-methyl-11,12-(aminocarbonyloxy)-erythromycin A To a solution of example 113 (230 mg) in MeOH (50 mL), Pd/C 10% (40 mg) was added and the mixture was hydrogenated at room temperature at 5 bar for 3 h. The catalyst was filtered and washed with MeOH and the filtrate was concentrated under reduced pressure. The residue was purified on an SPE-column in gradient solvent system DCM/MeOH/NH$_4$OH affording of the title compounds (156 mg).

MS; m/z (ES): 1128.9 [MH]$^+$.

EXAMPLE 76

4"-O-{3-[(2-[(3-carboxy-1-cyclopropyl-4-oxo-1,4-dihydro-6-quinolinyl)amino]ethyl]amino]propionyl}-11,12-dideoxy-6-O-methyl-11,12-[amino(methyl)carbonyloxy]-erythromycin A To a solution of example 34 (500 mg) in MeOH (60 mL), Pd/C 10% (150 mg) was added and the mixture was hydrogenated at room temperature at 5 bar for 4 h. The catalyst was filtered and washed with MeOH and the filtrate was concentrated under reduced pressure. The residue was crystallised from EtOAc-diisopropyl eter affording the title compound (309 mg). MS; m/z (ES): 1128.72 [MH]$^+$.

EXAMPLE 77

4"-O-{3-[(2-[(3-carboxy-7-chloro-1-cylopropyl-4-oxo-1,4-dihydro-6-quinolinyl)amino]ethyl]methylamino]propionyl}-6-O-methyl-erythromycin A To a solution of example 38 (300 mg) in CHCl$_3$ (6 mL), formaldehyde (40 mL, 35% solution) and formic acid (20 mL) were added. This mixture was heated at 60° C. for 3 h. To the reaction mixture additional amounts of formaldehyde (20 mL) and formic acid (20 mL) were added and the reaction mixture was heated at 60° C. for 7 h. DCM (30 mL) and a saturated solution of NaHCO$_3$ (20 mL) were added to the reaction mixture. The aqueous phase was washed with DCM (15 mL). The combined organic layers were concentrated under reduced pressure. The residue was purified by flash chromatography (eluent: DCM/MeOH/NH$_4$OH 90/5/0.5) affording the title compound (178 mg).

MS; m/z (ES): 1129.2 [MH]$^+$.

EXAMPLE 78

4"-O-{3-[(2-[(3-carboxymethyl-7-chloro-1-cyclopropyl-4-oxo-1,4-dihydro-6-quinolinyl)amino]ethyl)amino]propiony}-6-O-methyl-erythromycin A To a solution of intermediate 69 (500 mg) in CH$_3$CN (10 ml), MeOH (1 ml), H$_2$O (1 ml) and Et$_3$N (0.2 ml) was added intermediate 10 (420 mg) and the resulting mixture was heated at 60° C. for 24 hours. The solvent was evaporated in vacuo and to the residue was added DCM (50 mL). The resulting suspension was filtered and DCM was evaporated in vacuo. The residue was purified on an SPE-column in gradient solvent system DCM/MeOH/NH$_4$OH affording of the title compound (382 mg).

MS; m/z (ES): 1137.50 [MH]$^+$.

EXAMPLE 79

4"-{3-[(2-[(3-carboxy-1-methyl-1,4-dihydro-4-oxo-7-quinolinyl)amino]ethyl)amino]propionyl}-6-O-methyl-erythromycin A To a solution of intermediate 69 (100 mg) in i-PrOH (2 mL), intermediate 87 (98 mg) was added and shaken at 80° C. for 41 hours. The solvent was evaporated, and the residue was triturated with DCM (2 mL). The resulting suspension was filtered and washed with DCM (1 mL). The filtrate was concentrated in vacuo. The crude product was precipitated from EtOAc-n-hexane twice affording the title compound (25 mg).

MS (ES+) m/z: [MH]$^+$=1063.8.

EXAMPLE 80

4"-{3-[(2-[(3-carboxy-1-cyclopropyl-1,4-dihydro-4-oxo-7-quinolinyl)amino]butyl)amino]propionyl}-6-O-methyl-erythromycin A To solution of intermediate 69 (170 mg) in MeOH (2 mL), intermediate 9 (200 mg) was added and shaken at 70° C. for 24 hours. The solvent was evaporated, and the residue was triturated with DCM (2 mL). The resulting suspension was filtered and washed with DCM (1 mL). The filtrate was concentrated in vacuo. The crude product was precipitated from EtOAc-n-hexane twice affording the title compound (65 mg).

MS (ES+) m/z: [MH]$^+$=1117.8.

EXAMPLE 81

4"-O-{[(2-[(3-carboxy-1-ethyl-1,4-dihydro-4-oxo-7-quinolinyl)amino]ethyl)methylamino]propionyl}-6-O-methyl-erythromycin A To a solution of example 39 (170 mg) in chloroform (2 ml), a 36% solution of HCOH (0.0254 ml) and HCOOH (0.0250 ml) was added and the reaction mixture was shaken at 65° C. for 21 hours. The reaction mixture was evaporated yielding 190 mg of product, which was purified by column chromatography (SPE-column, gradient polarity: 100% DCM to DCM:MeOH:NH3=90:9:1.5) yielding 105 mg of impure product. Precipitation from EtOAc:n-hexane yielded pure title compound (83 mg).

MS (ES+) m/z: [MH]$^+$=1105.5.

EXAMPLE 82

4"-O-{[(2-[(3-carboxy-1-cyclopropyl-1,4-dihydro-4-oxo-7-quinolinyl)amino]ethyl)methylamino]propionyl}-6-O-methyl-erythromycin A To a solution of example 40 (150 mg) in chloroform (2 ml), a 36% solution of HCOH (0.021 ml) and HCOOH (0.019 ml) was added and the reaction mixture was shaken at 65° C. for 2 hours. The reaction mixture was evaporated yielding 150 mg of product, which was purified by column chromatography (SPE-column, gradient polarity: 100% DCM to DCM:MeOH:NH3=90:9:1.5) yielding 90 mg of impure product. Precipitation from EtOAc:n-hexane yielded pure title compound (65 mg).

MS (ES+) m/z: [MH]$^+$=1119.3.

EXAMPLE 83

4"-O-{3-[(2-[(3-carboxy-1-cyclopropyl-1,4-dihydro-4-oxo-7-quinolinyl)amino]butyl)amino]propiony}-6-O-methyl-8a-aza-8a-homoerythromycin A To a solution of intermediate 26 (100 mg) in i-PrOH (1 mL), intermediate 9 (116 mg) was added and shaken at 80° C. for 19 hours. The solvent was evaporated, and the residue was triturated with DCM (2 mL). The resulting suspension was filtered and washed with DCM (1 mL). The filtrate was concentrated in vacuo. The crude product was precipitated from EtOAc-n-hexane twice affording the title compound (57 mg).

MS (ES+) m/z: [MH]$^+$=1132.3.

EXAMPLE 84

4"-O-{3-[(2-[(3-carboxy-1-methyl-1,4-dihydro-4-oxo-7-quinolinyl)amino]ethyl)amino]propionyl}-6-O-methyl-8a-aza-8a-homoerythromycin A To solution of intermediate 26 (100 mg) in i-PrOH (1 mL), intermediate 87 (96 mg) was added and shaken at 60° C. for 43 hours. The solvent was evaporated, and the residue was triturated with DCM (2 mL). The resulting suspension was filtered and washed with DCM (1 mL). The filtrate was concentrated in vacuo. The crude product was precipitated from EtOAc-n-hexane the residue purified on a $SiO_2$ SPE-column (eluent: from DCM 100% to DCM:MeOH:$NH_4OH$ 85/13/2) giving the title compound (5 mg).
MS (ES+) m/z: $[MH]^+$=1077.9.

EXAMPLE 85

11,12-(aminocarbonyloxy)-4"-O-{3-[(2-[(3-carboxy-1-ethyl-4-oxo-1,4-dihydro-7-quinolinyl)amino]ethyl)amino]propionyl}-11,12-dideoxy-6-O-methyl-erythromycin A To solution of intermediate 57 (100 mg) in $CH_3CN$ (3 mL), intermediate 3 (96 mg) was added and shaken at 80° C. for 72 hours. The solvent was evaporated, and the residue was triturated with EtOAc (5 mL). The resulting suspension was filtered and washed with EtOAc (1 mL). The filtrate was concentrated in vacuo. The crude product was precipitated from EtOAc-n-hexane twice giving the title compound (25 mg).
MS (ES+) m/z: $[MH]^+$=1102.8.

EXAMPLE 86

4"-O-{3-[(2-[(3-carboxy-1-ethyl-1,4-dihydro-4-oxo-7-quinolinyl)amino]ethyl)amino]propionyl}-11,12-dideoxy-11,12-(methylaminocarbonyloxy)-6-O-methyl-erythromycin A To solution of intermediate 59 (57 mg) in MeOH (1 mL), intermediate 3 (67 mg) was added and shaken at 65° C. for 24 hours. The solvent was evaporated, and the residue was triturated with EtOAc (3 mL). The resulting suspension was filtered and washed with EtOAc (1 mL). The filtrate was concentrated in vacuo. The crude product was precipitated from EtOAc-n-hexane twice giving the title compound (17 mg).
MS (ES+) m/z: $[MH]^+$=1116.7.

EXAMPLE 87

4"-O-{3-[(2-[(3-carboxy-1-ethyl-1,4-dihydro-4-oxo-7-quinolinyl)amino]ethyl)amino]propionyl}-11,12-dideoxy-11,12-(ethylaminocarbonyloxy)-6-O-methyl-erythromycin A To solution of intermediate 64 (100 mg) in MeOH (1 mL), intermediate 3 (64 mg) was added and shaken at 65° C. for 24 hours. The solvent was evaporated, and the residue was triturated with EtOAc (3 mL). The resulting suspension was filtered and washed with EtOAc (1 mL). The filtrate was concentrated in vacuo. The crude product was precipitated from EtOAc-n-hexane twice giving the title compound (42 mg).
MS (ES+) m/z: $[MH]^+$=1130.7.

EXAMPLE 88

11,12-(aminocarbonyloxy)-4"-O-{3-[(2-[(3-carboxy-1-cyclopropyl-4-oxo-1,4-dihydro-6-quinolinyl)amino]ethyl)amino]propionyl}-11,12-dideoxy-6-O-methyl-erythromycin A The pH value of a solution of example 32 (150 mg) in MeOH (30 mL) was adjusted to 5.5 by 1N HCl, 10% Pd/C (75 mg) was added and the reaction mixture was hydrogenated at 10 bar pressure for 22 hours at room temperature. The solvent was evaporated, water was added and the pH was adjusted to 9.5 with 2N NaOH. The aqueous layer was extracted with DCM (3×30 mL), the organic layer dried over $Na_2SO_4$ and evaporated. The crude product was precipitated from EtOAc-n-hexane giving the title compound (35 mg).
MS (ES+) m/z: $[MH]^+$=1114.8.

EXAMPLE 89

11,12-(aminocarbonyloxy)-4"-O-{[(2-[(3-carboxy-1-cyclopropyl-1,4-dihydro-6-fluoro-4-oxo-7-quinolinyl)amino]ethyl)methylamino]propionyl}-11,12-dideoxy-6-O-methyl-erythromycin A To a solution of example 33 (100 mg) in chloroform (2 ml), 36% solution of HCHO (0.0136 ml) and HCOOH (0.0123 ml) was added and shaken at 65° C. for 20 hours. The reaction mixture was evaporated yielding 120 mg of a complex mixture. The residue was purified by column chromatography (SPE-column, gradient polarity: 100% DCM to DCM:MeOH:NH3=90:9:1.5) yielding 20 mg of impure product. Precipitation from EtOAc:n-hexane yielded pure title compound (7 mg).
MS (ES+) m/z: $[MH]^+$=1147.0.

EXAMPLE 90

4"-O-[3-[[2-[(3-carboxy-1-cyclopropyl-1,4-dihydro-4-oxo-7-quinolinyl)amino]ethyl]amino]propionyl]-azithromycin To a suspension of intermediate 51 (100 mg) in methanol (3 mL), intermediate 4 (72 mg) was added. This mixture was heated at 60° C. for 24 h. The solvent was evaporated and the residue purified by flash chromatography (eluent: DCM/MeOH/$NH_3$ 90/9/1.5) affording the title compound (13 mg).
MS; m/z (ES): $[MH]^+$. 1090.3.

EXAMPLE 91

4"-O-[3-[[2-[(3-carboxy-1-methyl-1,4-dihydro-4-oxo-7-quinolinyl)amino]ethyl]amino]propionyl]-azithromycin To a suspension of intermediate 51 (100 mg) in methanol (3 mL), intermediate 87 (65 mg) was added. This mixture was heated at 60° C. for 24 h. The solvent was evaporated and the residue purified by flash chromatography (eluent: DCM/MeOH/$NH_3$ 90/9/1.5) affording the title compound (22 mg).
MS; m/z (ES): $[MH]^+$. 1064.2.

EXAMPLE 92

4"-O-[3-[[2-[(3-carboxy-1-cyclopropyl-1,4-dihydro-4-oxo-7-quinolinyl)amino]butyl]amino]propionyl]-azithromycin To a suspension of intermediate 51 (100 mg) in methanol (3 mL), intermediate 9 (78 mg) was added. This mixture was heated at 60° C. for 24 h. The solvent was evaporated and the residue purified by flash chromatography (eluent: DCM/MeOH/NH$_3$ 90/9/1.5) affording the title compound (24 mg).
MS; m/z(ES): [MH]$^{30}$. 1118.5.

EXAMPLE 93

4"-O-[3-[[2-[(3-carboxy-7-chloro-1-cyclopropyl-1,4-dihydro-4-oxo-6-quinolinyl)amino]ethyl]-methylamino]propionyl]-azithromycin To a suspension of example 28 (500 mg) in chloroform (15 mL), a 36% aqueous solution of formaldehyde (0.150 mL) and formic acid (0.11 mL) were added. This mixture was stirred at room temperature for 48 h. Saturated NaHCO$_3$ (20 mL) was then added. The layers were separated, and the aqueous layer was washed with CH$_2$Cl$_2$ (2×10 mL). The combined organic layers were dried and concentrated under reduced pressure. The residue was dissolved in EtOAc (10 mL) and the product precipitated by adding n-hexane (40 mL) affording the title compound (370 mg).
MS; m/z (ES): [MH]$^+$. 1138.6. $^{13}$C-NMR (75 MHz) δ: 178.8; 177.6; 171.8; 167.4; 145.8; 143.2; 132.5; 127.6; 126.4; 17.9; 107.6; 104.5; 102.4; 94.8; 83.3; 78.9; 77.9; 77.5; 74.3; 73.9; 73.6; 73.0; 71.0; 70.1; 67.8; 65.6; 62.9; 62.4; 55.4; 52.9; 49.5; 45.1; 42.3; 41.9; 41.3; 40.7; 40.4; 36.4; 35.3; 35.1; 32.7; 27.5; 26.8; 21.9; 21.8; 21.3; 21.3; 17.9; 16.2; 14.7; 11.3; 9.2; 8.1; 7.5.

EXAMPLE 94

11,12-carbonate-4"-O-[3-[[2-[(3-carboxy-1-cyclopropyl-1,4-dihydro-6-fluoro-4-oxo-7-quinolinyl)amino]ethyl]methylamino]propionyl]-11,12-dideoxy-azithromycin Example 26 (150 mg) was dissolved in CHCl$_3$ (10 mL), then formaldehyde (0.034 mL, 36%) and formic acid (0.031 mL) were added and reaction mixture was stirred at 60° C. for 4 h. The solvent was removed under reduced pressure and the residue purified by silicagel column (eluent: CHCl$_3$-MeOH—NH$_4$OH=6:1:0.1) giving the title compound (47 mg).
MS; m/z (ES): 1147 [MH]$^+$.

EXAMPLE 95

11,12-carbonate-4"-O-[3-[[2-[(3-carboxy-1-cyclopropyl-1,4-dihydro-7-chloro-4-oxo-6-quinolinyl)amino]ethyl]methylamino]propionyl]-11,12-dideoxy-azithromycin Example 25 (910 mg) was dissolved in CHCl$_3$ (62 mL), then formaldehyde (0.05 mL, 36%) and formic acid (0.045 mL) were added and reaction mixture was stirred at reflux temperature for 6 h. Solvent was evaporated and the residue purified by silicagel column (eluent: CHCl$_3$-MeOH—NH$_4$OH=6:1:0.1) affording the title compound (390 mg).
MS; m/z (ES): 1164.6 [MH]$^+$.

EXAMPLE 96

11,12-carbonate-4"-O-[3-[[2-[(3-carboxy-1-cyclopropyl-1,4-dihydro-4-oxo-6-quinolinyl)amino]ethyl]methylamino]propionyl]-11,12-dideoxy-azithromycin Example 95 (500 mg) was dissolved in MeOH (70 mL), Pd/C (300 mg, 10%) was added and hydrogenation was performed at 3×10$^5$ Pa for 4 h. The catalyst was filtered off and the filtrate was evaporated under reduced pressure. The crude product was precipitated from DCM/n-hexane affording the title compound (350 mg).
MS; m/z (ES): 1130 [MH]$^+$.

EXAMPLE 97

11,12-carbonate-4"-O-[3-[[2-[(3-carboxy-1-cyclopropyl-1,4-dihydro-4-oxo-6-quinolinyl)amino]ethyl]amino]propionyl]-11,12-dideoxy-azithromycin Example 25 (100 mg) was dissolved in MeOH (8 mL), Pd/C (60 mg, 10%) was added and hydrogenation was performed at 4×10$^5$ Pa for 3 h. The catalyst was filtered off and the filtrate was evaporated under reduced pressure. The residue was purified by silicagel column [eluent: DMC-(MeOH—NH$_4$OH=9:1.5)=90:15] affording the title compound (32 mg).
MS; m/z (ES): 1116 [MH]$^+$.

EXAMPLE 98

11,12-carbonate-4"-O-[3-[[2-[(3-carboxy-1-ethyl-1,4-dihydro-4-oxo-7-quinolinyl)amino]ethyl]amino]propionyl]-11,12-dideoxy-azithromycin To solution of intermediate 50 (200 mg) in MeOH (2 mL), intermediate 3 (200 mg) was added and reaction mixture stirred at 65° C. for 24 h. After evaporation of the solvent, the residue was suspended in DCM, filtered off and the filtrate was evaporated to give the crude product (160 mg). The residue was purified by silicagel column (CHCl$_3$-MeOH—NH$_4$OH=6:1:0.1). After crystallisation from EtOAc/n-hexane the title compound was obtained (50 mg).
MS; m/z (ES): 1104 [MH]$^+$.

EXAMPLE 99

4"-O-{3-[(2-[3-carboxy-6-fluoro-8-methoxy-1-cyclopropyl-4-oxo-1,4-dihydro-7-(quinolinyl)amino]ethyl)amino]propionyl}-azithromycin To a suspension of intermediate 51 (500 mg) in acetonitrile (12 ml), intermediate 88 (417 mg), 0.5 ml of water and 0.25 ml of DBU were added. This mixture was heated at 85° C. and stirred for 24 h. The solvent was evaporated under reduced pressure and residue was purified on SiO$_2$ SPE-column (eluent: from DCM 100% to DCM/MeOH/NH$_4$OH=85/13/12) affording the title product.
MS; m/z (ES): 1139.6 [MH]$^+$.

EXAMPLE 100

4"-O-{3-[(2-[3-carboxy-6-fluoro-8-methoxy-1-cyclopropyl-4-oxo-1,4-dihydro-7-(quinolinyl)amino] ethyl)amino]propionyl}-6-O-methyl-erythomycin To the suspension of intermediate 69 in acetonitrile (6 ml), intermediate 88 (230 mg), 0.25 ml of water and 0.08 ml of triethylamine were added. This mixture was heated at 85° C. and stirred for 48 h. The solvent was evaporated under reduced pressure and residue was purified on $SiO_2$ SPE-column (eluent: from DCM 100% to DCM/MeOH/$NH_4OH$=85/13/12) affording the title product.
MS; m/z (ES): 1138.6 [MH]$^+$.

EXAMPLE 101

4"-O-(3-{[2-(7-chloro-1-cyclopropyl-3-methoxycarbonyl-4-oxo-1,4-dihydro-quinolin-6-ylamino)-ethyl]-amino}-propionyl)-azithromycin To a solution of intermediate 51 (300 mg) in MeOH (5 ml) was added intermediate 10 (376 mg) and the resulting mixture was heated at 60° C. for 24 hours. The solvent was evaporated in vacuo and to the residue was added DCM (50 mL). The resulting suspension was filtered and DCM was evaporated in vacuo. The residue was purified on an SPE-column in gradient solvent system DCM/MeOH/$NH_4OH$ affording the title compound (99 mg).
MS; m/z (ES): 1138.06 [MH]$^+$. $^1$H-NMR (selected peaks, 500 MHz) δ 8.50 (s, 1H), 7.87 (s, 1H), 7.58 (s, 1H), 5.19 (d, 1H), 5.08 (t, 1H), 4.89 (m, 1H), 4.71 (d+m, 2H), 4.56 (d, 1H), 4.41 (m, 1H), 4.26 (m, 1H), 3.91 (s, 3H), 3.78 (m, 1H), 3.68 (m, 1H), 3.61 (d, 1H), 3.43 (m, 1H), 3.38 (m, 2H), 3.31 (s, 3H), 3.01 (t, 2H), 2.75 (m, 1H).

EXAMPLE 102

4"-O-(3-{[2-(7-chloro-1-cyclopropyl-3-methoxycarbonyl-4-oxo-1,4-dihydro-quinolin-6-ylamino)-ethyl]-methyl-amino}-propionyl)-azithromycin To a solution of example 101 (150 mg) in CHCl$_3$ (6 mL), formaldehyde (90 mL) and formic acid (60 mL) were added. This mixture was heated at 60° C. for 3 h. To the reaction mixture DCM (40 mL) and a saturated solution of NaHCO$_3$ (20 mL) were added. The aqueous phase was washed with DCM (15 mL). The combined organic layers were concentrated under reduced pressure. The residue was purified on column chromatography on silica gel using: DCM/MeOH/$NH_4OH$ 90/5/0.5 affording the title compound (90 mg).
MS; m/z (ES): 1152.47 [MH]$^+$. $^1$H-NMR (selected peaks, 500 MHz) δ 8.50 (s, 1H), 7.89 (s, 1H), 7.60 (s, 1H), 5.19 (d, 1H), 5.12 (t, 1H), 4.82 (m, 1H), 4.72 (d, 1H), 4.71 (m, 1H), 4.57 (d, 1H), 4.41 (m, 1H), 4.27 (m, 1H), 3.91 (s, 3H), 3.63 (d, 1H), 3.43 (m, 1H), 3.32 (s, 3H), 2.39 (d, 1H), 2.32 (s, 6H), 2.27 (s, 3H), 1.76 (d, 1H), 1.64 (dd, 1H), 1.50–1.44 (m, 1H), 0.90 (d, 3H), 0.88 (t, 3H).

EXAMPLE 103

4"-O-(3-{[2-(1-cyclopropyl-3-methoxycarbonyl-4-oxo-1,4-dihydro-quinolin-6-ylamino)-ethyl]-amino}-propionyl)-azithromycin To a solution of example 101 (150 mg) in MeOH (30 mL), Pd/C 10% (40 mg) was added and the mixture was hydrogenated at room temperature at 5 bar for 3.5 h. The catalyst was filtered and washed with MeOH and the filtrate was concentrated under reduced pressure. The residue was purified on an SPE-column in gradient solvent system DCM/MeOH/$NH_4OH$ affording the title compound (90 mg).
MS; m/z (ES): 1105.0 [MH]$^+$.

EXAMPLE 104

4"-O-{3-[2-(1-cyclopropyl-6-fluoro-3-methoxycarbonyl-4-oxo-1,4-dihydro-quinolin-7-ylamino)-ethylamino]-propionyl}-azithromycin To a solution of intermediate 51 (580 mg) in MeOH (14 ml) and H$_2$O (1 ml) was added intermediate 85 (550 mg). The reaction mixture was stirred at 60° C. for 18 h. The solvent was concentrated under reduced pressure and the residue was purified on an SPE-column in gradient solvent system DCM/MeOH/$NH_4OH$ affording the title compound (180 mg).
MS; m/z (ES): 1122.44 [MH]$^+$.

EXAMPLE 105

4"-O-{3-[(2-[(3-carboxy-1-ethyl-1,4-dihydro-4-oxo-7-quinolinyl)amino]ethyl)amino]propionyl}-azithromycin To solution of intermediate 51 (300 mg) in i-PrOH (3 mL), intermediate 3 (205 mg) was added and shaken at 65° C. for 4 days. The solvent was evaporated, and the residue was triturated with EtOAc (2 mL). The resulting suspension was filtered and washed with EtOAc (1 mL). The filtrate was concentrated in vacuo. The crude product was precipitated from EtOAc-n-hexane affording the title compound (250 mg).
MS (ES+) m/z: [MH]$^+$=1078.9.

EXAMPLE 106

4"-O-{3-[(2-[(3-carboxy-1-cyclopropyl-1,4-dihydro-4-oxo-6-quinolinyl)amino]ethyl)amino]propionyl}-azithromycin The pH value of a solution of example 28 (138 mg) in MeOH (30 mL) was adjusted to 5.5 by 1N HCl, 10% Pd/C (70 mg) was added and the reaction mixture was hydrogenated at 10 bar pressure for 18 hours at room temperature. The solvent was evaporated, water was added and the pH was adjusted to 9.5 with 2N NaOH. The aqueous layer was extracted with DCM (3×30 mL), the organic layer dried over Na$_2$SO$_4$ and evaporated. The crude product was purified by a silica gel SPE-column (eluent: from DCM 100% to DCM/MeOH/$NH_4OH$ 90/91/1.5) and then precipitated from EtOAc:n-hexane giving the title compound (15 mg).
MS (ES+) m/z: [MH]$^+$=1090.9.

EXAMPLE 107

4"-O-{3-[(2-[(3-carboxy-1-cyclopropyl-6-fluoro-1,4-dihydro-4-oxo-7-quinolinyl)amino]ethyl)amino] propionyl}-azithromycin To a solution of intermediate 51 (100 mg) in i-PrOH (3 mL), intermediate 8 (114 mg), triethylamine (0.200 mL) and water (0.200 mL) were added and shaken at 65° C. for 24 hours. The solvent was evaporated, and the residue was trituated with EtOAc (3 mL). The resulting suspension was filtered and washed with EtOAc (1 mL). The filtrate was concentrated in vacuo. The crude product was precipitated from EtOAc:n-hexane twice giving the title compound (20 mg).

MS (ES+) m/z: [MH]⁺=1122.7.

EXAMPLE 108

4"-O-{3-[(2-[(3-carboxy-1-ethyl-1,4-dihydro-4-oxo-7-quinolinyl)amino]ethyl)methylamino]propionyl}-azithromycin To a solution of example 105 (250 mg) in chloroform (3 ml), a 36% solution of HCOH (0.036 ml) and HCOOH (0.032 ml) was added and shaken at 60° C. for 18 hours. The reaction mixture was evaporated and the residue purified by column chromatography (SPE-column, gradient polarity: 100% DCM to DCM:MeOH:NH3=90:9:1.5) yielding 80 mg of pure product. Precipitation from EtOAc:n-hexane yielded title compound (30 mg).

MS (ES+) m/z: [MH]⁺=1092.8.

EXAMPLE 109

4"-O-{3-[(2-[(3-carboxy-1-cyclopropyl-1,4-dihydro-4-oxo-7-quinolinyl)amino]ethyl)methylamino]propionyl}-azithromycin To a solution of example 90 (70 mg) in chloroform (3 ml), a 36% solution of HCHO (0.011 ml) and HCOOH (0.009 ml) was added and shaken at 60° C. for 7 hours. The reaction mixture was evaporated and the residue purified by column chromatography (SPE-column, gradient polarity: 100% DCM to DCM:MeOH:NH3=90:9:1.5) yielding 45 mg of unpure product. Precipitation from EtOAc:n-hexane yielded pure title compound (23 mg).

MS (ES+) m/z: [MH]⁺=1105.2.

EXAMPLE 110

4"-O-{3-[(2-[(3-carboxy-1-cyclopropyl-1,4-dihydro-4-oxo-6-quinolinyl)amino]ethyl)methylamino]propionyl}-azithromycin To a solution of example 93 (0.53 g) in MeOH (50 ml), 10% Pd/C (0.19 g) was added and shaken in Parr apparatus at 5 bars at r.t. for 3 hours. The catalyst was filtered, the solvent evaporated and the residue precipitated from EtOAc: n-hexane yielding 0.5 g of crude product. Purification by column chromatography (SPE-column, gradient polarity: 100% DCM to DCM:MeOH:NH3=90:9:1.5) yielded 0.2 g product which was precipitated from EtOAc:n-hexane yielding pure title compound (0.13 g).

MS (ES+) m/z: [MH]⁺=1104.4.

EXAMPLE 111

4"-O-{3-[(2-[(3-carboxy-1-cyclopropyl-1,4-dihydro-6-fluoro-4-oxo-7-quinolinyl)amino]ethyl)methylamino]propionyl}-azithromycin To a solution of example 107 (150 mg) in chloroform (3 ml), a 36% solution of HCHO (0.022 ml) and HCOOH (0.020 ml) was added and shaken at 60° C. for 17 hours. The reaction mixture was evaporated and the residue purified by column chromatography (SPE-column, gradient polarity: 100% DCM to DCM:MeOH:NH3=90:9:1.5) yielding 85 mg of impure product. Precipitation from EtOAc:n-hexane yielded pure title compound (30 mg).

MS (ES+) m/z: [MH]⁺=1123.0.

EXAMPLE 112

4"-O-{3-[(2-[(3-carboxy-1-cyclopropyl-6-fluoro-4-oxo-1,4-dihydro-7-quinolinyl)amino]ethyl)amino]propiony}-11,12-dideoxy-6-O-methyl-11,12-(methylaminocarbonyloxy)-erythromycin A To a solution of intermediate 59 (600 mg) in acetonitrile (15 ml) was added intermediate 8 (310 mg) and the resulting mixture was heated at 80° C. for 22 hours. The solvent was evaporated in vacuo, MeOH (50 mL) was added to the residue and the mixture was heated at 60° C. for 18 hours. The reaction suspension was filtered and the solvent was evaporated in vacuo. The resulting residue was dissolved in EtOAc (30 ml) and filtered. The residue was crystallised twice from EtOAc-diisopropylether affording the title compound (167 mg).

MS; m/z (ES): 1146.48 [MH]⁺.

EXAMPLE 113

11,12-(aminocarbonyloxy)-4"-O-(3-{[2-(3-carboxy-7-chloro-1-cyclopropyl-4-oxo-1,4-dihydro-quinolin-6-ylamino)ethyl]-methyl-amino}-propionyl)-11,12-dideoxy-6-O-methyl-erythromycin A To a solution of example 32 (100 mg) in chloroform (1.5 mL) at room temperature HCHO (13 μL) and HCOOH (12.1 μL) were added and the mixture was stirred at 60° C. for 20 hours. The solvent was evaporated under reduced pressure, and the residue was dissolved in EtOAc (30 ml) and extracted with 10% aqueous solution of NaHCO₃ (30 ml). The organic layer was concentrated under reduced pressure. The residue was precipitated from ethyl acetate/diisopropyl ether yielding the title compound (68 mg).

MS; m/z (ES): 1162.8 [MH]⁺.

EXAMPLE 114

4"-O-[3-[[2-[(3-carboxy-7-chloro-1-ethyl-1,4-dihydro-4-oxo-6-quinolinyl)amino]ethyl]amino]propionyl]-6-O-methyl-erythromycin A To a solution of intermediate 69 (100 mg) in 5 ml 2-PrOH, intermediate 5 (77 mg) was added and stirred at 80° C. for 9 days. The reaction was not complete so water (0.5 ml) was added and stirring continued. After a further 3 hours the reaction was still not complete so 0.1 ml of triethylamine was added and stirring continued for 3 days at 90° C. MS showed that the reaction was then complete. The reaction mixture was evaporated and the residue dissolved in EtOAc and filtered. The dissolved residue was precipitated with n-hexane to give the title compound (91 mg).

MS; m/z(ES): 1111.5 [MH]⁺.

EXAMPLE 115

4"-O-[3-[[2-[(3-carboxy-7-chloro-1-ethyl-1,4-dihydro-4-oxo-6-quinolinyl)amino]ethyl]amino]propionyl]-azithromycin To a solution of intermediate 51 (100 mg) in 5 ml 2-PrOH, intermediate 5 (77 mg) was added and stirred at 80° C. for 9 days. The reaction was not complete so water (0.5 ml) was added and stirring continued. After a further 3 hours the reaction was still not complete so 0.1 ml of triethylamine was added and stirring continued for 3 days at 90° C. MS showed that the reaction was then complete. The reaction mixture was evaporated and the residue dissolved in EtOAc and filtered. The dissolved residue was precipitated with n-hexane to give the title compound (89 mg).

MS; m/z (ES): 1112.5 [MH]$^+$.

EXAMPLE 116

4"-O-[3-[[2-[(3-carboxy-1-ethyl-1,4-dihydro-4-oxo-6-quinolinyl)amino]ethyl]amino]propionyl]-6-O-methyl-erythromycin A Example 114 (50 mg) was dissolved in 25 ml methanol and catalyst (10% Pd/C, 25 mg) was added. The pH was adjusted to 6.0 and the mixture was shaken under hydrogen (5 bar) overnight. MS showed no starting material. The mixture was filtered, the pH was adjusted to 8.9 and the solvent was evaporated. The residue was dissolved in DCM (100 ml) and washed with NaHCO$_3$ (aq). The DCM was evaporated and 38 mg of crude product was obtained. After SPE (1 g) purification, the title compound (13 mg) was obtained.

MS; m/z (ES): 1077.8 [MH]$^+$.

EXAMPLE 117

4"-O-[3-[[2-[(3-carboxy-1-ethyl-1,4-dihydro-4-oxo-6-quinolinyl)amino]ethyl]amino]propionyl]-azithromycin Example 115 (50 mg) was dissolved in 25 ml of methanol and catalyst (10% Pd/C, 25 mg) was added. The pH was adjusted to 6.0 and the mixture was shaken under hydrogen (5 bar) overnight. MS showed no starting material. The mixture was filtered, the pH was adjusted to 8.9 and the solvent was evaporated. The residue was dissolved in DCM (100 ml) and washed with NaHCO$_3$ (aq). The DCM was evaporated and 36 mg of crude product was obtained. After SPE (1 g) purification, the title compound (9 mg) was obtained.

MS; m/z (ES): 1078.8 [MH]$^+$.

EXAMPLE 118

4"-O-[3-[(2-[(1-benzyl-3-carboxy-1,4-dihydro-4-oxo-7-quinolinyl)amino]ethyl]amino]propionyl]-6-O-ethyl-8a-aza-8a-homoerthromycin A To a solution of intermediate 30 (100 mg) in i-PrOH (5 mL) was added intermediate 2 (70 mg). The resulting mixture was stirred at 80° C. for 10 days. The solvent was evaporated under reduced pressure, MeOH (3 mL) was added, stirred at 80° C. for 3 h, evaporated and the crude product was purified by flash chromatography (eluent: MeOH/DCM/NH$_4$OH 9/90/1.5) affording the title compound (5 mg).

MS; m/z (ES): 1168.8 [MH]$^+$.

EXAMPLE 119

4"-O-[3-[(2-[(1-benzyl-3carboxy-1,4-dihydro-4-oxo-7-quinolinyl)amino]ethyl]amino]propionyl]-6-O-propyl-8a-aza-8a-homoerythromycin A To a solution of intermediate 35 (100 mg) in i-PrOH (5 mL) was added intermediate 2 (70 mg). The resulting mixture was stirred at 80° C. for 10 days. The solvent was evaporated under reduced pressure, MeOH (3 mL) was added, stirred at 80° C. for 3 h, evaporated and the crude product was purified by flash chromatography (eluent: MeOH/DCM/NH$_4$OH 9/90/1.5) affording the title compound (6 mg).

MS; m/z (ES): 1182.5 [MH]$^+$.

Biological Data

The MIC (μg/ml) of test compounds against various organisms was determined including: *S. aureus* Smith ATCC 13709, *S. pneumoniae* SP030, *S. pyogenes* 3565, *E. faecalis* ATCC 29212, *H. influenzae* ATCC 49247, and *M. catarrhalis* ATCC 23246.

Examples 1–4, 6–8, 10–11, 13–15, 21–26, 28–39, 41–50, 53–63, 66–81, 85–91, 93, 95–97, 99–101, 104–107 and 109–115 have an MIC ≦1 μg/ml against *S. aureus* Smith ATCC 13709, *S. pneumoniae* SP030, *S. pyogenes* 3565 and *E. faecalis* ATCC 29212.

Examples 3, 6–7, 17, 25, 28, 32, 34, 36, 38–42, 45, 52–53, 75–76, 78, 81–82, 88, 93, 95–111 and 114–116 have an MIC ≦2 μg/ml against *H. influenzae* ATCC 49247 and *M. catarrhalis* ATCC 23246.

Examples 1–5, 11–15, 17–18, 20, 25–28, 32–36, 38–42, 45, 49–53, 56, 58, 62–63, 71, 73–74, 76, 78, 81–82, 85–88, 90–93, 95–97, 99–101, 107, 109 and 112–113 have an MIC <0.25 μg/ml against erythromycin resistant strains of *Streptococcus pneumoniae* and *Streptococcus pyogenes*.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:
1. A compound of formula (I)

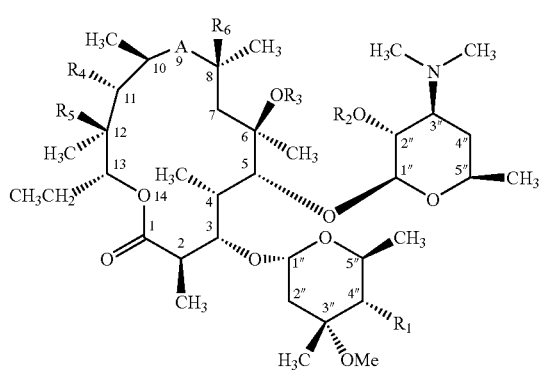

wherein
A is a bivalent radical selected from:
—C(O)—, —C(O)NH—, —NHC(O)—, —N(CH$_3$)—CH$_2$—, —CH$_2$—N(CH$_3$)— and —C(NOCH$_2$OCH$_2$CH$_2$OCH$_3$)—;
R$_1$ is OC(O)(CH$_2$)$_n$XR$_7$;
R$_2$ is hydrogen or a hydroxyl protecting group;
R$_3$ is hydrogen, C$_{1-4}$alkyl or C$_{3-6}$alkenyl optionally substituted by 9 to 10 membered fused bicyclic heteroaryl;
R$_4$ is hydroxy or C$_{3-6}$alkenyloxy optionally substituted by 9 to 10 membered fused bicyclic heteroaryl;
R$_5$ is hydroxy or
R$_4$ and R$_5$ taken together with the intervening atoms form a cyclic group having the following structure:

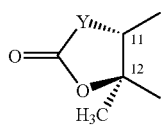

wherein Y is a bivalent radical selected from:
—CH$_2$—, —CH(CN)—, —O—, —N(R$_8$)— and —CH(SR$_8$)—;
R$_6$ is hydrogen or fluorine;
R$_7$ is a heterocyclic group selected from:

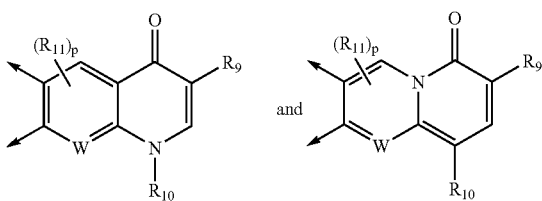

R$_8$ is hydrogen or
C$_{1-4}$alkyl substituted by a group selected from:
optionally substituted phenyl,
optionally substituted 5 or 6 membered heteroaryl, and
optionally substituted 9 to 10 membered fused bicyclic heteroaryl;
R$_9$ is hydrogen, C(O)OR$_{12}$, C(O)NHR$_{12}$ or C(O)CH$_2$NO$_2$;

R$_{10}$ is hydrogen, C$_{1-4}$alkyl, C$_{3-7}$cycloalkyl, optionally substituted phenyl or benzyl;
R$_{11}$ is halogen, C$_{1-4}$alkyl, C$_{1-4}$thioalkyl, C$_{1-4}$alkoxy, NH$_2$, NH(C$_{1-4}$alkyl) or N(C$_{1-4}$alkyl)$_2$;
R$_{12}$ is hydrogen or C$_{1-4}$alkyl;
R$_{13}$ is hydrogen, C$_{1-4}$alkyl, C$_{3-7}$cycloalkyl, optionally substituted phenyl or benzyl, acetyl or benzoyl;
X is —U(CH$_2$)$_m$Z- or X is a group selected from:

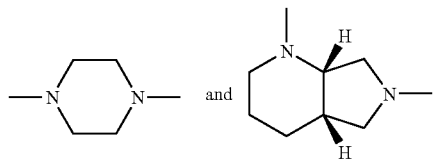

U and Z independently are a divalent radical selected from:
—N(R$_{13}$)—, —O—, —S(O)q-, —N(R$_{13}$)C(O)—, —C(O)N(R$_{13}$)—, and —N[C(O)R$_{13}$]—,
W is a carbon or a nitrogen atom;
n is 0 or an integer from 1 to 5;
m is an integer from 2 to 8;
p is 0, 1 or 2;
q is 0, 1 or 2;
or a pharmaceutically acceptable salt or solvate thereof.
2. A compound according to claim 1 wherein X is NH(CH$_2$)$_{2-3}$NH.
3. A compound according to claim 1 wherein R$_7$ is a heterocyclic group having the following structure:

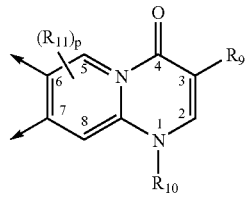

wherein R$_9$, R$_{10}$, R$_{11}$ and p are as defined in claim 1.
4. A compound according to claim 1 or a pharmaceutically acceptable salt or solvate thereof selected from:
4″-O-[3-[[2-[(3-carboxy-7-chloro-1-cyclopropyl-1,4-dihydro-4-oxo-6-quinolinyl)amino]ethyl]amino]propionyl]-8a-aza-8a-homoerythromycin A;
4″-O-[3-[[2-[(3-carboxy-1-cyclopropyl-1,4-dihydro-6-fluoro-4-oxo-7-quinolinyl)amino]ethyl]amino]propionyl]-8a-aza-8a-homoerythromycin A;
4″-O-[3-[[2-[(3-carboxy-7-chloro-1-cyclopropyl-1,4-dihydro-4-oxo-6-quinolinyl)amino]ethyl]amino]propionyl]-6-O-methyl-8a-aza-8a-homoerythromycin A;
4″-O-[3-[(2-[(3-carboxy-1-cyclopropyl-1,4-dihydro-6-fluoro-4-oxo-7-quinolinyl)amino]ethyl]amino]propionyl]-6-O-methyl-8a-aza-8a-homoerythromycin A;
4″-O-[3-[[2-[(7-chloro-1-cyclopropyl-1,4-dihydro-3-methoxycarbonyl-4-oxo-6-quinolinyl)amino]ethyl]amino]propionyl]-6-O-methyl-8a-aza-8a-homoerythromycin A;
4″-O-[3-[4-(3-carboxy-1-cyclopropyl-1,4-dihydro-6-fluoro-4-oxo-7-quinolinyl)-1-piperazinyl]propionyl]-6-O-methyl-8a-aza-8a-homoerythromycin A;

4"-O-[3-[4-(3-carboxy-1-cyclopropyl-1,4-dihydro-4-oxo-7-quinolinyl)piperazinyl]propionyl]-6-O-methyl-8a-aza-8a-homoerythromycin A;

4"-O-[3-[4-(1-cyclopropyl-1,4-dihydro-6-fluoro-4-oxo-7-quinolinyl)-piperazinyl]propionyl]-6-O-methyl-8a-aza-8a-homoerythromycin A;

4"-O-[3-[4-(3-carboxy-7-chloro-1-cyclopropyl-1,4-dihydro-4-oxo-6-quinolinyl)-1-piperazinyl]propionyl]-6-O-methyl-8a-aza-8a-homoerythromycin A;

4"-O-[3-[(4-[(3-carboxy-1-cyclopropyl-1,4-dihydro-6-fluoro-4-oxo-7-quinolinyl)amino]butyl]amino]propionyl]-6-O-methyl-8a-aza-8a-homoerythromycin A;

4"-O-[3-[[3-[(3-carboxy-1-cyclopropyl-6-fluoro-1,4-dihydro-4-oxo-7-quinolinyl)amino]propyl]amino]propionyl]-6-O-methyl-8a-aza-8a-homoerythromycin A;

4"-O-[3-[[3-[(3-carboxy-7-chloro-1-cyclopropyl-1,4-dihydro-4-oxo-7-quinolinyl)amino]propyl]amino]propionyl]-6-O-methyl-8a-aza-8a-homoerythromycin A;

4"-O-[3-[(2-[(3-carboxy-1-cyclopropyl-1,4-dihydro-4-oxo-7-quinolinyl)amino]ethyl]amino]propionyl]-6-O-methyl-8a-aza-8a-homoerythromycin A;

4"-O-[3-[[2-[(3-carboxy-1,4-dihydro-1-ethyl-4-oxo-7-quinolinyl)amino]ethyl]amino]propionyl]-6-O-methyl-8a-aza-8a-homoerythromycin A;

4"-O-[3-[4-(3-carboxy-1-ethyl-6-fluoro-1,4-dihydro-1,8]naphthyridinyl)-4-oxo-[1-piperazinyl]propionyl]-6-O-methyl-8a-aza-8a-homoerythromycin A;

4"-O-[3-[(2-[(1-benzyl-3-carboxy-1,4-dihydro-4-oxo-6-quinolinyl)amino]ethyl]amino]propiony]-6-O-methyl-8a-aza-8a-homoerythromycin A;

4"-O-[3-[[2-[(3-carboxy-7-chloro-1-cyclopropyl-1,4-dihydro-4-oxo-6-quinolinyl)amino]ethyl]amino]propionyl]-6-O-ethyl-8a-aza-8a-homoerythromycin A;

4"-O-[3-[[2-[(3-carboxy-7-chloro-1-cyclopropyl-1,4-dihydro-4-oxo-6-quinolinyl)amino]ethyl]amino]propionyl]-6-O-propyl-8a-aza-8a-homoerythromycin A;

11,12-carbonate-4"-O-[[[2-[(3-carboxy-7-chloro-1-cyclopropyl-1,4-dihydro-4-oxo-6-quinolinyl)amino]ethyl]amino]carbonyl]-11,12-dideoxy-6-O-methyl-8a-aza-8a-homoerythromycin A;

4"-O-[3-[[2-[(3-carboxy-7-chloro-1-cyclopropyl-4-oxo-1,4-dihydro-6-quinolinyl)amino]ethyl]amino]propionyl]-11-O-[3-(3-quinolyl)-2-propenyl]-8a-aza-8a-homoerythromycin A;

4"-O-[3-[[2-[(3-carboxy-7-chloro-1-cyclopropyl-1,4-dihydro-4-oxo-6-quinolinyl)amino]ethyl]amino]propionyl]-6-O-methyl-9a-aza-9a-homoerythromycin A;

4"-O-[3-[[4-[(3-carboxy-1-cyclopropyl-1,4-dihydro-6-fluoro-4-oxo-7-quinolinyl)amino]butyl]amino]propionyl]-6-O-methyl-9a-aza-9a-homoerythromycin A;

4"-O-[3-[[2-[(3-carboxy-7-chloro-1-cyclopropyl-1,4-dihydro-4-oxo-6-quinolinyl)amino]ethyl]amino]propionyl]-6-O-ethyl-9a-aza-9a-homoerythromycin A;

4"-O-[3-[[2-[(3-carboxy-7-chloro-1-cyclopropyl-1,4-dihydro-4-oxo-6-quinolinyl)-amino]ethyl]amino]propionyl]-6-O-propyl-9a-aza-9a-homoerythromycin A;

11,12-carbonate-4"-O-[3-[[2-[(3-carboxy-7-chloro-1-cyclopropyl-1,4-dihydro-4-oxo-6-quinolinyl)amino]ethyl]amino]propionyl]-11,12-dideoxy-azithromycin;

11,12-carbonate-4"-O-[3-[[2-[(3-carboxy-1-cyclopropyl-1,4-dihydro-6-fluoro-4-oxo-7-quinolinyl)amino]ethyl]amino]propiony]-11,12dideoxy azithromycin;

11,12-carbonate-4"-O-[3-[[2-[(3-carboxy-1-cyclopropyl-1,4-dihydro-4-oxo-7-quinolinyl)amino]ethyl]-amino]propiony]-11,12-dideoxy-azithromycin;

4"-O-[3-[[2-[(3-carboxy-7-chloro-1-cyclopropyl-1,4-dihydro-4-oxo-6-quinolinyl)amino]ethyl]amino]propiony]-azithromycin;

4"-O-[[[4-[(3-carboxy-1-cyclopropyl-1,4-dihydro-6-fluoro-4-oxo-7-quinolinyl)amino]butyl]amino]carbonyl]azithromycin;

4"-O-[[[2-[(3-carboxy-7-chloro-1-cyclopropyl-1,4-dihydro-4-oxo-6-quinolinyl)amino]ethyl]amino]carbonyl]-azithromycin;

4"-O-[3-[[2-[(3-carboxy-7-chloro-1-cyclopropyl-1,4-dihydro-4-oxo-3-quinolinyl)amino]ethyl]amino]propiony]-6-O-methyl-azithromycin;

11,12-(aminocarbonyloxy)-4"-O-[3-[[2-[(3-carboxy-7-chloro-1-cyclopropyl-4-oxo-1,4-dihydro-6-quinolinyl)amino]ethyl]amino]propiony]-11,12-dideoxy-6-O-methyl-erythromycin A;

11,12-(aminocarbonyloxy)-4"-O-[3-[[2-[(3-carboxy-1-cyclopropyl-1,4-dihydro-6-fluoro-4-oxo-7-quinolinyl)amino]ethyl]amino]propiony]-11,12-dideoxy-6-O-methyl-erythromycin A;

4"-O-[3-[[2-[(3-carboxy-7-chloro-1-cyclopropyl-1,4-dihydro-4-oxo-6-quinolinyl)amino]ethyl]amino]propionyl]-11,12-dideoxy-6-O-methyl-11,12-(methylaminocarbonyloxy)-erythromycin;

4"-O-[3-[[2-[(3-carboxy-7-chloro-1-cyclopropyl-1,4-dihydro-4-oxo-6-quinolinyl)amino]ethyl]-methylamino]propionyl]-11,12-dideoxy-6-O-methyl-11,12-(methylaminocarbonyloxy)-erythromycin A;

4"-O-[3-[[2-[(3-carboxy-7-chloro-1-cyclopropyl-1,4-dihydro-4-oxo-6-quinolinyl)amino]ethyl]amino]propionyl]-11,12-dideoxy-11,12-(ethylaminocarbonyloxy)-6-O-methyl-erythromycin A;

4"-O-[3-[[2-[(3-carboxy-7-chloro-1-cyclopropyl-1,4-dihydro-4-oxo-6-quinolinyl)amino]ethyl]amino]propionyl]-11,12-dideoxy-6-O-methyl-11,12-[(N-(4-phenyl-butyl)amino)carbonyloxy]-erythromycin A;

4"-O-[3-[[2-[(3-carboxy-7-chloro-1-cyclopropyl-1,4-dihydro-4-oxo-6-quinolinyl)amino]ethyl]amino]propionyl]-6-O-methyl-erythromycin A;

4"-O-[3-[[2-[(3-carboxy-1,4-dihydro-1-ethyl-4-oxo-7-quinolinyl)amino]ethyl]amino]propionyl]-6-O-methyl-erythromycin A;

4"-O-[3-[[2-[(3-carboxy-1-cyclopropyl-1,4-dihydro-4-oxo-7-quinolinyl)amino]ethyl]amino]propionyl]-6-O-methyl-erythromycin A;

4"-O-[3-[[2-[(3-carboxy-1-cyclopropyl-1,4-dihydro-6-fluoro-4-oxo-7-quinolinyl)amino]butyl]amino]propionyl]-6-O-methyl-erythromycin A;

4"-O-[3-[[2-[(3-carboxy-7-chloro1,4-dihydro-1-ethyl-4-oxo-6-quinolinyl)amino]ethyl]amino]propiony]-6-O-methyl-erythromycin A and 4"-O-[3-[[2-[(3-carboxy-1,4-dihydro-1-ethyl-6-fluoro-4-oxo-7-quinolinyl)amino]ethyl]amino]propiony]-6-O-methyl-erythromycin A;

4"-O-[3-[[3-[(3-carboxy-7-chloro-1-cyclopropyl-1,4-dihydro-4-oxo-6-quinolinyl)-amino]propyl]amino]propionyl]-6-O-methyl-erythromycin A;

4"-O-[3-[[3-[(3-carboxy-1-cyclopropyl-1,4-dihydro-6-fluoro-4-oxo-7-quinolinyl)-amino]propyl]amino]propionyl]-6-O-methyl-erythromycin A;

4"-O-[3-[[2-[(3-carboxy-1-cyclopropyl-6-fluoro-1,4-dihydro-4-oxo-7-quinolinyl)-amino]ethyl]amino]propionyl]-6-O-methyl-erythromycin A;

4"-O-[3-[4-(3-carboxy-1-cyclopropyl-6-fluoro-1,4-dihydro-4-oxo-7-quinolinyl)-1-piperazinyl]propionyl]-6-O-methyl-erythromycin A;

4"-O-[3-[4-(3-carboxy-1-ethyl-1,4-dihydro-6-fluoro-4-oxo-[1,8]naphtylridinyl)-1-piperazinyl]propionyl]-6-O-methylerythromycin A;

4"-O-[3-[4-(3-carboxy-1-cyclopropyl-6-fluoro-1,4-dihydro-4-oxo-7-quinolinyl)-1-piperazinyl]ethanoyl]-6-O-methyl-erythromycin A;

4"-O-[2-[[2-[(3-carboxy-7-chloro-1-cyclopropyl-1,4-dihydro-4-oxo-6-quinolinyl)amino]ethyl]amino]ethanoyl]-6-O-methyl-erythromycin A;

4"-O-[2-[[2-[(3-carboxy-1-cyclopropyl-6-fluoro-1,4-dihydro-4-oxo-7-quinolinyl)amino]ethyl]amino]ethanoyl]-6-O-methyl-erythromycin A;

4"-O-[3-[[2-[(3-carbamoyl-1-cyclopropyl-6-fluoro-1,4-dihydro-4-oxo-7-quinolinyl)amino]ethyl]amino]propionyl]-6-O-methyl-erythromycin A;

4"-O-[3-[[2-[(3-carbamoyl-7-chloro-1-cyclopropyl-1,4-dihydro-4-oxo-6-quinolinyl)amino]ethyl]amino]propionyl]-6-O-methyl-erythromycin A;

4"-O-[3-[[2-[(3-carboxy-1-cyclopropyl-4-oxo-1,4-dihydro-6-quinolinyl)amino]ethyl]amino]propionyl]-6-O-methyl-erythromycin A;

4"-O-[3-[[2-[(3-carboxy-7-chloro-1-cyclopropyl-1,4-dihydro-4-oxo-6-quinolinyl)amino]ethyl]amino]propionyl]-6-O-propyl-erythromycin A;

(11S,11aR)-11-(carboxycyanomethyl)-4"-O-[3-[4-(3-carboxy-1-cyclopropyl-1,4-dihydro-4-oxo-7-quinolinyl)piperazinyl]propionyl]-11-deoxy-6-O-methyl-erythromycin A;

(11S,11aR)-11-(carboxycyanomethyl)-4"-O-[3-[4-(1-cyclopropyl-6-fluoro-1,4-dihydro-4-oxo-7-quinolinyl)piperazinyl]propionyl]-11-deoxy-6-O-methyl-erythromycin A;

(11S,11aR)-11-(carboxycyanomethyl)-4"-O-[3-[[2-[(3-carboxy-1-cyclopropyl-6-fluoro-1,4-dihydro-4-oxo-7-quinolinyl)amino]ethyl]amino]propionyl]-11-deoxy-6-O-methyl-erythromycin A;

(11S,11aR)-4"-O-[3-[4-(3-carboxy-7-chloro-1-cyclopropyl-1,4-dihydro-4-oxo-7-quinolinyl)-piperazinyl]propionyl]-11-(carboxycyanomethyl)-11-deoxy-6-O-methyl-erythromycin A;

(11S,11aR)-4"-O-[3-[[2-[(3-carboxy-7-chloro-1-cyclopropyl-1,4-dihydro-4-oxo-6-quinolinyl)amino]ethyl]amino]propionyl]-11-(carboxycyanomethyl)-11-deoxy-6-O-methyl-erythromycin A;

(11S,11aR)-11-(carboxycyanomethyl)-4"-O-[3-[4-(3-carboxy-1-cyclopropyl-1,4-dihydro-6-fluoro-4-oxo-7-quinolinyl)piperazinyl]propionyl]-11-deoxy-6-O-methyl-erythromycin A;

(11S,11aR)-11-(carboxycyanomethyl)-4"-O-[3-[rel-(4aS,7aS)-6-(3-carboxy-1-cyclopropyl-6-fluoro-1,4-dihydro-4-oxo-7-quinolinyl)octahydro-1H-pyrrolo[3,4-b]pyridin-1-yl]propionyl]-11-deoxy-6-O-methyl-erythromycin A;

(11S,11aR)-11-(carboxycyanomethyl)-4"-O-[3-[4-(3-carboxy-1-ethyl-6-fluoro-1,4-dihydro-4-oxo-[1,8]naphthyridinyl)piperazinyl]propionyl]-11-deoxy-6-O-methyl-erythromycin A;

(11S,11aR)-11-(carboxycyanomethyl)-4"-O-[3-[[2-[(3-carboxy-1,4-dihydro-1-ethyl-4-oxo-7-quinolinyl)amino]ethyl]amino]propionyl]-11-deoxy-6-O-methyl-erythromycin A;

(11S,11aR)-11-(carboxycyanomethyl)-4"-O-[3-[[2-[(3-carboxy-1-cyclopropyl-1,4-dihydro-4-oxo-7-quinolinyl)amino]ethyl]amino]propionyl]-11-deoxy-6-O-methyl-erythromycin A; 4"-O-[3-[4-(3-carboxy-1-cyclopropyl-1,4-dihydro-6-fluoro-4-oxo-7-quinolinyl)-1-piperazinyl]propionyl]-roxithromycin;

4"-O-[3-[4-(3-carboxy-1-ethyl-6-fluoro-1,4-dihydro-4-oxo-[1,8]naphthyridinyl)piperazinyl]propionyl]-roxithromycin;

4"-O-[3-[4-(3-carboxy-7-chloro-1-cyclopropyl-1,4-dihydro-4-oxo-6-quinolinyl)amino]ethyl]amino]propionyl]-roxithromycin;

4"-O-[3-[4-(3-carboxy-1-cyclopropyl-1,4-dihydro-6-fluoro-4-oxo-7-quinolinyl)amino]ethyl]amino]propionyl]-roxithromycin;

4"-O-[2-[[3-[(3-carboxy-7-chloro-1-cyclopropyl-1,4-dihydro-4-oxo-6-quinolinyl)-amino]propyl]amino]ethanoyl]-6-O-methyl-erythromycin A;

4"-O-[2-[[3-[(3-carboxy-1-cyclopropyl-1,4-dihydro-6-fluoro-4-oxo-7-quinolinyl)-amino]propyl]amino]ethanoyl]-6-O-methyl-erythromycin A;

4"-O-[2-[[2-[(7-chloro-1-cyclopropyl-1,4-dihydro-4-oxo-6-quinolinyl)-amino]ethyl]amino]propionyl]-6-O-methyl-erythromycin A;

4"-O-[2-[[2-[(1-cyclopropyl-6-fluoro-1,4-dihydro-4-oxo-7-quinolinyl)-amino]ethyl]amino]propionyl]-6-O-methyl-erythromycin A;

4"-O-[3-[acetyl-[2-[(3-carboxy-7-chloro-1-cyclopropyl-1,4-dihydro-4-oxo-6-quinolinyl)-amino]ethyl]amino]propionyl]-6-O-methyl-erythromycin A;

4"-O-(3-(2-(3-carboxy-7-chloro-1-cyclopropyl-4-oxo-1,4-dihydro-6-quinolinyl)amino)ethyl)-methyl-amino)propionyl)-11,12-dideoxy-11,12-(ethylaminocarbonyloxy)-6-O-methylerythromycin A;

4"-O-(3-{[2-(1-cyclopropyl-6-fluoro-3-methoxycarbonyl-4-oxo-1,4-dihydro-quinolin-7-ylamino)-ethyl]-amino}-propionyl)-11,12-dideoxy-6-O-methyl-11,12-(aminocarbonyloxy)-erythromycin A;

4"-O-{3-[(2-[(3-carboxymethyl-7-chloro-1-cyclopropyl-4-oxo-1,4-dihydro-6-quinolin yl)amino]ethyl)amino]propionyl}-11,12-dideoxy-6-O-methyl-11,12-(aminocarbonyloxy)-erythromycin A;

4"-O-{3-[(2-[(3-carboxymethyl-7-chloro-1-cyclopropyl-4-oxo-1,4-dihydro-6-quinolinyl)amino]ethyl)-methylamino]propionyl}-11,12-dideoxy-6-O-methyl-11,12-(aminocarbonyloxy)-erythromycin A;

4"-O-(3-{[2-(3-carboxy-1-cyclopropyl-4-oxo-1,4-dihydro-quinolin-6-ylamino)-ethyl]-methyl-amino}-propionyl)-11,12-dideoxy-6-O-methyl-11,12-(aminocarbonyloxy)-erythromycin A;

4"-O-{3-[(2-[(3-carboxy-1-cyclopropyl-4-oxo-1,4-dihydro-6-quinolinyl)amino]ethyl)amino]propionyl}-11,12-dideoxy-6-O-methyl-11,12-[amino(methyl)carbonyloxy]-erythromycin A;

4"-O-{3-[(2-[(3-carboxy-7-chloro-1-cyclopropyl-4-oxo-1,4-dihydro-6-quinolin yl)amino]ethyl)methylamino]propionyl}-6-O-methyl-erythromycin A; 4"-O-{3-[(2-[(3-carboxymethyl-7-chloro-1-cyclopropyl-4-oxo-1,4-dihydro-6-quinolin yl)amino]ethyl)amino]propiony}-6-O-methyl-erythromycin A;

4"-{3-[(2-[(3-carboxy-1-methyl-1,4-dihydro-4-oxo-7-quinolinyl)amino]ethyl]amino]propionyl}-6-O-methyl-erythromycin A;

4"-{3-[(2-[(3-carboxy-1-cyclopropyl-1,4-dihydro-4-oxo-7-quinolinyl)amino]butyl)amino]propionyl}-6-O-methyl-erythromycin A;

4"-O-{[(2-[(3-carboxy-1-ethyl-1,4-dihydro-4-oxo-7-quinolinyl)amino]ethyl)methylamino]propionyl}-6-O-methyl-erythromycin A;

4"-O-{[(2-[(3-carboxy-1-cyclopropyl-1,4-dihydro-4-oxo-7-quinolinyl)amino]ethyl)methylamino]propionyl}-6-O-methyl-erythromycin A;

4"-O-{3-[(2-[(3-carboxy-1-cyclopropyl-1,4-dihydro-4-oxo-7-quinolinyl)amino]butyl)amino]propionyl}-6-O-methyl-8a-aza-8a-homoerythromycin A;

4"-O-{3-[(2-[(3-carboxy-1-methyl-1,4-dihydro-4-oxo-7-quinolinyl)amino]ethyl]amino]propionyl}-6-O-methyl-8a-aza-8a-homoerythromycin A;

11,12-(aminocarbonyloxy)-4"-O-{3-[(2-[(3-carboxy-1-ethyl-4-oxo-1,4-dihydro-7-quinolinyl)amino]ethyl)amino]propionyl}-11,12-dideoxy-6-O-methyl-erythromycin A;

4"-O-{3-[(2-[(3-carboxy-1-ethyl-1,4-dihydro-4-oxo-7-quinolinyl)amino]ethyl)amino]propionyl}-11,12-dideoxy-11,12-(methylaminocarbonyloxy)-6-O-methyl-erythromycin A;

4"-O-{3-[(2-[(3-carboxy-1-ethyl-1,4-dihydro-4-oxo-7-quinolinyl)amino]ethyl)amino]propionyl}-11,12-dideoxy-11,12-(ethylaminocarbonyloxy)-6-O-methyl-erythromycin A;

11,12-(aminocarbonyloxy)-4"-O-{3-[(2-[(3-carboxy-1-cyclopropyl-4-oxo-1,4-dihydro-6-quinolinyl)amino]ethyl)amino]propionyl}-11,12-dideoxy-6-O-methyl-erythromycin A;

11,12-(aminocarbonyloxy)-4"-O-{[(2-[(3-carboxy-1-cyclopropyl-1,4-dihydro-6-fluoro-4-oxo-7-quinolinyl)amino]ethyl)methylamino]propionyl}-11,12-dideoxy-6-O-methyl-erythromycin A;

4"-O-[3-[[2-[(3-carboxy-1-cyclopropyl-1,4-dihydro-4-oxo-7-quinolinyl)amino]ethyl]amino]propionyl]-azithromycin;

4"-O-[3-[[2-[(3-carboxy-1-methyl-1,4-dihydro-4-oxo-7-quinolinyl)amino]ethyl]amino]propionyl]-azithromycin;

4"-O-[3-[[2-[(3-carboxy-1-cyclopropyl-1,4-dihydro-4-oxo-7-quinolinyl)amino]butyl]amino]propionyl]-azithromycin;

4"-O-[3-[[2-[(3-carboxy-7-chloro-1-cyclopropyl-1,4-dihydro-4-oxo-6-quinolinyl)amino]ethyl]-methyl-amino]propionyl]-azithromycin;

11,12-carbonate-4"-O-[3-[[2-[(3-carboxy-1-cyclopropyl-1,4-dihydro-6-fluoro-4-oxo-7-quinolinyl)amino]ethyl]methylamino]propionyl]-11,12-dideoxy-azithromycin;

11,12-carbonate-4"-O-[3-[[2-[(3-carboxy-1-cyclopropyl-1,4-dihydro-7-chloro-4-oxo-6-quinolinyl)amino]ethyl]methylamino]propionyl]-11,12-dideoxy-azithromycin;

11,12-carbonate-4"-O-[3-[[2-[(3-carboxy-1-cyclopropyl-1,4-dihydro-4-oxo-6-quinolinyl)amino]ethyl]methylamino]propionyl]-11,12-dideoxy-azithromycin;

11,12-carbonate-4"-O-[3-[[2-[(3-carboxy-1-cyclopropyl-1,4-dihydro-4-oxo-6-quinolinyl)amino]ethyl]amino]propionyl]-11,12-dideoxy-azithromycin;

11,12-carbonate-4"-O-[3-[[2-[(3-carboxy-1-ethyl-1,4-dihydro-4-oxo-7-quinolinyl)amino]ethyl]amino]propionyl]-11,12-dideoxy-azithromycin;

4"-O-{3-[(2-[3-carboxy-6-fluoro-8-methoxy-1-cyclopropyl-4-oxo-1,4-dihydro-7-(quinolinyl)amino]ethyl)amino]propionyl}-azithromycin;

4"-O-{3-[(2-[3-carboxy-6-fluoro-8-methoxy-1-cyclopropyl-4-oxo-1,4-dihydro-7-(quinolinyl)amino]ethyl)amino]propionyl}-6-O-methyl-erythomycin;

4"-O-(3-{[2-(7-chloro-1-cyclopropyl-3-methoxycarbonyl-4-oxo-1,4-dihydro-quinolin-6-ylamino)-ethyl]-amino}-propionyl)-azithromycin;

4"-O-(3-{[2-(7-chloro-1-cyclopropyl-3-methoxycarbonyl-4-oxo-1,4-dihydro-quinolin-6-ylamino)-ethyl]-methyl-amino}-propionyl)-azithromycin;

4"-O-(3-{[2-(1-cyclopropyl-3-methoxycarbonyl-4-oxo-1,4-dihydro-quinolin-6-ylamino)-ethyl]-amino}-propionyl)-azithromycin;

4"-O-{3-[2-(1-cyclopropyl-6-fluoro-3-methoxycarbonyl-4-oxo-1,4-dihydro-quinolin-7-ylamino)-ethylamino]-propionyl}-azithromycin;

4"-O-{3-[(2-[(3-carboxy-1-ethyl-1,4-dihydro-4-oxo-7-quinolinyl)amino]ethyl)amino]propionyl}-azithromycin;

4"-O-{3-[(2-[(3-carboxy-1-cyclopropyl-1,4-dihydro-4-oxo-6-quinolinyl)amino]ethyl)amino]propionyl}-azithromycin;

4"-O-{3-[(2-[(3-carboxy-1-cyclopropyl-6-fluoro-1,4-dihydro-4-oxo-7-quinolinyl)amino]ethyl)amino]propiony}-azithromycin;

4"-O-{3-[(2-[(3-carboxy-1-ethyl-1,4-dihydro-4-oxo-7-quinolinyl)amino]ethyl)methylamino]propionyl}-azithromycin;

4"-O-{3-[(2-[(3-carboxy-1-cyclopropyl-1,4-dihydro-4-oxo-7-quinolinyl)amino]ethyl)methylamino]propionyl}-azithromycin;

4"-O-{3-[(2-[(3-carboxy-1-cyclopropyl-1,4-dihydro-4-oxo-6-quinolinyl)amino]ethyl)methylamino]propionyl}-azithromycin;

4"-O-{3-[(2-[(3-carboxy-1-cyclopropyl-1,4-dihydro-6-fluoro-4-oxo-7-quinolinyl)amino]ethyl)methylamino]propionyl}-azithromycin;

4"-O-{3-[(2-[(3-carboxy-1-cyclopropyl-6-fluoro-4-oxo-1,4-dihydro-7-quinolinyl)amino]ethyl)amino]propiony}-11,12-dideoxy-6-O-methyl-11,12-(methylaminocarbonyloxy)-erythromycin A;

11,12-(aminocarbonyloxy)-4"-O-(3-{[2-(3-carboxy-7-chloro-1-cyclopropyl-4-oxo-1,4-dihydro-quinolin-6-ylamino)-ethyl]-methyl-amino}-propionyl)-11,12-dideoxy-6-O-methyl-erythromycin A;

4"-O-[3-[[2-[(3-carboxy-7-chloro-1-ethyl-1,4-dihydro-4-oxo-6-quinolinyl)amino]ethyl]amino]propionyl]-6-O-methyl-erythromycin A;

4"-O-[3-[[2-[(3-carboxy-7-chloro-1-ethyl-1,4-dihydro-4-oxo-6-quinolinyl)amino]ethyl]amino]propionyl]-azithromycin;

4"-O-[3-[[2-[(3-carboxy-1-ethyl-1,4-dihydro-4-oxo-6-quinolinyl)amino]ethyl]amino]propionyl]-6-O-methyl-erythromycin A;

4"-O-[3-[[2-[(3-carboxy-1-ethyl-1,4-dihydro-4-oxo-6-quinolinyl)amino]ethyl]amino]propionyl]-azithromycin;

4"-O-[3-[(2-[(1-benzyl-3-carboxy-1,4-dihydro-4-oxo-7-quinolinyl)amino]ethyl]amino]propiony]-6-O-ethyl-8a-aza-8a-homoerythromycin A; and 4"-O-[3-[(2-[(1-benzyl-3-carboxy-1,4-dihydro-4-oxo-7-quinolinyl)amino]ethyl]amino]propiony]-6-O-propyl-8a-aza-8a-homoerythromycin A.

5. A compound according to claim 1 selected from:

4"-O-[3-[[2-[(3-carboxy-7-chloro-1-cyclopropyl-1,4-dihydro-4-oxo-6-quinolinyl)amino]ethyl]amino]propionyl]-6-O-methyl-8a-aza-8a-homoerythromycin A;

11,12-carbonate-4"-O-[3-[[2-[(3-carboxy-7-chloro-1-cyclopropyl-1,4-dihydro-4-oxo-6-quinolinyl)amino]ethyl]amino]propionyl]-11,12-dideoxy-azithromycin;

11,12-carbonate-4"-O-[3-[[2-[(3-carboxy-1-cyclopropyl-1,4-dihydro-6-fluoro-4-oxo-7-quinolinyl)amino]ethyl]amino]propiony]-11,12dideoxy azithromycin;

11,12-carbonate-4"-O-[3-[[2-[(3-carboxy-1-cyclopropyl-1,4-dihydro-4-oxo-7-quinolinyl)amino]ethyl]-amino]propiony]-11,12-dideoxy-azithromycin;

4"-O-[3-[[2-[(3-carboxy-7-chloro-1-cyclopropyl-1,4-dihydro-4-oxo-6-quinolinyl)amino]ethyl]amino]propiony]-azithromycin;

4"-O-[3-[[2-[(3-carboxy-7-chloro-1-cyclopropyl-1,4-dihydro-4-oxo-6-quinolinyl)amino]ethyl]amino]propionyl]-11,12-dideoxy-11,12-(ethylaminocarbonyloxy)-6-O-methyl-erythromycin A;

4"-O-[3-[[2-[(3-carboxy-7-chloro-1-cyclopropyl-1,4-dihydro-4-oxo-6-quinolinyl)amino]ethyl]amino]propionyl]-6-O-methyl-erythromycin A;

4"-O-[3-[[2-[(3-carboxy-1,4-dihydro-1-ethyl-4-oxo-7-quinolinyl)amino]ethyl]amino]propionyl]-6-O-methyl-erythromycin A;

4"-O-[3-[[2-[(3-carboxy-1-cyclopropyl-1,4-dihydro-4-oxo-7-quinolinyl)amino]ethyl]amino]propionyl]-6-O-methyl-erythromycin A;

4"-O-[3-[[2-[(3-carboxy-1-cyclopropyl-4-oxo-1,4-dihydro-6-quinolinyl)amino]ethyl]amino]propionyl]-6-O-methyl-erythromycin A;

(11S,11aR)-4"-O-[3-[[2-[(3-carboxy-7-chloro-1-cyclopropyl-1,4-dihydro-4-oxo-6-quinolinyl)amino]ethyl]amino]propionyl]-11-(carboxycyanomethyl)-11-deoxy-6-O-methyl-erythromycin A;

(11S,11aR)-11-(carboxycyanomethyl)-4"-O-[3-[[2-[(3-carboxy-1-cyclopropyl-1,4-dihydro-4-oxo-7-quinolinyl)amino]ethyl]amino]propionyl]-11-deoxy-6-O-methyl-erythromycin A;

4"-O-[3-[4-(3-carboxy-7-chloro-1-cyclopropyl-1,4-dihydro-4-oxo-6-quinolinyl)amino]ethyl]amino]propionyl]-roxithromycin;

4"-O-(3-(2-(3-carboxy-7-chloro-1-cyclopropyl-4-oxo-1,4-dihydro-6-quinolinyl)amino)ethyl)-methyl-amino)propionyl)-11,12-dideoxy-11,12-(ethylaminocarbonyloxy)-6-O-methylerythromycin A;

4"-O-{3-[(2-[(3-carboxymethyl-7-chloro-1-cyclopropyl-4-oxo-1,4-dihydro-6-quinolinyl)amino]ethyl)amino]propiony}-6-O-methyl-erythromycin A;

11,12-(aminocarbonyloxy)-4"-O-{3-[(2-[(3-carboxy-1-cyclopropyl-4-oxo-1,4-dihydro-6-quinolinyl)amino]ethyl)amino]propionyl}-11,12-dideoxy-6-O-methyl-erythromycin A;

4"-O-[3-[[2-[(3-carboxy-7-chloro-1-cyclopropyl-1,4-dihydro-4-oxo-6-quinolinyl)amino]ethyl]-methyl-amino]propionyl]-azithromycin;

11,12-carbonate-4"-O-[3-[[2-[(3-carboxy-1-cyclopropyl-1,4-dihydro-4-oxo-6-quinolinyl)amino]ethyl]methylamino]propionyl]-11,12-dideoxy-azithromycin;

4"-O-(3-{[2-(7-chloro-1-cyclopropyl-3-methoxycarbonyl-4-oxo-1,4-dihydro-quinolin-6-ylamino)-ethyl]-amino}-propionyl)-azithromycin;

4"-O-(3-{[2-(7-chloro-1-cyclopropyl-3-methoxycarbonyl-4-oxo-1,4-dihydro-quinolin-6-ylamino)-ethyl]-methyl-amino}-propionyl)-azithromycin;

4"-O-{3-[(2-[(3-carboxy-1-cyclopropyl-1,4-dihydro-4-oxo-7-quinolinyl)amino]ethyl)methylamino]propionyl}-azithromycin; and 4"-O-[3-[[2-[(3-carboxy-1-ethyl-1,4-dihydro-4-oxo-6-quinolinyl)amino]ethyl]amino]propionyl]-6-O-methyl-erythromycin A.

6. A process for the preparation of a compound as claimed in claim 1 which comprises:

a) reacting a compound of formula (II)

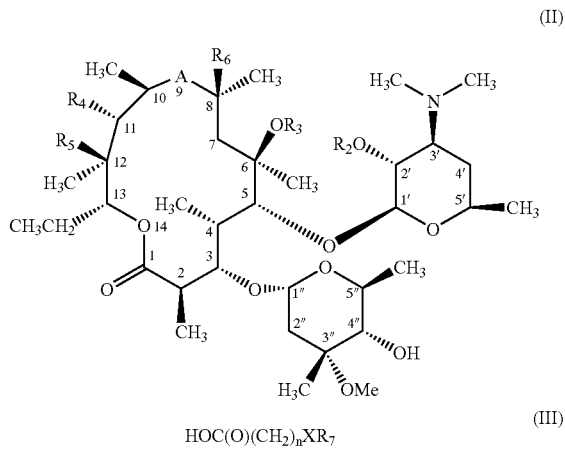

(II)

HOC(O)(CH$_2$)$_n$XR$_7$      (III)

with a suitable activated derivative of the acid (III), wherein n is an integer 1 to 5, X and R$_7$ have the meanings defined in claim 1, to produce a compound of formula (I) wherein n is an integer 1 to 5;

b) reacting a compound of formula (II), in which the 4" hydroxy is suitable activated, with a compound of formula XR$_7$(IV), wherein R$_7$, m and Z have the meanings defined in claim 1 and X is —U(CH$_2$)mZ-, in which U is a group selected from:

—N(R$_{13}$)—, —O—, and —S—, to produce a compound of formula (I) wherein n is 0 and U is a group selected from —N(R$_{13}$)—, —O—, and —S—;

c) reacting a compound of formula (V)

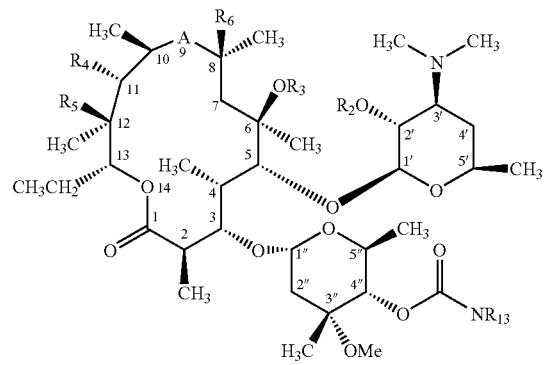

(V)

wherein R$_{13}$ has the meaning defined in claim 1 with a suitable activated derivative of the carboxylic acid HOC(O)C(O)(CH$_2$)$_m$ZR$_7$(VIIb), wherein R$_7$ and Z have the meanings defined in claim 1, to produce a compound of formula (I) wherein n is 0 and U is —N(R$_{13}$)C(O)—;

d) reacting a compound of formula (VII)

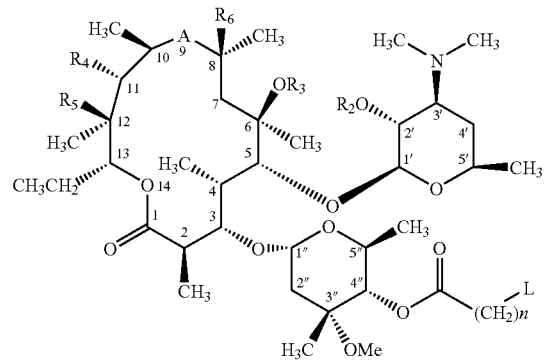

(VII)

with a compound of formula XR$_7$ (IV), wherein R$_7$ and X have the meanings defined in claim 1 in which U is a group selected from —N(R$_{13}$)—, —O—, and —S—, and L is suitable leaving group, to produce a compound of formula (I) wherein n is 1 to 5 and U is a group selected from:

$N(R_{13})$—, —O—, and —S—; or e) reacting a compound of formula (IX), with a compound of formula $XR_7$ (IV),

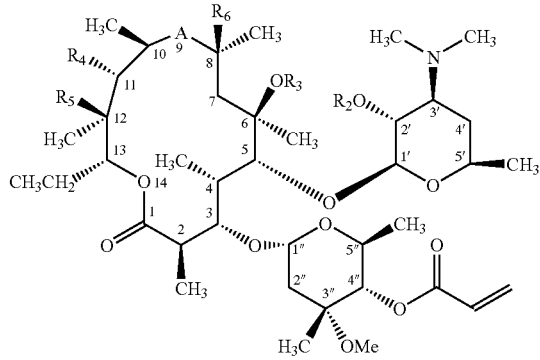

(IX)

wherein $R_7$ and X have the meanings defined in claim 1, in which U is a group selected from —$N(R_{13})$—, —O—, and —S—, to produce a compound of formula (I) wherein n is 2 and U is a group selected from: —$N(R_{13})$—, —O—, and —S—;

and thereafter, if required, subjecting the resulting compound to one or more of the following operations:

i) removal of the protecting group $R_2$ and ii) conversion of the resultant compound of formula (I) into a pharmaceutically acceptable salt or solvate thereof.

7. A pharmaceutical composition comprising a compound as claimed in claim 1, or a pharmaceutically acceptable salt or solvate thereof, in admixture with one or more pharmaceutically acceptable carriers or excipients.

8. A method for the treatment of the human or non human animal body to combat bacterial infection comprising administration of an effective amount of a compound as claimed in claim 1 or a pharmaceutically acceptable salt or solvate thereof.

9. A method of treatment according to claim 8 of systemic or topical bacterial infections in a human or animal in need thereof.

* * * * *